US011390651B2

(12) United States Patent
Lenouen et al.

(10) Patent No.: US 11,390,651 B2
(45) Date of Patent: Jul. 19, 2022

(54) VACCINE CANDIDATES FOR HUMAN RESPIRATORY SYNCYTIAL VIRUS (RSV) HAVING ATTENUATED PHENOTYPES

(71) Applicants: THE USA, AS REPRESENTED BY THE SECRETARY, DEPT. OF HEALTH AND HUMAN SERVICES, Bethesda, MD (US); CODAGENIX, INC., Farmingdale, NY (US)

(72) Inventors: Cyril Lenouen, Bethesda, MD (US); Ursula J. Buchholz, Silver Spring, MD (US); Peter L. Collins, Silver Spring, MD (US); Steffen Mueller, Stony Brook, NY (US)

(73) Assignees: The USA, Secretary, DHHS, Bethesda, MD (US); Codagenix, Inc., Stony Brook, NY (US)

( * ) Notice: Subject to any disclaimer, the term of this patent is extended or adjusted under 35 U.S.C. 154(b) by 138 days.

(21) Appl. No.: 17/008,025

(22) Filed: Aug. 31, 2020

(65) Prior Publication Data

US 2021/0188920 A1 Jun. 24, 2021

Related U.S. Application Data

(63) Continuation of application No. 16/335,099, filed as application No. PCT/US2017/053047 on Sep. 22, 2017, now Pat. No. 10,808,012.

(60) Provisional application No. 62/400,476, filed on Sep. 27, 2016, provisional application No. 62/399,133, filed on Sep. 23, 2016.

(51) Int. Cl.

| | |
|---|---|
| ***A61K 39/155*** | (2006.01) |
| ***C12N 7/00*** | (2006.01) |
| ***A61K 39/12*** | (2006.01) |
| ***A61K 39/00*** | (2006.01) |
| ***C07K 14/005*** | (2006.01) |
| ***C07K 14/08*** | (2006.01) |
| ***C12N 7/04*** | (2006.01) |
| ***A61P 31/20*** | (2006.01) |
| ***A61K 9/00*** | (2006.01) |

(52) U.S. Cl.

CPC ............ *C07K 14/08* (2013.01); *A61K 9/0019* (2013.01); *A61K 9/0043* (2013.01); *A61K 39/155* (2013.01); *A61P 31/20* (2018.01); *C12N 7/04* (2013.01); *C12N 2760/00021* (2013.01); *C12N 2760/00034* (2013.01); *C12N 2760/00062* (2013.01)

(58) Field of Classification Search

CPC .. C12N 7/00; A61K 2039/5254; A61K 39/12; A61K 39/155; C07K 14/005

See application file for complete search history.

(56) References Cited

U.S. PATENT DOCUMENTS

| | | | | |
|---|---|---|---|---|
| 9,957,486 | B2 | 5/2018 | Collins et al. | |
| 2012/0264217 | A1 | 10/2012 | Moore et al. | |
| 2015/0368622 | A1* | 12/2015 | Collins ................ | C07K 14/005 435/236 |
| 2018/0208906 | A1 | 7/2018 | Collins et al. | |
| 2019/0233476 | A1 | 8/2019 | LeNouen et al. | |

FOREIGN PATENT DOCUMENTS

| | | |
|---|---|---|
| EP | 1690940 | 8/2006 |
| WO | WO 98/02530 | 1/1998 |
| WO | WO 98/53078 | 11/1998 |
| WO | WO 02/42326 | 5/2002 |
| WO | WO 2006/042156 | 4/2006 |
| WO | WO 2006/085987 | 8/2006 |
| WO | WO 2008/121992 | 10/2008 |
| WO | WO 2010/053883 | 5/2010 |
| WO | WO 2018/057950 | 3/2018 |

OTHER PUBLICATIONS

Examination Report of Australian Patent Application No. 2017332789 dated Oct. 19, 2020.

Sequence alignment of 8387 to 14884 of SEQ ID No. 5 with geneseq database access No. AAV18276 by Udem et al. in WO9813501 on Apr. 2, 1998, 13 pages.

Sequence alignment of 8387 to 14884 of SEQ ID No. 5 with geneseq database access No. AAT63430 by Collins et al. in WO 97/12032.

Abil et al. "Synthetic biology for therapeutic applications," Molecular Pharmaceutics, 2015, vol. 12, No. 2, pp. 322-331.

Atkinson et al. "The influence of CpG and UpA dinucleotide frequencies on RNA virus replication and characterization of the innate cellular pathways underlying virus attenuation and enhanced replication," Nucleic Acids Research, 2014, vol. 42, No. 7, pp. 4527-4545.

Belshe et al. "Experimental respiratory syncytial virus infection of four species of primates," Journal of Medical Virology, 1977, vol. 1, pp. 157-162 (Abstract Only).

Blondot et al. "Structure and functional analysis of the RNA- and viral phosphoprotein-binding domain of respiratory syncytial virus M2-1 protein," PLoS Pathog, 2012, vol. 8, No. 5, e1002734.

(Continued)

*Primary Examiner* — Barry A Chestnut

(74) *Attorney, Agent, or Firm* — McBee Moore & Vanik IP, LLC

(57) ABSTRACT

Reported herein are presumptively de-attenuating mutations that are useful, either individually or in combinations that may include other known mutations, in producing recombinant strains of human respiratory syncytial virus (RSV) exhibiting attenuation phenotypes. Also described herein is a novel RSV construct, Min_L-NPM2-1(N88K)L, which exhibits an attenuated phenotype, is stable and is as immunogenic as wild type RSV. The recombinant RSV strains described here are suitable for use as live-attenuated RSV vaccines. Exemplary vaccine candidates are described. Also provided are polynucleotide sequences capable of encoding the described viruses, as well as methods for producing and using the viruses.

28 Claims, 30 Drawing Sheets

Specification includes a Sequence Listing.

(56) References Cited

OTHER PUBLICATIONS

Broadbent et al. "Evaluation of the attenuation, immunogenicity, and efficacy of a live virus vaccine generated by codon-pair bias de-optimization of the 2009 pandemic H1N1 influenza virus, in ferrets," Vaccine, Jan. 2016, vol. 34, No. 4, pp. 563-570.
Brooks et al. "CHARMM: the biomolecular simulation program," Journal of Computational Chemistry, 2009, vol. 30, No. 10, pp. 1545-1614 (Abstract Only).
Buchholz et al., "Chimeric bovine respiratory syncytial virus with glycoprotein gene substitutions from human respiratory syncytial virus /HRSV): effects on host range and evaluation as a live-attenuated vaccine", Journal of Virology, Feb. 2000, vol. 74, No. 3, pp. 1187-1199.
Buchholz et al. "Generation of bovine respiratory syncytial virus (BRSV) from cDNA: BRSV NS2 is not essential for virus replication in tissue culture, and the human RSV leader region acts as a functional BRSV genome promoter," J. Virol., 1999, vol. 73, No. 1, pp. 251-259.
Bukreyev et al. "Granulocyte-macrophage colony-stimulating factor expressed by recombinant respiratory syncytial virus attenuates viral replication and increases the level of pulmonary antigen-presenting cells," J. Virol. 2001, vol. 75, pp. 12128-12140.
Bukreyev et al. "Recombinant respiratory syncytial virus from which the entire SH gene has been deleted grows efficiently in cell culture and exhibits site-specific attenuation in the respiratory tract of the mouse.," J. Virol., 1997, vol. 71, No. 12, pp. 8973-8982.
Bull et al. "Slow fitness recovery in a codon-modified viral genome," Mol. Biol. Evol., 2012, vol. 29, No. 10, pp. 2997-3004.
Bull "Evolutionary reversion of live viral vaccines: Can genetic engineering subdue it?" Virus Evolutions, 2015, vol. 1, No. 1, vev005.
Burns et al. "Modulation of poliovirus replicative fitness in HeLa cells by deoptimization of synonymous codon usage in the capsid region," J. Virol., 2006, vol. 80, No. 7, pp. 3259-3272.
Chapman eta l. Initial genome sequencing and analysis of multiple myeloma, Nature, 2011, vol. 471, No. 7339, pp. 467-472.
Cheng et al. "Development of live-attenuated arenavirus vaccines based on codon deoptimization," J. Virol, 2015, vol. 89, No. 7, pp. 3523-3533.
Cheng et al. "Effective amplification of long targets from cloned inserts and human genomic DNA," Proc. Natl. Acad. Sci. USA, 1994, vol. 91, No. 12, pp. 5695-5699.
Chirkova et al. "Respiratory Syncytial Virus G Protein CX3C Motif Impairs Human Airway Epithelial and Immune Cell Responses," J. Virol., 2013, vol. 87, No. 24, pp. 13466-13479.
Coleman et al. "Virus Attenuation by Genome-Scale Changes in Codon Pair Bias," Science, Jun. 2008, vol. 320, pp. 1784-1787.
Coleman et al. "Designed Reduction of *Streptococcus pneumoniae* Pathogenicity via Synthetic Changes in Virulence Factor Codon-pair Bias," The Journal of Infectious Diseases, May 2011, vol. 203, No. 9, pp. 1264-1273.
Collins et al. "Viral and Host Factors in Human Respiratory Syncytial Virus Pathogenesis," Journal of Virology, 2008, vol. 82, No. 5, pp. 2040-2055.
Collins et al. "Progress in understanding and controlling respiratory syncytial virus: Still crazy after all these years" Virus Research, 2011, vol. 162, No. 1-2, pp. 80-99.
Collins et al. "Respiratory Syncytial Virus: Virology, Reverse Genetics, and Pathogenesis of Disease," Current Topics in Microbiology and Immunology, 2013, vol. 372, pp. 3-38.
Collins et al. "Production of infectious human respiratory syncytial virus from cloned cDNA confirms an essential role for the transcription elongation factor from the 5' proximal open reading frame of the M2 mRNA in gene expression and provides a capability for vaccine development," Proc. Natl. Acad. Sci. USA, 1995, vol. 92, pp. 11563-11567.
Collins et al. "Nucleotide Sequences for the Gene Junctions of Human Respiratory Syncytial Virus Reveal Distinctive Features of Intergenic Structure and Gene Order," Proc. Natl. Acad. Sci. USA, 1986, vol. 83, No. 13, pp. 4594-4598.
Collins et al. "Gene overlap and site-specific attenuation of transcription of the viral polymerase L gene of human respiratory syncytial virus," Proc. Natl. Acad. Sci. USA, 1987, vol. 84, No. 15, pp. 5134-5138.
Collins et al. "Rational Design of Live-Attenuated Recombinant Vaccine Virus for Human Respiratory Syncytial Virus by Reverse Genetics," Advances in Virus Research, 1999, vol. 54, pp. 423-451.
Connors et al. "A Cold-Passaged, Attenuated Strain of Human Respiratory Syncytial Virus Contains Mutations in the F and L Genes," Virology, 1995, vol. 208, No. 2, pp. 478-484.
Crowe et al. "A comparison in chimpanzees of the immunogenicity and efficacy of live attenuated respiratory syncytial virus (RSV) temperature-sensitive mutant vaccines and vaccinia virus recombinants that express the surface glycoproteins of RSV," Vaccine, 1993, vol. 11, No. 14, pp. 1395-1404 (Abstract Only).
Diaz-San et al. "Synonymous deoptimization of the foot-and-mouth disease virus causes attenuation in vivo while inducing a strong neutralizing antibody response," J. Virol., 2016, vol. 90, No. 3, pp. 1298-1310.
Durbin et al. "Recovery of Infectious Human Parainfluenza Virus Type 3 from cDNA," Virology, 1997, vol. 235, No. 2, pp. 323-332.
Fearns et al. "Role of the M2-1 transcription antitermination protein of respiratory syncytial virus in sequential transcription," J. Virol., 1999, vol. 73, No. 7, pp. 5852-5864.
Firestone et al. "Nucleotide Sequence Analysis of the Respiratory Syncytial Virus Subgroup A Cold-Passaged (cp) Temperature Sensitive (ts) cpts-248/404 Live Attenuated Virus Vaccine Candidate," Virology, 1996, vol. 225, No. 2, pp. 419-422.
Friedewald et al. "Low-Temperature-Grown RS Virus in Adult Volunteers," J. Amer. Med. Assoc., 1968, vol. 204, pp. 690-694 (Abstract Only).
Gaunt et al. "Elevation of CpG frequencies in influenza A genome attenuates pathogenicity but enhances host response to infection," Elife 5, Feb. 2016, e12735, 19 pages.
Gharpure et al. "Temperature-sensitive Mutants of Respiratory Syncytial Virus," J. Virol., 1969, vol. 3, No. 4, pp. 414-421.
Hanley "The double-edged sword: How evolution can make or break a live-attenuated virus vaccine," Evolution (N Y), 2011, vol. 4, No. 4, pp. 635-643.
Hoffman et al. "An infectious clone of human parainfluenza virus type 3," J. Virol., 1997, vol. 71, No. 6, pp. 4272-4277.
Humphrey et al. "VMD: visual molecular dynamics," Journal of Molecular Graphics, 1996, vol. 14, No. 1, pp. 33-38, 27-38 (Abstract Only).
Johnson et al. "The G glycoprotein of human respiratory syncytial viruses of subgroups A and B: Extensive sequence divergence between antigenically related proteins," PNAS, Aug. 1987, vol. 84, pp. 5625-5629.
Juhasz et al. "The two amino acid substitutions in the L protein of cpts530/1009, a live-attenuated respiratory syncytial virus candidate vaccine, are independent temperature-sensitive and attenuation mutations," Vaccine, 1999, vol. 17, No. 11-12, pp. 1416-1424.
Karron et al. "Respiratory syncytial virus (RSV) SH and G proteins are not essential for viral replication in vitro: Clinical evaluation and molecular characterization of a cold-passaged, attenuated RSV subgroup B mutant," Proc. Natl. Acad. Sci. USA, 1997, vol. 94, pp. 13961-13966.
Karron et al. "A gene deletion that up-regulates viral gene expression yields an attenuated RSV vaccine with improved antibody responses in children," Science Transl. Med., 2015, vol. 7, No. 312, pp. 312ra175.
Kato et al. "The paramyxovirus, Sendai virus, V protein encodes a luxury function required for viral pathogenesis," The EMBO. Journal, 1997, vol. 16, pp. 578-587.
Kunec et al. "Codon Pair Bias Is a Direct Consequence of Dinucleotide Bias," Cell reports, Jan. 2016, vol. 14, No. 1, pp. 55-67.
Lauring et al. "Rationalizing the development of live attenuated virus vaccines," Nature Biotechnology, 2010, vol. 28, No. 6, pp. 573-579.
Lee et al. "Complete Genome Sequence of Human Respiratory Syncytial Virus Genotype A with a 72-Nucleotide Duplication in the Attachment Protein G Gene," Journal of Virology, Dec. 2012, vol. 86, No. 24, pp. 13810-13811.

(56) References Cited

OTHER PUBLICATIONS

Le Nouen et al. "Attenuation of human respiratory syncytial virus by genome-scale codon-pair deoptimization," PNAS, Sep. 2014, vol. 111, No. 36, pp. 13169-13174.
Liang eta l. "Enhanced Neutralizing Antibody Response Induced by Respiratory Syncytial Virus Pre-fusion F Protein Expressed by a Vaccine Candidate," J. Virol., 2015, vol. 89, pp. 9499-9510.
Luongo et al. "Increased Genetic and Phenotypic Stability of a Promising Live-Attenuated Respiratory Syncytial Virus Vaccine Candidate by Reverse Genetics," J. Virol., 2012, vol. 86, No. 19, pp. 10792-10804.
Luongo eta l. "Respiratory Syncytial Virus Modified by Deletions of the NS2 Gene and Amino Acid S1313 of the L Polymerase Protein Is a Temperature-Sensitive, Live-Attenuated Vaccine Candidate That Is Phenotypically Stable at Physiological Temperature," J. Virol., 2013, vol. 87, No. 4, pp. 1985-1996.
Martinez et al. "Synonymous Virus Genome Recoding as a Tool to Impact Viral Fitness," Trends in Microbiology, Feb. 2016, vol. 24, No. 2, pp. 134-147 (Abstract Only).
Mason et al. "Interaction between human respiratory syncytial virus (RSV) M2-1 and P proteins is required for reconstitution of M2-1-dependent RSV minigenome activity," J. Virol., 2003, vol. 77, No. 19, pp. 10670-10676.
McLellan et al. "Structure of RSV Fusion Glycoprotein Trimer Bound to a Prefusion-Specific Neutralizing Antibody," Science, 2013, vol. 340, No. 6136, pp. 1113-1117.
McLellan et al."Structure-Based Design of a Fusion Glycoprotein Vaccine for Respiratory Syncytial Virus," Science, 2013, vol. 342, No. 6158, pp. 592-598.
Meng et al. "Refining the balance of attenuation and immunogenicity of respiratory syncytial virus by targeted codon deoptimization of virulence genes," Mbio., 2014, vol. 5, No. 5, pp. e01704-e01714.
Mink et al. "Nucleotide sequences of the 3' leader and 5' trailer regions of human respiratory syncytial virus genomic RNA," Virology, 1991, vol. 185, No. 2, pp. 615-624 (Abstract Only).
Mueller et al. "Reduction of the Rate of Poliovirus Protein Synthesis through Large-Scale Codon Deoptimization Causes Attenuation of Viral Virulence by Lowering Specific Infectivity," Journal of Virology, Oct. 2006, vol. 80, No. 19, pp. 9687-9696.
Mueller et al. "Live attenuated influenza virus vaccines by computer-aided rational design," Nature Biotechnology, Jul. 2010, vol. 28, No. 7, pp. 723-727.
Ni et al. "Computer-aided codon-pairs deoptimization of the major envelope GP5 gene attenuates porcine reproductive and respiratory syndrome virus," Virology, 2014, vol. 450-451, pp. 132-139.
Nielsen "Molecular signatures of natural selection," Annu. Rev. Genet., 2005, vol. 39, pp. 197-218 (Abstract Only).
Nogales et al. "Influenza A virus attenuation by codon deoptimization of the NS gene for vaccine development," J. Virol., 2014, vol. 88, No. 18, pp. 10525-10540.
Nouen et al. "Genetic stability of genome-scale deoptimized RNA virus vaccine candidates under selective pressure," PNAS, Jan. 2017, vol. 114, No. 3, pp. E386-E395.
Nougairdede et al. "Random codon re-encoding induces stable reduction of replicative fitness of Chikungunya virus in primate and mosquito cells," PLoS Pathog., 2013, vol. 9, No. 2, e1003172.
Phillips et al. "Scalable molecular dynamics with NAMD," Journal of Computational Chemistry, 2005, vol. 26, No. 16, pp. 1781-1802.
Rothberg et al. "An integrated semiconductor device enabling non-optical genome sequencing," Nature, 2011, vol. 475, No. 7356, pp. 348-352.
Samal et al. "RNA replication by a respiratory syncytial virus RNA analog does not obey the rule of six and retains a nonviral trinucleotide extension at the leader end," J. Virol., 1996, vol. 70, pp. 5075-5082.
Shen et al. "Large-scale recoding of an arbovirus genome to rebalance its insect versus mammalian preference," Proc. Natl. Acad. Sci. USA, 2015, vol. 112, No. 15, pp. 4749-4754.
Stec et al. "Sequence analysis of the polymerase L gene of human respiratory syncytial virus and predicted phylogeny of nonsegmented negative-strand viruses." Virology, Jul. 1991, vol. 183, No. 1, pp. 273-287 (Abstract Only).
Teng et al. "Recombinant Respiratory Syncytial Virus That Does Not Express the NS1 or M2-2 Protein Is Highly Attenuated and Immunogenic in Chimpanzees," J. Virol. 2000, vol. 74, No. 19, pp. 9317-9321.
Tanner et al. "Crystal structure of the essential transcription antiterminator M2-1 protein of human respiratory syncytial virus and implications of its phosphorylation," Proc. Natl. Acad. Sci. USA, 2014, vol. 111, No. 4, pp. 1580-1585.
Tran et al. "The respiratory syncytial virus M2-1 protein forms tetramers and interacts with RNA and P in a competitive manner," J. Virol, 2009, vol. 83, No. 13, pp. 6363-6374.
Tulloch et al. "RNA virus attenuation by codon pair deoptimisation is an artefact of increases in CpG/UpA dinucleotide frequencies," eLife, Dec. 2014, 3, e04531, 15 pages.
Vabret et al. "Large-scale nucleotide optimization of simian immunodeficiency virus reduces its capacity to stimulate type I interferon in vitro," J. Virol., 2014, vol. 88, No. 8, pp. 4161-4172.
White et al. "Human body temperature and new approaches to constructing temperature-sensitive bacterial vaccines," Cellular and Molecular Life Sciences: CMLS, Sep. 2011, vol. 68, No. 18, pp. 3019-3031.
Whitehead et al. "Recombinant Respiratory Syncytial Virus (RSV) Bearing a Set of Mutations from Cold-Passaged RSV Is Attenuated in Chimpanzees," J. Virol., 1998, vol. 72, No. 5, pp. 4467-4471.
Whitehead et al. "Addition of a Missense Mutation Present in the L Gene of Respiratory Syncytial Virus (RSV) cpts530/1030 to RSV Vaccine Candidate cpts248/404 Increases Its Attenuation and Temperature Sensitivity," J. Virol., 1999, vol. 73, No. 2, pp. 871-877.
Whitehead et al. "A Single Nucleotide Substitution in the Transcription Start Signal of the M2 Gene of Respiratory Syncytial Virus Vaccine Candidatecpts248/404 Is the Major Determinant of the Temperature-Sensitive and Attenuation Phenotypes," Virology, 1998, vol. 247, No. 2, pp. 232-239.
Whitehead et al. "Recombinant Respiratory Syncytial Virus Bearing a Deletion of either the NS2 or SH Gene Is Attenuated in Chimpanzees," J. Virol. 1999, vol. 73, No. 4, pp. 3438-3442.
Wright et al. "The absence of enhanced disease with wild type respiratory syncytial virus infection occurring after receipt of live, attenuated, respiratory syncytial virus vaccines," Vaccine, 2007, vol. 25, No. 42, pp. 7372-7378.
Wyatt et al. "Replication-Deficient Vaccinia Virus Encoding Bacteriophage T7 RNA Polymerase for Transient Gene Expression in Mammalian Cells," Virology, 1995, vol. 210, No. 1, pp. 202-205.
Yang et al. "Deliberate reduction of hemagglutinin and neuraminidase expression of influenza virus leads to a n ultraprotective live vaccine in mice," Proc. Natl. Acad. Sci. USA, 2013, vol. 110, No. 23, pp. 9481-9486.
Yunus et al. "Sequence analysis of a functional polymerase (L) gene of bovine respiratory syncytial virus: determination of minimal trans-acting requirements for RNA replication," Journal of General Virology, Sep. 1998, vol. 79, pp. 2231-2238.
International Search Report and Written Opinion for International (PCT) Patent Application No. PCT/US2017/053047, dated Dec. 14, 2017 14 pages.
International Preliminary Report on Patentability for International (PCT) Patent Application No. PCT/US2017/053047, dated Apr. 4, 2019 7 pages.
Official Action for European Patent Application No. 17778443.6, dated May 19, 2020 4 pages.
Official Action for U.S. Appl. No. 16/335,099, dated Feb. 14, 2020 9 pages Restriction Requirement.
Notice of Allowance for U.S. Appl. No. 16/335,099, dated Jun. 10, 2020 8 pages.

* cited by examiner

>NS1_WT
MGSNSLSMIKVRLQNLFDNDEVALLKITCYTDKLIHLTNALAKAVIHTIKLNGIVFVHVITSSDICPNN
NIVVKSNFTTMPVLQNGGYIWEMMELTHCSQPNGLLDDNCEIKFSKKLSDSTMTNYMNQLSELL
GFDLNP

>NS2_WT
MDTTHNDNTPQRLMITDMRPLSLETIITSLTRDIITHKFIYLINHECIVRKLDERQATFTFLVNYEMKL
LHKVGSTKYKKYTEYNTKYGTFPMPIFINHDGFLECIGIKPTKHTPIIYKYDLNP

>N_WT
MALSKVKLNDTLNKDQLLSSSKYTIQRSTGDSIDTPNYDVQKHINKLCGMLLITEDANHKFTGLIG
MLYAMSRLGREDTIKILRDAGYHVKANGVDVTTHRQDINGKEMKFEVLTLASLTTEIQINIEIESRK
SYKKMLKEMGEVAPEYRHDSPDCGMIILCIAALVITKLAAGDRSGLTAVIRRANNVLKNEMKRYK
GLLPKDIANSFYEVFEKHPHFIDVFVHFGIAQSSTRGGSRVEGIFAGLFMNAYGAGQVMLRWGVL
AKSVKNIMLGHASVQAEMEQVVEVYEYAQKLGGEAGFYHILNNPKASLLSLTQFPHFSSVVLGN
AAGLGIMGEYRGTPRNQDLYDAAKAYAEQLKENGVINYSVLDLTAEELEAIKHQLNPKDNDVEL

>P_WT
MEKFAPEFHGEDANNRATKFLESIKGKFTSPKDPKKKDSIISVNSIDIEVTKESPITSNSTIINPTNE
TDDTAGNKPNYQRKPLVSFKEDPTPSDNPFSKLYKETIETFDNNEEESSYSYEEINDQTNDNITA
RLDRIDEKLSEILGMLHTLVVASAGPTSARDGIRDAMVGLREEMIEKIRTEALMTNDRLEAMARLR
NEESEKMAKDTSDEVSLNPTSEKLNNLLEGNDSDNDLSLEDF

>M_WT
METYVNKLHEGSTYTAAVQYNVLEKDDDPASLTIWVPMFQSSMPADLLIKELANVNILVKQISTPK
GPSLRVMINSRSAVLAQMPSKFTICANVSLDERSKLAYDVTTPCEIKACSLTCLKSKNMLTTVKDL
TMKTLNPTHDIIALCEFENIVTSKKVIIPTYLRSISVRNKDLNTLENITTTEFKNAITNAKIIPYSGLLLVI
TVTDNKGAFKYIKPQSQFIVDLGAYLEKESIYYVTTNWKHTATRFAIKPMED

>SH_WT
MENTSITIEFSSKFWPYFTLIHMITTIISLLIIISIMIAILNKLCEYNVFHNKTFELPRARVNT

>G_WT
MSKNKDQRTAKTLERTWDTLNHLLFISSCLYKLNLKSVAQITLSILAMIISTSLIIAAIIFIASANHKVT
PTTAIIQDATSQIKNTTPTYLTQNPQLGISPSNPSEITSQITTILASTTPGVKSTLQSTTVKTKNTTTT
QTQPSKPTTKQRQNKPPSKPNNDFHFEVFNFVPCSICSNNPTCWAICKRIPNKKPGKKTTTKPTK
KPTLKTTKKDPKPQTTKSKEVPTTKPTEEPTINTTKTNIITTLLTSNTTGNPELTSQMETFHSTSSE
GNPSPSQVSTTSEYPSQPSSPPNTPRQ

>F_WT
MELLILKANAITTILTAVTFCFASGQNITEEFYQSTCSAVSKGYLSALRTGWYTSVITIELSNIKKNK
CNGTDAKVKLIKQELDKYKNAVTELQLLMQSTQATNNRARRELPRFMNYTLNNAKKTNVTLSKK
RKRRFLGFLLGVGSAIASGVAVSKVLHLEGEVNKIKSALLSTNKAVVSLSNGVSVLTSKVLDLKNY
IDKQLLPIVNKQSCSISNIETVIEFQQKNNRLLEITREFSVNAGVTTPVSTYMLTNSELLSLINDMPIT
NDQKKLMSNNVQIVRQQSYSIMSIIKEEVLAYVVQLPLYGVIDTPCWKLHTSPLCTTNTKEGSNIC
LTRTDRGWYCDNAGSVSFFPQAETCKVQSNRVFCDTMNSLTLPSEVNLCNVDIFNPKYDCKIMT
SKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNAGKSTTNIMITTIII
VIIVILLSLIAVGLLLYCKARSTPVTLSKDQLSGINNIAFSN

FIG. 13 (continued)

>M2-1
MSRRNPCKFEIRGHCLNGKRCHFSHNYFEWPPHALLVRQNFMLNRILKSMDKSIDTLSEISGAAE
LDRTEEYALGVVGVLESYIGSINNITKQSACVAMSKLLTELNSDDIKKLRDNEELNSPKIRVYNTVI
SYIESNRKNNKQTIHLLKRLPADVLKKTIKNTLDIHKSITINNPKESTVSDTNDHAKNNDTT

>M2-2
MTMPKIMILPDKYPCSITSILITSRCRVTMYNQKNTLYFNQNNPNNHMYSPNQTFNEIHWTSQELI
DTIQNFLQHLGIIEDIYTIYILVS

>L_WT
MDPIINGNSANVYLTDSYLKGVISFSECNALGSYIFNGPYLKNDYTNLISRQNPLIEHMNLKKLNIT
QSLISKYHKGEIKLEEPTYFQSLLMTYKSMTSSEQIATTNLLKKIIRRAIEISDVKVYAILNKLGLKEK
DKIKSNNGQDEDNSVITTIIKDDILSAVKDNQSHLKADKNHSTKQKDTIKTTLLKKLMCSMQHPPS
WLIHWFNLYTKLNNILTQYRSNEVKNHGFTLIDNQTLSGFQFILNQYGCIVYHKELKRITVTTYNQF
LTWKDISLSRLNVCLITWISNCLNTLNKSLGLRCGFNNVILTQLFLYGDCILKLFHNEGFYIIKEVEG
FIMSLILNITEEDQFRKRFYNSMLNNITDAANKAQKNLLSRVCHTLLDKTVSDNIINGRWIILLSKFL
KLIKLAGDNNLNNLSELYFLFRIFGHPMVDERQAMDAVKINCNETKFYLLSSLSMLRGAFIYRIIKG
FVNNYNRWPTLRNAIVLPLRWLTYYKLNTYPSLLELTERDLIVLSGLRFYREFRLPKKVDLEMIIND
KAISPPKNLIWTSFPRNYMPSHIQNYIEHEKLKFSESDKSRRVLEYYLRDNKFNECDLYNCVVNQ
SYLNNPNHVVSLTGKERELSVGRMFAMQPGMFRQVQILAEKMIAENILQFFPESLTRYGDLELQK
ILELKAGISNKSNRYNDNYNNYISKCSIITDLSKFNQAFRYETSCICSDVLDELHGVQSLFSWLHLTI
PHVTIICTYRHAPPYIGDHIVDLNNVDEQSGLYRYHMGGIEGWCQKLWTIEAISLLDLISLKGKFSIT
ALINGDNQSIDISKPIRLMEGQTHAQADYLLALNSLKLLYKEYAGIGHKLKGTETYISRDMQFMSKT
IQHNGVYYPASIKKVLRVGPWINTILDDFKVSLESIGSLTQELEYRGESLLCSLIFRNVWLYNQIAL
QLKNHALCNNKLYLDILKVLKHLKTFFNLDNIDTALTLYMNLPMLFGGGDPNLLYRSFYRRTPDFL
TEAIVHSVFILSYYTNHDLKDKLQDLSDDRLNKFLTCIITFDKNPNAEFVTLMRDPQALGSERQAKI
TSEINRLAVTEVLSTAPNKIFSKSAQHYTTTEIDLNDIMQNIEPTYPHGLRVVYESLPFYKAEKIVNL
ISGTKSITNILEKTSAIDLTDIDRATEMMRKNITLLIRILPLDCNRDKREILSMENLSITELSKYVRERS
WSLSNIVGVTSPSIMYTMDIKYTTSTISSGIIIEKYNVNSLTRGERGPTKPWVGSSTQEKKTMPVY
NRQVLTKKQRDQIDLLAKLDWVYASIDNKDEFMEELSIGTLGLTYEKAKKLFPQYLSVNYLHRLTV
SSRPCEFPASIPAYRTTNYHFDTSPINRILTEKYGDEDIDIVFQNCISFGLSLMSVVEQFTNVCPNR
IILIPKLNEIHLMKPPIFTGDVDIHKLKQVIQKQHMFLPDKISLTQYVELFLSNKTLKSGSHVNSNLIL
AHKISDYFHNTYILSTNLAGHWILIIQLMKDSKGIFEKDWGEGYITDHMFINLKVFFNAYKTYLLCFH
KGYGKAKLECDMNTSDLLCVLELIDSSYWKSMSKVFLEQKVIKYILSQDASLHRVKGCHSFKLWF
LKRLNVAEFTVCPWVVNIDYHPTHMKAILTYIDLVRMGLINIDRIHIKNKHKFNDEFYTSNLFYINYN
FSDNTHLLTKHIRIANSELENNYNKLYHPTPETLENILANPIKSNDKKTLNDYCIGKNVDSIMLPLLS
NKKLIKSSAMIRTNYSKQDLYNLFPMVVIDRIIDHSGNTAKSNQLYTTTSHQISLVHNSTSLYCMLP
WHHINRFNFVFSSTGCKISIEYILKDLKIKDPNCIAFIGEGAGNLLLRTVVELHPDIRYIYRSLKDCN
DHSLPIEFLRLYNGHINIDYGENLTIPATDATNNIHWSYLHIKFAEPISLFVCDAELSVTVNWSKIIIE
WSKHVRKCKYCSSVNKCMLIVKYHAQDDIDFKLDNITILKTYVCLGSKLKGSEVYLVLTIGPANIFP
VFNVVQNAKLILSRTKNFIMPKKADKESIDANIKSLIPFLCYPITKKGINTALSKLKSVVSGDILSYSIA
GRNEVFSNKLINHKHMNILKWFNHVLNFRSTELNYNHLYMVESTYPYLSELLNSLTTNELKKLIKIT
GSLLYNFHNE

FIG. 14

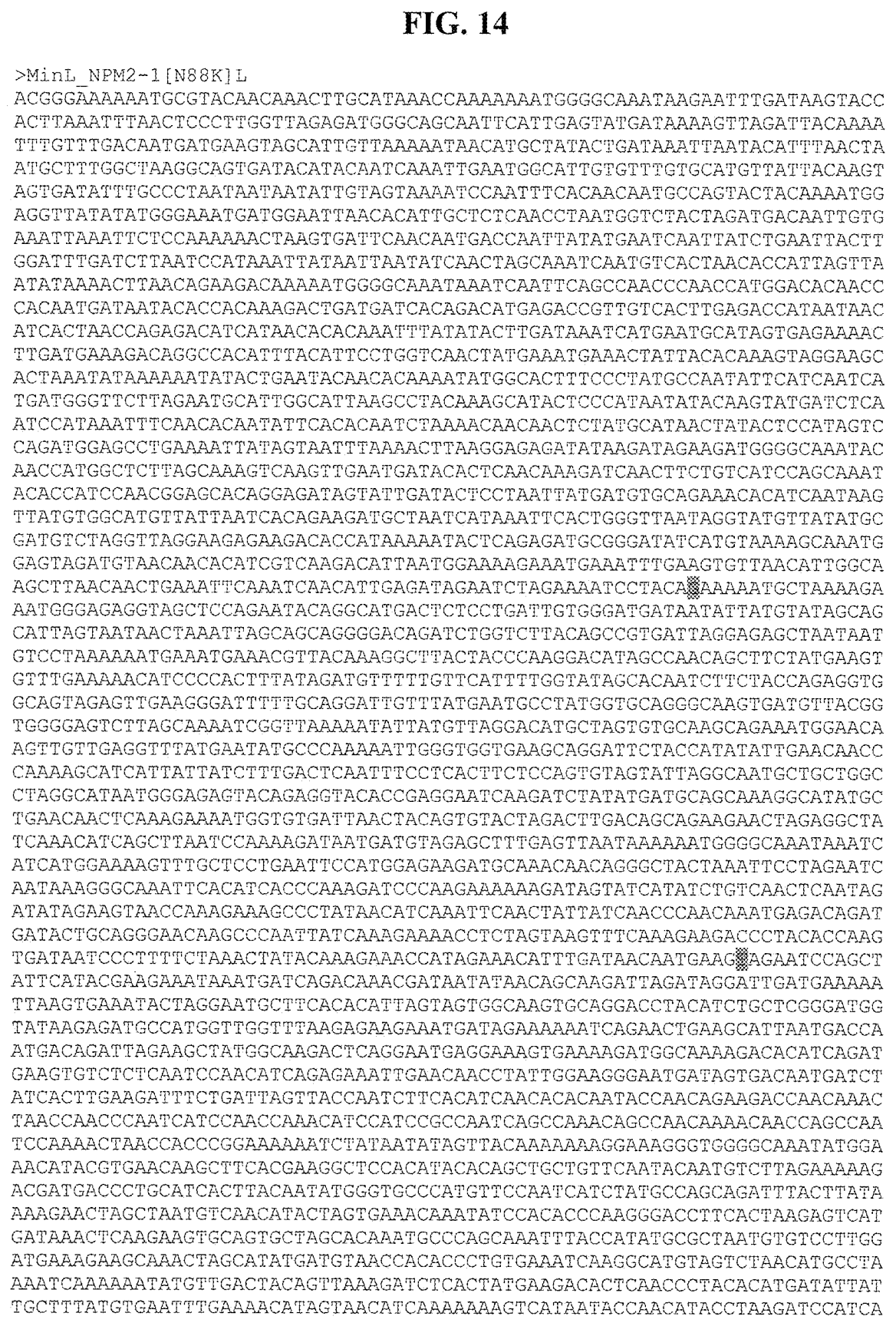

```
>MinL_NPM2-1[N88K]L
ACGGGAAAAAATGCGTACAACAAACTTGCATAAACCAAAAAAATGGGGCAAATAAGAATTTGATAAGTACC
ACTTAAATTTAACTCCCTTGGTTAGAGATGGGCAGCAATTCATTGAGTATGATAAAAGTTAGATTACAAAA
TTTGTTTGACAATGATGAAGTAGCATTGTTAAAAATAACATGCTATACTGATAAATTAATACATTTAACTA
ATGCTTTGGCTAAGGCAGTGATACATACAATCAAATTGAATGGCATTGTGTTTGTGCATGTTATTACAAGT
AGTGATATTTGCCCTAATAATAATATTGTAGTAAAATCCAATTTCACAACAATGCCAGTACTACAAAATGG
AGGTTATATATGGGAAATGATGGAATTAACACATTGCTCTCAACCTAATGGTCTACTAGATGACAATTGTG
AAATTAAATTCTCCAAAAAACTAAGTGATTCAACAATGACCAATTATATGAATCAATTATCTGAATTACTT
GGATTTGATCTTAATCCATAAATTATAATTAATATCAACTAGCAAATCAATGTCACTAACACCATTAGTTA
ATATAAAACTTAACAGAAGACAAAAATGGGGCAAATAAATCAATTCAGCCAACCCAACCATGGACACAACC
CACAATGATAATACACCACAAAGACTGATGATCACAGACATGAGACCGTTGTCACTTGAGACCATAATAAC
ATCACTAACCAGAGACATCATAACACACAAATTTATATACTTGATAAATCATGAATGCATAGTGAGAAAAC
TTGATGAAAGACAGGCCACATTTACATTCCTGGTCAACTATGAAATGAAACTATTACACAAAGTAGGAAGC
ACTAAATATAAAAAATATACTGAATACAACACAAAATATGGCACTTTCCCTATGCCAATATTCATCAATCA
TGATGGGTTCTTAGAATGCATTGGCATTAAGCCTACAAAGCATACTCCCATAATATACAAGTATGATCTCA
ATCCATAAATTTCAACACAATATTCACACAATCTAAAACAACAACTCTATGCATAACTATACTCCATAGTC
CAGATGGAGCCTGAAAATTATAGTAATTTAAAACTTAAGGAGAGATATAAGATAGAAGATGGGGCAAATAC
AACCATGGCTCTTAGCAAAGTCAAGTTGAATGATACACTCAACAAAGATCAACTTCTGTCATCCAGCAAAT
ACACCATCCAACGGAGCACAGGAGATAGTATTGATACTCCTAATTATGATGTGCAGAAACACATCAATAAG
TTATGTGGCATGTTATTAATCACAGAAGATGCTAATCATAAATTCACTGGGTTAATAGGTATGTTATATGC
GATGTCTAGGTTAGGAAGAGAAGACACCATAAAAATACTCAGAGATGCGGGATATCATGTAAAAGCAAATG
GAGTAGATGTAACAACACATCGTCAAGACATTAATGGAAAAGAAATGAAATTTGAAGTGTTAACATTGGCA
AGCTTAACAACTGAAATTCAAATCAACATTGAGATAGAATCTAGAAAATCCTACA[illegible]AAAAATGCTAAAAGA
AATGGGAGAGGTAGCTCCAGAATACAGGCATGACTCTCCTGATTGTGGGATGATAATATTATGTATAGCAG
CATTAGTAATAACTAAATTAGCAGCAGGGGACAGATCTGGTCTTACAGCCGTGATTAGGAGAGCTAATAAT
GTCCTAAAAAATGAAATGAAACGTTACAAAGGCTTACTACCCAAGGACATAGCCAACAGCTTCTATGAAGT
GTTTGAAAAACATCCCCACTTTATAGATGTTTTTGTTCATTTTGGTATAGCACAATCTTCTACCAGAGGTG
GCAGTAGAGTTGAAGGGATTTTTGCAGGATTGTTTATGAATGCCTATGGTGCAGGGCAAGTGATGTTACGG
TGGGGAGTCTTAGCAAAATCGGTTAAAAATATTATGTTAGGACATGCTAGTGTGCAAGCAGAAATGGAACA
AGTTGTTGAGGTTTATGAATATGCCCAAAAATTGGGTGGTGAAGCAGGATTCTACCATATATTGAACAACC
CAAAAGCATCATTATTATCTTTGACTCAATTTCCTCACTTCTCCAGTGTAGTATTAGGCAATGCTGCTGGC
CTAGGCATAATGGGAGAGTACAGAGGTACACCGAGGAATCAAGATCTATATGATGCAGCAAAGGCATATGC
TGAACAACTCAAAGAAAATGGTGTGATTAACTACAGTGTACTAGACTTGACAGCAGAAGAACTAGAGGCTA
TCAAACATCAGCTTAATCCAAAAGATAATGATGTAGAGCTTTGAGTTAATAAAAAATGGGGCAAATAAATC
ATCATGGAAAAGTTTGCTCCTGAATTCCATGGAGAAGATGCAAACAACAGGGCTACTAAATTCCTAGAATC
AATAAAGGGCAAATTCACATCACCCAAAGATCCCAAGAAAAAAGATAGTATCATATCTGTCAACTCAATAG
ATATAGAAGTAACCAAAGAAAGCCCTATAACATCAAATTCAACTATTATCAACCCAACAAATGAGACAGAT
GATACTGCAGGGAACAAGCCCAATTATCAAAGAAAACCTCTAGTAAGTTTCAAAGAAGACCCTACACCAAG
TGATAATCCCTTTTCTAAACTATACAAAGAAACCATAGAAACATTTGATAACAATGAAG[illegible]AGAATCCAGCT
ATTCATACGAAGAAATAAATGATCAGACAAACGATAATATAACAGCAAGATTAGATAGGATTGATGAAAAA
TTAAGTGAAATACTAGGAATGCTTCACACATTAGTAGTGGCAAGTGCAGGACCTACATCTGCTCGGGATGG
TATAAGAGATGCCATGGTTGGTTTAAGAGAAGAAATGATAGAAAAAATCAGAACTGAAGCATTAATGACCA
ATGACAGATTAGAAGCTATGGCAAGACTCAGGAATGAGGAAAGTGAAAAGATGGCAAAAGACACATCAGAT
GAAGTGTCTCTCAATCCAACATCAGAGAAATTGAACAACCTATTGGAAGGGAATGATAGTGACAATGATCT
ATCACTTGAAGATTTCTGATTAGTTACCAATCTTCACATCAACACACAATACCAACAGAAGACCAACAAAC
TAACCAACCCAATCATCCAACCAAACATCCATCCGCCAATCAGCCAAACAGCCAACAAAACAACCAGCCAA
TCCAAAACTAACCACCCGGAAAAAATCTATAATATAGTTACAAAAAAAGGAAAGGGTGGGGCAAATATGGA
AACATACGTGAACAAGCTTCACGAAGGCTCCACATACACAGCTGCTGTTCAATACAATGTCTTAGAAAAAG
ACGATGACCCTGCATCACTTACAATATGGGTGCCCATGTTCCAATCATCTATGCCAGCAGATTTACTTATA
AAAGAACTAGCTAATGTCAACATACTAGTGAAACAAATATCCACACCCAAGGGACCTTCACTAAGAGTCAT
GATAAACTCAAGAAGTGCAGTGCTAGCACAAATGCCCAGCAAATTTACCATATGCGCTAATGTGTCCTTGG
ATGAAAGAAGCAAACTAGCATATGATGTAACCACACCCTGTGAAATCAAGGCATGTAGTCTAACATGCCTA
AAATCAAAAAATATGTTGACTACAGTTAAAGATCTCACTATGAAGACACTCAACCCTACACATGATATTAT
TGCTTTATGTGAATTTGAAAACATAGTAACATCAAAAAAAGTCATAATACCAACATACCTAAGATCCATCA
```

FIG 14 (continued)

GTGTCAGAAATAAAGATCTGAACACACTTGAAAATATAACAACCACTGAATTCAAAAATGCTATCACAAAT
GCAAAAATCATCCCTTACTCAGGATTACTATTAGTCATCACAGTGACTGACAACAAAGGAGCATTCAAATA
CATAAAGCCACAAAGTCAATTCATAGTAGATCTTGGAGCTTACCTAGAAAAAGAAAGTATATATTATGTTA
CCACAAATTGGAAGCACACAGCTACACGATTTGCAATCAAACCCATGGAAGATTAACCTTTTTCCTCTACA
TCAGTGTGTTAATTCATACAAACTTTCTACCTACATTCTTCACTTCACCATCACAATCACAAACACTCTGT
GGTTCAACCAATCAAACAAAACTTATCTGAAGTCCCAGATCATCCCAAGTCATTGTTTATCAGATCTAGTA
CTCAAATAAGTTAATAAAAAATATACACATGGGGCAAATAATCATTGGAGGAAATCCAACTAATCACAATA
TCTGTTAACATAGACAAGTCCACACACCATACAGAATCAACCAATGGAAAATACATCCATAACAATAGAAT
TCTCAAGCAAATTCTGGCCTTACTTTACACTAATACACATGATCACAACAATAATCTCTTTGCTAATCATA
ATCTCCATCATGATTGCAATACTAAACAAACTTTGTGAATATAACGTATTCCATAACAAAACCTTTGAGTT
ACCAAGAGCTCGAGTTAATACTTGATAAAGTAGTTAATTAAAAATAGTCATAACAATGAACTAGGATATCA
AGACTAACAATAACATTGGGGCAAATGCAAACATGTCCAAAAACAAGGACCAACGCACCGCTAAGACATTA
GAAAGGACCTGGGACACTCTCAATCATTTATTATTCATATCATCGTGCTTATATAAGTTAAATCTTAAATC
TGTAGCACAAATCACATTATCCATTCTGGCAATGATAATCTCAACTTCACTTATAATTGCAGCCATCATAT
TCATAGCCTCGGCAAACCACAAAGTCACACCAACAACTGCAATCATACAAGATGCAACAAGCCAGATCAAG
AACACAACCCCAACATACCTCACCCAGAATCCTCAGCTTGGAATCAGTCCCTCTAATCCGTCTGAAATTAC
ATCACAAATCACCACCATACTAGCTTCAACAACACCAGGAGTCAAGTCAACCCTGCAATCCACAACAGTCA
AGACCAAAAACACAACAACAACTCAAACACAACCCAGCAAGCCCACCACAAAACAACGCCAAAACAAACCA
CCAAGCAAACCCAATAATGATTTTCACTTTGAAGTGTTCAACTTTGTACCCTGCAGCATATGCAGCAACAA
TCCAACCTGCTGGGCTATCTGCAAAAGAATACCAAACAAAAAACCAGGAAAGAAAACCACTACCAAGCCCA
CAAAAAAACCAACCCTCAAGACAACCAAAAAAGATCCCAAACCTCAAACCACTAAATCAAAGGAAGTACCC
ACCACCAAGCCCACAGAAGAGCCAACCATCAACACCACCAAAACAAACATCATAACTACACTACTCACCTC
CAACACCACAGGAAATCCAGAACTCACAAGTCAAATGGAAACCTTCCACTCAACTTCCTCCGAAGGCAATC
CAAGCCCTTCTCAAGTCTCTACAACATCCGAGTACCCATCACAACCTTCATCTCCACCCAACACACCACGC
CAGTAGTTACTTAAAAACATATTATCACAAAAGGCCTTGACCAACTTAAACAGAATCAAAATAAACTCTGG
GGCAAATAACAATGGAGTTGCTAATCCTCAAAGCAAATGCAATTACCACAATCCTCACTGCAGTCACATTT
TGTTTTGCTTCTGGTCAAAACATCACTGAAGAATTTTATCAATCAACATGCAGTGCAGTTAGCAAAGGCTA
TCTTAGTGCTCTGAGAACTGGTTGGTATACCAGTGTTATAACTATAGAATTAAGTAATATCAAGAAAAATA
AGTGTAATGGAACAGATGCTAAGGTAAAATTGATAAAACAAGAATTAGATAAATATAAAAATGCTGTAACA
GAATTGCAGTTGCTCATGCAAAGCACACAAGCAACAAACAATCGAGCCAGAAGAGAACTACCAAGGTTTAT
GAATTATACACTCAACAATGCCAAAAAAACCAATGTAACATTAAGCAAGAAAAGGAAAAGAAGATTTCTTG
GTTTTTTGTTAGGTGTTGGATCTGCAATCGCCAGTGGCGTTGCTGTATCTAAGGTCCTGCACCTAGAAGGG
GAAGTGAACAAGATCAAAAGTGCTCTACTATCCACAAACAAGGCTGTAGTCAGCTTATCAAATGGAGTTAG
TGTTTTAACCAGCAAAGTGTTAGACCTCAAAAACTATATAGATAAACAATTGTTACCTATTGTGAACAAGC
AAAGCTGCAGCATATCAAATATAGAAACTGTGATAGAGTTCCAACAAAAGAACAACAGACTACTAGAGATT
ACCAGGGAATTTAGTGTTAATGCAGGCGTAACTACACCTGTAAGCACTTACATGTTAACTAATAGTGAATT
ATTGTCATTAATCAATGATATGCCTATAACAAATGATCAGAAAAAGTTAATGTCCAACAATGTTCAAATAG
TTAGACAGCAAAGTTACTCTATCATGTCCATAATAAAAGAGGAAGTCTTAGCATATGTAGTACAATTACCA
CTATATGGTGTTATAGATACACCCTGTTGGAAACTACACACATCCCCTCTATGTACAACCAACACAAAAGA
AGGGTCCAACATCTGTTTAACAAGAACTGACAGAGGATGGTACTGTGACAATGCAGGATCAGTATCTTTCT
TCCCACAAGCTGAAACATGTAAAGTTCAATCAAATCGAGTATTTTGTGACACAATGAACAGTTTAACATTA
CCAAGTGAAGTAAATCTCTGCAATGTTGACATATTCAACCCCAAATATGATTGTAAAATTATGACTTCAAA
AACAGATGTAAGCAGCTCCGTTATCACATCTCTAGGAGCCATTGTGTCATGCTATGGCAAAACTAAATGTA
CAGCATCCAATAAAAATCGTGGAATCATAAAGACATTTTCTAACGGGTGCGATTATGTATCAAATAAAGGG
GTGGACACTGTGTCTGTAGGTAACACATTATATTATGTAAATAAGCAAGAAGGTAAAAGTCTCTATGTAAA
AGGTGAACCAATAATAAATTTCTATGACCCATTAGTATTCCCCTCTGATGAATTTGATGCATCAATATCTC
AAGTCAACGAGAAGATTAACCAGAGCCTAGCATTTATTCGTAAATCCGATGAATTATTACATAATGTAAAT
GCTGGTAAATCCACCACAAATATCATGATAACTACTATAATTATAGTGATTATAGTAATATTGTTATCATT
AATTGCTGTTGGACTGCTCTTATACTGTAAGGCCAGAAGCACACCAGTCACACTAAGCAAAGATCAACTGA
GTGGTATAAATAATATTGCATTTAGTAACTAAATAAAAATAGCACCTAATCATGTTCTTACAATGGTTTAC
TATCTGCTCATAGACAACCCATCTGTCATTGGATTTTCTTAAAATCTGAACTTCATCGAAACTCTCATCTA
TAAACCATCTCACTTACACTATTTAAGTAGATTCCTAGTTTATAGTTATATAAAACACAATTGCATGCCAG
ATTAACTTACCATCTGTAAAAATGAAAACTGGGGCAAATATGTCACGAAGGAATCCTTGCAAATTTGAAAT
TCGAGGTCATTGCTTAAATGGTAAGAGGTGTCATTTTAGTCATAATTATTTTGAATGGCCACCCCATGCAC
TGCTTGTAAGACAAAACTTTATGTTAAACAGAATACTTAAGTCTATGGATAAAAGTATAGATACCTTATCA

FIG 14 (continued)

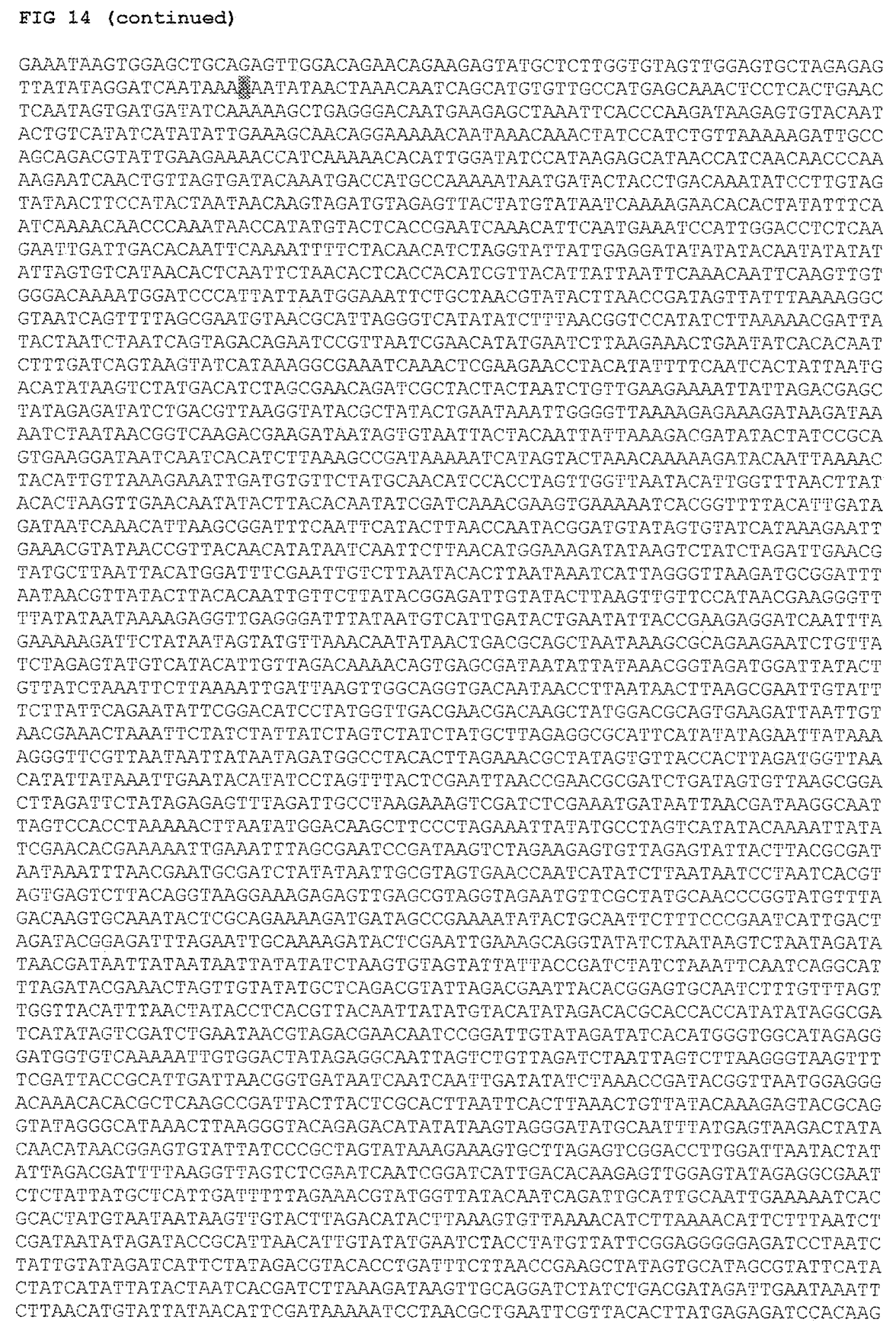

GAAATAAGTGGAGCTGCAGAGTTGGACAGAACAGAAGAGTATGCTCTTGGTGTAGTTGGAGTGCTAGAGAG
TTATATAGGATCAATAAA[illegible]AATATAACTAAACAATCAGCATGTGTTGCCATGAGCAAACTCCTCACTGAAC
TCAATAGTGATGATATCAAAAAGCTGAGGGACAATGAAGAGCTAAATTCACCCAAGATAAGAGTGTACAAT
ACTGTCATATCATATATTGAAAGCAACAGGAAAAACAATAAACAAACTATCCATCTGTTAAAAAGATTGCC
AGCAGACGTATTGAAGAAAACCATCAAAAACACATTGGATATCCATAAGAGCATAACCATCAACAACCCAA
AAGAATCAACTGTTAGTGATACAAATGACCATGCCAAAAATAATGATACTACCTGACAAATATCCTTGTAG
TATAACTTCCATACTAATAACAAGTAGATGTAGAGTTACTATGTATAATCAAAAGAACACACTATATTTCA
ATCAAAACAACCCAAATAACCATATGTACTCACCGAATCAAACATTCAATGAAATCCATTGGACCTCTCAA
GAATTGATTGACACAATTCAAAATTTTCTACAACATCTAGGTATTATTGAGGATATATATACAATATATAT
ATTAGTGTCATAACACTCAATTCTAACACTCACCACATCGTTACATTATTAATTCAAACAATTCAAGTTGT
GGGACAAAATGGATCCCATTATTAATGGAAATTCTGCTAACGTATACTTAACCGATAGTTATTTAAAAGGC
GTAATCAGTTTTAGCGAATGTAACGCATTAGGGTCATATATCTTTAACGGTCCATATCTTAAAAACGATTA
TACTAATCTAATCAGTAGACAGAATCCGTTAATCGAACATATGAATCTTAAGAAACTGAATATCACACAAT
CTTTGATCAGTAAGTATCATAAAGGCGAAATCAAACTCGAAGAACCTACATATTTTCAATCACTATTAATG
ACATATAAGTCTATGACATCTAGCGAACAGATCGCTACTACTAATCTGTTGAAGAAAATTATTAGACGAGC
TATAGAGATATCTGACGTTAAGGTATACGCTATACTGAATAAATTGGGGTTAAAAGAGAAAGATAAGATAA
AATCTAATAACGGTCAAGACGAAGATAATAGTGTAATTACTACAATTATTAAAGACGATATACTATCCGCA
GTGAAGGATAATCAATCACATCTTAAAGCCGATAAAAATCATAGTACTAAACAAAAAGATACAATTAAAAC
TACATTGTTAAAGAAATTGATGTGTTCTATGCAACATCCACCTAGTTGGTTAATACATTGGTTTAACTTAT
ACACTAAGTTGAACAATATACTTACACAATATCGATCAAACGAAGTGAAAAATCACGGTTTTACATTGATA
GATAATCAAACATTAAGCGGATTTCAATTCATACTTAACCAATACGGATGTATAGTGTATCATAAAGAATT
GAAACGTATAACCGTTACAACATATAATCAATTCTTAACATGGAAAGATATAAGTCTATCTAGATTGAACG
TATGCTTAATTACATGGATTTCGAATTGTCTTAATACACTTAATAAATCATTAGGGTTAAGATGCGGATTT
AATAACGTTATACTTACACAATTGTTCTTATACGGAGATTGTATACTTAAGTTGTTCCATAACGAAGGGTT
TTATATAATAAAAGAGGTTGAGGGATTTATAATGTCATTGATACTGAATATTACCGAAGAGGATCAATTTA
GAAAAAGATTCTATAATAGTATGTTAAACAATATAACTGACGCAGCTAATAAAGCGCAGAAGAATCTGTTA
TCTAGAGTATGTCATACATTGTTAGACAAAACAGTGAGCGATAATATTATAAACGGTAGATGGATTATACT
GTTATCTAAATTCTTAAAATTGATTAAGTTGGCAGGTGACAATAACCTTAATAACTTAAGCGAATTGTATT
TCTTATTCAGAATATTCGGACATCCTATGGTTGACGAACGACAAGCTATGGACGCAGTGAAGATTAATTGT
AACGAAACTAAATTCTATCTATTATCTAGTCTATCTATGCTTAGAGGCGCATTCATATATAGAATTATAAA
AGGGTTCGTTAATAATTATAATAGATGGCCTACACTTAGAAACGCTATAGTGTTACCACTTAGATGGTTAA
CATATTATAAATTGAATACATATCCTAGTTTACTCGAATTAACCGAACGCGATCTGATAGTGTTAAGCGGA
CTTAGATTCTATAGAGAGTTTAGATTGCCTAAGAAAGTCGATCTCGAAATGATAATTAACGATAAGGCAAT
TAGTCCACCTAAAAACTTAATATGGACAAGCTTCCCTAGAAATTATATGCCTAGTCATATACAAAATTATA
TCGAACACGAAAAATTGAAATTTAGCGAATCCGATAAGTCTAGAAGAGTGTTAGAGTATTACTTACGCGAT
AATAAATTTAACGAATGCGATCTATATAATTGCGTAGTGAACCAATCATATCTTAATAATCCTAATCACGT
AGTGAGTCTTACAGGTAAGGAAAGAGAGTTGAGCGTAGGTAGAATGTTCGCTATGCAACCCGGTATGTTTA
GACAAGTGCAAATACTCGCAGAAAAGATGATAGCCGAAAATATACTGCAATTCTTTCCCGAATCATTGACT
AGATACGGAGATTTAGAATTGCAAAAGATACTCGAATTGAAAGCAGGTATATCTAATAAGTCTAATAGATA
TAACGATAATTATAATAATTATATATCTAAGTGTAGTATTATTACCGATCTATCTAAATTCAATCAGGCAT
TTAGATACGAAACTAGTTGTATATGCTCAGACGTATTAGACGAATTACACGGAGTGCAATCTTTGTTTAGT
TGGTTACATTTAACTATACCTCACGTTACAATTATATGTACATATAGACACGCACCACCATATATAGGCGA
TCATATAGTCGATCTGAATAACGTAGACGAACAATCCGGATTGTATAGATATCACATGGGTGGCATAGAGG
GATGGTGTCAAAAATTGTGGACTATAGAGGCAATTAGTCTGTTAGATCTAATTAGTCTTAAGGGTAAGTTT
TCGATTACCGCATTGATTAACGGTGATAATCAATCAATTGATATATCTAAACCGATACGGTTAATGGAGGG
ACAAACACACGCTCAAGCCGATTACTTACTCGCACTTAATTCACTTAAACTGTTATACAAAGAGTACGCAG
GTATAGGGCATAAACTTAAGGGTACAGAGACATATATAAGTAGGGATATGCAATTTATGAGTAAGACTATA
CAACATAACGGAGTGTATTATCCCGCTAGTATAAAGAAAGTGCTTAGAGTCGGACCTTGGATTAATACTAT
ATTAGACGATTTTAAGGTTAGTCTCGAATCAATCGGATCATTGACACAAGAGTTGGAGTATAGAGGCGAAT
CTCTATTATGCTCATTGATTTTTAGAAACGTATGGTTATACAATCAGATTGCATTGCAATTGAAAAATCAC
GCACTATGTAATAATAAGTTGTACTTAGACATACTTAAAGTGTTAAAACATCTTAAAACATTCTTTAATCT
CGATAATATAGATACCGCATTAACATTGTATATGAATCTACCTATGTTATTCGGAGGGGGAGATCCTAATC
TATTGTATAGATCATTCTATAGACGTACACCTGATTTCTTAACCGAAGCTATAGTGCATAGCGTATTCATA
CTATCATATTATACTAATCACGATCTTAAAGATAAGTTGCAGGATCTATCTGACGATAGATTGAATAAATT
CTTAACATGTATTATAACATTCGATAAAAATCCTAACGCTGAATTCGTTACACTTATGAGAGATCCACAAG FIG 14 (continued)

CATTAGGTTCAGAGAGACAGGCTAAAATTACTAGCGAAATTAATAGATTAGCCGTTACCGAAGTGTTAAGT
ACCGCACCTAATAAGATATTCTCTAAATCCGCTCAACATTATACAACAACCGAAATAGATCTTAACGATAT
TATGCAAAATATCGAACCTACATATCCTCACGGATTACGCGTAGTTTACGAATCATTACCATTCTATAAAG
CCGAAAAGATCGTTAACTTAATTAGCGGTACAAAATCAATTACTAATATACTCGAAAAGACTAGCGCAATT
GATTTAACCGATATAGATAGAGCTATCGAAATGATGCGTAAAAATATAACATTACTGATACGTATACTACC
ATTAGATTGTAATAGGGATAAAAGAGAGATACTATCTATGGAGAATCTATCAATTACAGAATTGTCAAAAT
ACGTTAGGGAACGATCATGGTCACTATCTAATATCGTAGGCGTAACTAGTCCTAGTATTATGTATACTATG
GATATTAAGTATACAACTAGTACAATTAGTAGCGGTATAATAATCGAAAAATATAACGTTAATAGTCTAAC
ACGTGGTGAAAGGGGACCTACAAAACCTTGGGTCGGATCTAGTACACAAGAGAAGAAAACTATGCCCGTAT
ATAATAGACAGGTATTGACTAAGAAACAACGAGATCAAATAGATCTATTAGCTAAACTCGATTGGGTATAC
GCTAGTATAGATAATAAAGACGAATTTATGGAAGAGTTGTCAATCGGTACATTAGGGTTAACATACGAAAA
AGCTAAGAAATTGTTCCCACAATATCTATCAGTGAATTATCTACATAGATTGACAGTGAGTAGTAGACCAT
GCGAATTTCCCGCTAGTATACCCGCATATAGAACTACTAATTATCATTTCGATACTAGTCCAATTAATAGA
ATATTAACCGAAAAATACGGAGACGAAGATATAGATATCGTATTCCAAAATTGTATTAGTTTCGGATTGAG
TCTTATGTCCGTAGTCGAACAATTTACTAACGTATGTCCTAATAGGATTATACTGATACCTAAATTGAACG
AAATACATCTTATGAAACCTCCTATTTTTACAGGCGATGTCGATATACACAAATTGAAACAGGTTATACAA
AAACAACATATGTTCTTACCCGATAAGATATCGTTAACGCAATACGTTGAGTTGTTCTTATCAAATAAAAC
ACTTAAATCAGGTAGTCACGTTAATAGTAATCTGATACTCGCACATAAAATTAGCGATTACTTTCATAATA
CATATATATTGAGTACTAACTTAGCCGGACATTGGATACTGATTATACAATTGATGAAAGATAGTAAGGGT
ATATTCGAAAAAGATTGGGGTGAGGGATATATAACCGATCATATGTTTATAAACCTTAAGGTCTTCTTTAA
CGCATATAAAACTTATCTATTATGTTTTCATAAGGGATACGGTAAGGCTAAACTCGAATGCGATATGAATA
CATCCGATCTATTATGCGTACTCGAATTAATTGATAGTAGCTATTGGAAATCTATGAGTAAGGTATTCTTA
GAGCAAAAGGTGATCAAGTATATACTATCTCAAGACGCTAGTTTGCATAGGGTTAAGGGATGTCATAGTTT
TAAATTATGGTTTCTTAAAAGATTGAACGTAGCCGAATTTACAGTATGTCCTTGGGTCGTTAACATAGATT
ATCATCCTACACATATGAAAGCTATACTTACATATATAGATCTAGTGAGAATGGGATTGATTAACATAGAT
AGAATACATATAAAGAATAAACATAAATTTAACGACGAATTCTATACTAGTAATCTATTCTATATAAATTA
TAATTTTTCCGATAATACACATCTATTAACTAAACATATACGTATAGCTAATAGCGAACTCGAAAATAATT
ATAATAAATTGTATCATCCTACACCCGAAACATTAGAGAATATACTCGCTAATCCGATTAAATCTAACGAT
AAGAAAACACTTAACGATTATTGTATAGGTAAAAACGTTGATTCAATTATGTTACCATTACTATCAAATAA
GAAATTGATTAAATCTAGCGCTATGATTAGAACTAATTATAGTAAACAGGATCTATATAACTTATTCCCTA
TGGTCGTAATTGATAGAATTATAGATCATTCCGGTAATACCGCTAAATCTAATCAATTGTATACAACTACT
AGTCATCAAATATCATTAGTGCATAATAGTACTAGTCTATATTGTATGTTACCATGGCATCATATTAATAG
ATTCAATTTCGTTTTTAGTAGTACAGGGTGTAAAATTAGTATAGAGTATATACTTAAAGATCTTAAAATTA
AAGATCCTAATTGTATTGCATTCATAGGCGAAGGCGCAGGTAATCTGTTACTTAGAACAGTAGTCGAATTG
CATCCCGATATTAGATATATATATAGATCACTTAAAGATTGTAACGATCATAGTCTACCAATCGAATTCCT
TAGATTGTATAACGGTCATATAAACATAGATTACGGCGAAAACTTAACGATACCCGCTACTGACGCTACTA
ATAATATACATTGGTCATACTTACATATTAAATTCGCAGAACCTATAAGTCTATTCGTATGCGACGCAGAA
TTATCCGTTACAGTGAATTGGTCTAAAATTATTATCGAATGGTCTAAACACGTTAGAAAATGCAAATATTG
TTCTAGCGTTAATAAGTGTATGTTAATCGTTAAGTATCACGCTCAAGACGATATAGATTTTAAATTAGATA
ATATAACTATACTTAAAACATACGTATGCTTAGGTAGTAAGCTTAAGGGTAGCGAAGTATACTTAGTGTTA
ACGATAGGTCCAGCTAATATTTTTCCCGTTTTTAACGTAGTGCAAAACGCTAAATTGATTCTATCTAGAAC
TAAAAATTTTATAATGCCTAAGAAAGCTGATAAAGAGTCAATTGACGCTAATATAAAATCATTGATACCAT
TCTTATGTTATCCTATAACTAAGAAAGGGATTAATACCGCACTATCTAAACTTAAATCCGTAGTGAGCGGA
GATATACTATCTTATAGTATAGCCGGTAGAAACGAAGTTTTTAGTAATAAATTGATTAATCATAAACATAT
GAATATACTTAAATGGTTTAATCACGTACTTAATTTTAGATCAACCGAATTGAATTATAATCATCTATATA
TGGTCGAATCTACATATCCATACTTATCCGAACTGTTAAACTCATTGACTACTAACGAATTGAAGAAATTG
ATTAAAATTACAGGTAGTCTGTTATACAATTTTCATAACGAATAATGAATAAAGATCTTATAATAAAAATT
CCCATAGCTATACACTAACACTGTATTCAATTATAGTTATTAAAAATTAAAAATCATATAATTTTTTAAAT
AACTTTTAGTGAACTAATCCTAAAGTTATCATTTTAATCTTGGAGGAATAAATTTAAACCCTAATCTAATT
GGTTTATATGTGTATTAACTAAATTACGAGATATTAGTTTTTGACACTTTTTTTCTCGT

VACCINE CANDIDATES FOR HUMAN RESPIRATORY SYNCYTIAL VIRUS (RSV) HAVING ATTENUATED PHENOTYPES

CROSS REFERENCE TO RELATED APPLICATIONS

This application is a continuation of U.S. patent application Ser. No. 16/335,099, filed Mar. 20, 2019, now U.S. Pat. No. 10,808,012, issued Oct. 20, 2020, which is a national stage application under 35 U.S.C. 371 of PCT Application No. PCT/US2017/053047 having an international filing date of Sep. 22, 2017, which designated the United States, which PCT application claimed priority to U.S. Provisional Application Ser. No. 62/399,133, filed Sep. 23, 2016, and U.S. Provisional Application Ser. No. 62/400,476, filed Sep. 27, 2016, the contents of each of which are incorporated herein by reference in their entireties for all purposes.

GOVERNMENT RIGHTS

The Government of the United States has certain rights in this invention.

REFERENCE TO SEQUENCE LISTING

This application contains a Sequence Listing submitted as an electronic text file named "Sequence_Listing_6137NIAID-65-PCT_ST25.txt", having a size in bytes of 98 kb, and created on Sep. 20, 2017. The information contained in this electronic file is hereby incorporated by reference in its entirety pursuant to 37 CFR § 1.52(e)(5).

FIELD OF THE INVENTION

The subject matter disclosed herein relates to respiratory syncytial virus (RSV) and attenuated, mutant strains thereof suitable for use as vaccines.

BACKGROUND OF THE INVENTION

Human respiratory syncytial virus (RSV) infects nearly everyone worldwide early in life and is responsible for considerable mortality and morbidity (for general reviews, see: Collins and Graham, 2008, J Virol. 82:2040-2055; Collins and Melero, 2011, Virus Res 162: 80-99; Collins and Karron, 2013, Fields Virology 6th Edition, pp 1086-1123; Collins, et al., 2013, Curr Top Microbiol Immunol 372:3-38). In the United States alone, RSV is responsible for 75,000-125,000 hospitalizations yearly, and conservative estimates indicate that RSV is responsible worldwide for 64 million pediatric infections and 160,000 or more pediatric deaths each year. Another notable feature of RSV is that severe infection in infancy frequently is followed by lingering airway dysfunction, including a predisposition to airway reactivity, that in some individuals lasts for years and can extend into adolescence and beyond. RSV infection exacerbates asthma and may be involved in initiating asthma.

RSV is a negative strand RNA virus of the pneumoviridae family. The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA that has two overlapping open reading frames (ORFs) encoding two separate proteins M2-1 and M2-2. The 11 RSV proteins are: the RNA-binding nucleoprotein (N), the phosphoprotein (P), the large polymerase protein (L), the attachment glycoprotein (G), the fusion protein (F), the small hydrophobic (SH) surface glycoprotein, the internal matrix protein (M), the two nonstructural proteins NS1 and NS2, and the M2-1 and M2-2 proteins. The RSV gene order is: 3'-NS1-NS2-N-P-M-SH-G-F-M2-L. Each gene is flanked by short conserved transcription signals called the gene-start (GS) signal, present on the upstream end of each gene and involved in initiating transcription of the respective gene, and the gene-end (GE) signal, present at the downstream end of each gene and involved in directing synthesis of a polyA tail followed by release of the mRNA.

The RSV F and G proteins are the only RSV proteins known to induce RSV neutralizing antibodies, and are the major protective antigens. The F protein generally is considered to be is a more effective neutralization and protective antigen than the G protein. F also is relatively well-conserved among RSV strains, whereas the G protein can be substantially divergent. The divergence in G is a major factor in segregating RSV strains into two antigenic subgroups, A and B (~53% and ~90% amino acid sequence identity between the two subgroups for G and F, respectively). The tools and methods of the present disclosure focus on RSV strain A2 of subgroup A, but can readily be applied to other strains of either subgroup.

Vaccines and antiviral drugs against RSV are in preclinical and clinical development by a number of investigators; however, no vaccines or antiviral drugs suitable for routine use against RSV are commercially available.

The development of RSV vaccines has been in progress since the 1960's but has been complicated by a number of factors. For example, immunization of RSV-naïve infants with inactivated RSV has been shown to prime for enhanced disease upon subsequent natural RSV infection, and studies in experimental animals indicate that disease enhancement also is associated with purified RSV subunit vaccines. However, enhanced RSV disease has not been observed in association with live or live-vectored RSV vaccines, and this important observation has been confirmed in a number of clinical studies (Wright, et al., 2007, Vaccine 25:7372-7378). Thus, inactivated and subunit vaccines are contraindicated for infants and young children, whereas appropriately-attenuated live and live-vectored vaccines are acceptable for use in this population, which is the primary vaccine target population.

Another obstacle to immune protection is that RSV replicates and causes disease in the superficial cells of the respiratory airway lumen, where immune protection has reduced effectiveness. Thus, immune control of RSV infection is inefficient and often incomplete, and it is important for an RSV vaccine to be as immunogenic as possible. Another obstacle to RSV vaccines is that the magnitude of the protective immune response is roughly proportional to the extent of virus replication (and antigen production). Thus, the attenuation of RSV necessary to make a live vaccine typically is accompanied by a reduction in replication and antigen synthesis, and a concomitant reduction in immunogenicity, and therefore it is essential to identify a level of replication that is well tolerated yet satisfactorily immunogenic.

Another aspect of RSV vaccine development is that the virus does not replicate efficiently in most experimental animals, such as rodents and monkeys. Chimpanzees are more permissive but are no longer available for RSV research. Therefore, RSV vaccine development is heavily dependent on clinical studies even in early stages of development. Additionally, RSV grows only to moderate titers in cell culture and is often present in long filaments that are difficult to purify. Further, RSV can readily lose infectivity during handling.

Another obstacle is the difficulty in identifying and developing attenuating mutations. Appropriate mutations must be attenuating in vivo, but should be minimally restrictive to replication in vitro, since this is essential for efficient vaccine manufacture. Yet another obstacle is genetic instability that is characteristic of RNA viruses, whereby attenuating mutations can revert to the wild-type (wt) assignment or to an alternative assignment that confers a non-attenuated phenotype.

The combined approach of sequence design and synthetic biology allows the generation of DNA molecules with extensive targeted modifications. Synonymous genome recoding, in which one or more ORFs of a microbial pathogen are modified at the nucleotide level without affecting amino acid coding, currently is being widely evaluated to reduce pathogen fitness and create potential live-attenuated vaccines, particularly for RNA viruses. The main strategies for attenuation by synonymous genome recoding are: codon-deoptimization (CD), codon-pair-deoptimization (CPD), and increasing the dinucleotide CpG and UpA content (which is usually the result of CD and CPD).

Deoptimized virus genomes contain dozens to thousands of silent nucleotide mutations in one or more ORFs. Presumably, attenuation is based on the sum of many individual mutations. This mutation multiplicity is expected to confer stability against substantial de-attenuation, as the high number of mutations would present a significant barrier against reversion to virulence. In principle, on the background of thousands of attenuating mutations, any single-site reversion should yield only a minuscule selective advantage. The most likely path to reversion imaginable under this model is the progressive accumulation of many individual mutations, providing for a slow progression of de-attenuation.

To date, genetic stability studies of large-scale deoptimized viruses have shown that de-attenuation indeed appears to be low, suggesting that these viruses are genetically stable. However, an important limitation of these studies is that the de-optimized viruses generally have not been subjected to strong selective pressure that would favor the outgrowth of viruses with de-attenuating mutations.

Thus, there continues to be a need for live attenuated RSV strains that replicate efficiently in vitro, and are maximally immunogenic, attenuated, and refractory to de-attenuation in vivo.

SUMMARY OF THE INVENTION

Disclosed herein are presumptively de-attenuating mutations in vitro that are useful, either individually or in combination with other known mutations, in producing recombinant strains of human respiratory syncytial virus (RSV) exhibiting attenuation phenotypes in vivo. Further disclosed herein are novel live-attenuated RSV strains suitable for use as RSV vaccines. Also provided herein are methods and compositions related to the expression of the disclosed viruses. For example, isolated polynucleotide molecules that include a nucleic acid sequence encoding the genome or antigenome of the described viruses are disclosed.

In one embodiment, the present invention includes an isolated polynucleotide molecule encoding a recombinant respiratory syncytial virus (RSV) variant having an attenuated phenotype comprising a RSV genome or antigenome sequence, wherein the RSV genome or antigenome is modified by a mutation in the L ORF at a position corresponding to T1166 of the L protein in SEQ ID NO:11.

In some embodiments, the RSV genome or antigenome is further modified by a mutation selected from the group consisting of (i) a mutation in the M2-1 ORF at a position corresponding to N88 or A73 of the M2-1 protein in SEQ ID NO:9; (ii) a mutation in the N ORF at a position corresponding to K136 of the N protein in SEQ ID NO:3; (iii) a mutation in the P ORF at a position corresponding to E114 of the P protein in SEQ ID NO:4; and (iv) combinations thereof. In some embodiments, the RSV genome or antigenome is further modified by a mutation selected from the group consisting of (i) a mutation in the M2-1 ORF at a position corresponding to N88 of the M2-1 protein in SEQ ID NO:9; (ii) a mutation in the N ORF at a position corresponding to K136 of the N protein in SEQ ID NO:3; (iii) a mutation in the P ORF at a position corresponding to E114 of the P protein in SEQ ID NO:4; and (iv) combinations thereof. In some embodiments, the RSV genome or antigenome is further modified by a mutation selected from the group consisting of (i) a mutation in the M2-1 ORF at a position corresponding to A73 of the M2-1 protein in SEQ ID NO:9; (ii) a mutation in the N ORF at a position corresponding to K136 of the N protein in SEQ ID NO:3; (iii) a mutation in the P ORF at a position corresponding to E114 of the P protein in SEQ ID NO:4; and (iv) combinations thereof. In some embodiments, the RSV genome or antigenome is modified by at least two of mutations (i)-(iii). In some embodiments, the RSV genome or antigenome is modified by all of mutations (i)-(iii).

In some embodiments, the mutation in the L ORF at a position corresponding to T1166 of the L protein in SEQ ID NO:11 is T1166I. In some embodiments, (a) the mutation in the M2-1 ORF at a position corresponding to N88 of the M2-1 protein in SEQ ID NO:9 is N88K and the mutation in the M2-1 ORF at a position corresponding to A73 of the M2-1 protein in SEQ ID NO:9 is A73S; (b) the mutation in the N ORF at a position corresponding to K136 of the N protein in SEQ ID NO:3 is K136R; and (c) the mutation in the P ORF at a position corresponding to E114 of the P protein in SEQ ID NO:4 is E114V. In some embodiments, the RSV genome or antigenome is modified by at least two of mutations a-c. In some embodiments, the RSV genome or antigenome is modified by all of mutations a-c. In some embodiments, the mutation in the L ORF at a position corresponding to T1166 of the L protein in SEQ ID NO:11 is T1166I.

In some embodiments, the RSV genome or antigenome is modified by the mutations corresponding to T1166I in the L protein in SEQ ID NO:11, N88K in the M2-1 protein in SEQ ID NO:9, K136R in the N protein in SEQ ID NO:3 and E114V in the P protein in SEQ ID NO:4. In some embodiments, the RSV genome or antigenome is modified by the mutations corresponding to T1166I in the L protein in SEQ ID NO:11, A73S in the M2-1 protein in SEQ ID NO:9, K136R in the N protein in SEQ ID NO:3 and E114V in the P protein in SEQ ID NO:4.

In another embodiment, the present invention includes an isolated polynucleotide molecule encoding a recombinant respiratory syncytial virus (RSV) variant having an attenuated phenotype comprising a RSV genome or antigenome sequence, wherein the RSV genome or antigenome is modified by one or more mutations selected from the positions recited in Table S1. In some embodiments, the RSV genome or antigenome is modified by one or more mutations selected from the positions recited in Table S1-A. In some embodiments, the RSV genome or antigenome is modified by one or more mutations selected from the positions recited in Table S1-B.

In another embodiment, the present invention includes an isolated polynucleotide molecule encoding a recombinant respiratory syncytial virus (RSV) variant having an attenuated phenotype comprising a RSV genome or antigenome sequence, wherein the RSV genome or antigenome is modified by one or more mutations selected from the positions recited in Table S2. In some embodiments, the RSV genome or antigenome is modified by one or more mutations selected from the positions recited in Table S2-A. In some embodiments, the RSV genome or antigenome is modified by one or more mutations selected from the positions recited in Table S2-B.

In another embodiment, the present invention includes an isolated polynucleotide molecule encoding a recombinant respiratory syncytial virus (RSV) variant having an attenuated phenotype comprising a RSV genome or antigenome sequence, wherein the RSV genome or antigenome is modified by one or more mutations selected from the positions recited in Table S3. In some embodiments, the RSV genome or antigenome is modified by one or more mutations selected from the positions recited in Table S3-A. In some embodiments, the RSV genome or antigenome is modified by one or more mutations selected from the positions recited in Table S3-B.

In some embodiments, the RSV genome or antigenome comprises a deletion in at least one of the proteins selected from M2-2, NS1 and NS2. In some embodiments, the RSV genome or antigenome is codon-pair deoptimized. In some embodiments, the L-ORF of the RSV genome or antigenome is codon-pair deoptimized.

In some embodiments, the present invention includes a polynucleotide molecule comprising a nucleotide sequence that is at least about 80% identical to the nucleotide sequence of SEQ ID NO:14. In some embodiments, the present invention includes a polynucleotide molecule comprising nucleotide sequence that is at least about 90% identical to the nucleotide sequence of SEQ ID NO:14. In some embodiments, the present invention includes a polynucleotide molecule comprising nucleotide sequence that is at least about 95% identical to the nucleotide sequence of SEQ ID NO:14. In some embodiments, the present invention includes a polynucleotide molecule comprising the nucleotide sequence of SEQ ID NO:14.

In some embodiments, the present invention includes a vector comprising the isolated polynucleotide molecules described above. In some embodiments, the present invention includes a cell comprising the isolated polynucleotide molecules described above.

In some embodiments, the present invention includes a pharmaceutical composition comprising an immunologically effective amount of the recombinant RSV variant encoded by the isolated polynucleotide molecules described above. In some embodiments, the present invention includes a method of vaccinating a subject against RSV comprising administering the pharmaceutical composition. In some embodiments, the present invention includes a method of inducing an immune response comprising administering the pharmaceutical composition. In some embodiments, the pharmaceutical composition is administered intranasally. In some embodiments, the pharmaceutical composition is administered via injection, aerosol delivery, nasal spray or nasal droplets.

In some embodiments, the present invention includes a live attenuated RSV vaccine comprising the recombinant RSV variant encoded by the isolated polynucleotides described above. In some embodiments, the present invention includes a pharmaceutical composition comprising the RSV vaccine. In some embodiments, the present invention includes a method of making the vaccine comprising expressing the isolated polynucleotide molecules described above.

Figure 4:
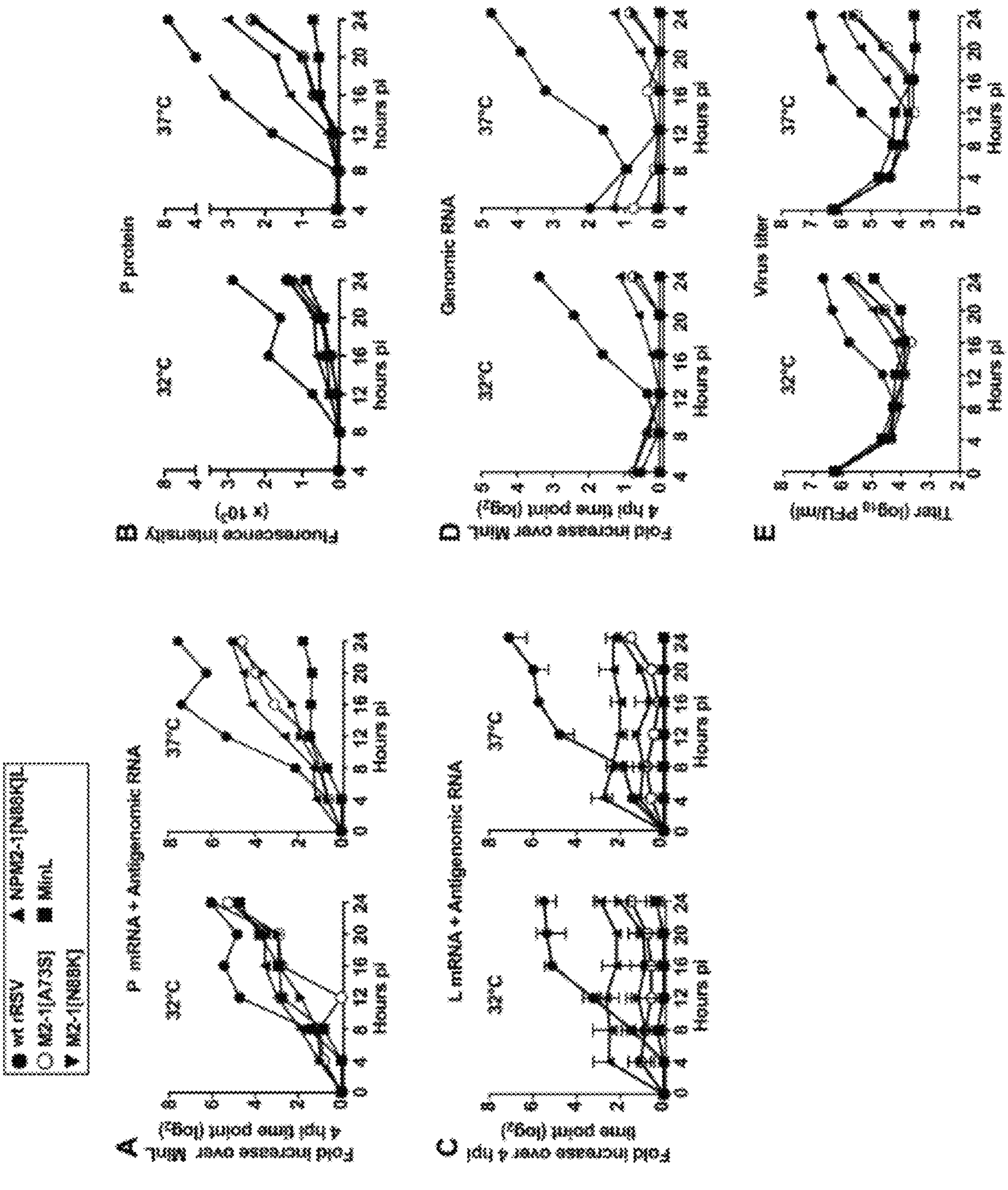
Figure 4:
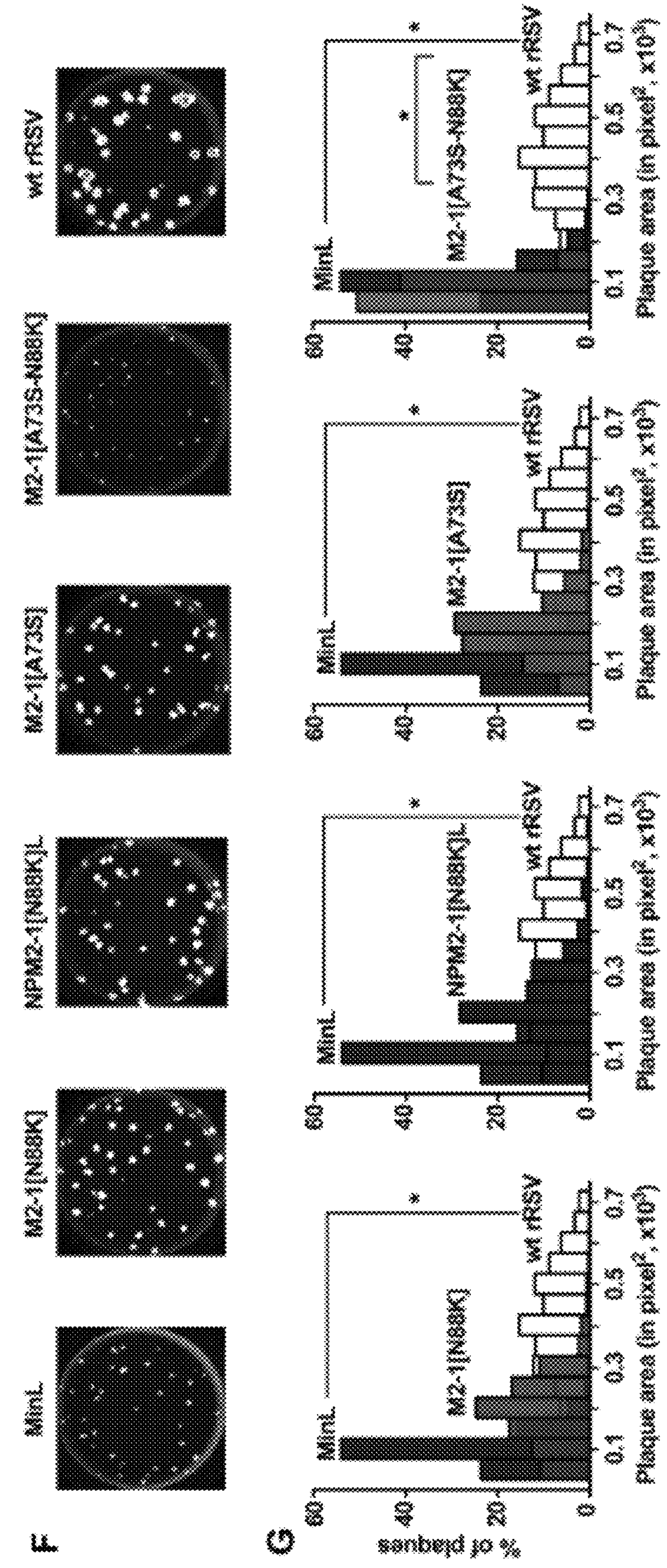

FIG. 4 shows the effects of specific mutations on RNA synthesis and plaque size of Min_L derivatives. (A-E) Replicate cultures of Vero cells were infected (MOI of 3) with the indicated viruses. Cultures were harvested every 4 h from 4 to 24 hpi for analysis of cell-associated RNA, protein, and virus. (A) Positive-sense viral RNA (i.e., mRNA+antigenome) was quantified in triplicate by strand-specific RT-qPCR. Data for P are shown. QPCR results were analyzed using the comparative threshold cycle (ΔCt) method, normalized to 18S rRNA, and expressed as $\log_2$ fold increase over the Min_L 4 h time point. (B) Quantification of P protein expression by Western blotting. (C) Quantification of L mRNA+antigenome by strand-specific RT-qPCR (fold increase relative to the 4 hpi time point, calculated separately for each virus, as different primer-probes sets were required for wt L gene in wt rRSV versus the CPD L gene present in Min_L and its derivatives). For wt L and CPD L, data were derived from 3 and 4 different primer-probe sets, respectively, designed along the L ORFs, and the median values with ranges are shown. (D) Quantification of cell-associated genomic RNA by strand-specific RT-qPCR, expressed as fold increase over the 4 hpi time point of Min_L. (E) Virus titers from cultures incubated at 32 and 37° C., assayed at 32° C. (F-G) Virus plaque sizes. Vero cells were infected with 30 pfu per 2 $cm^2$ well of wt rRSV, Min_L, and Min_L-derived mutants and incubated under methylcellulose at 32° C. for 12 days. Plaques were visualized by immunostaining and quantified by IR imaging (Licor) using Image J. (F) Representative pictures of virus plaque sizes. (G) Plaques size distribution of the indicated viruses. A minimum of 1000 plaques per virus was measured (*=p≤0.05).

Figure 5:
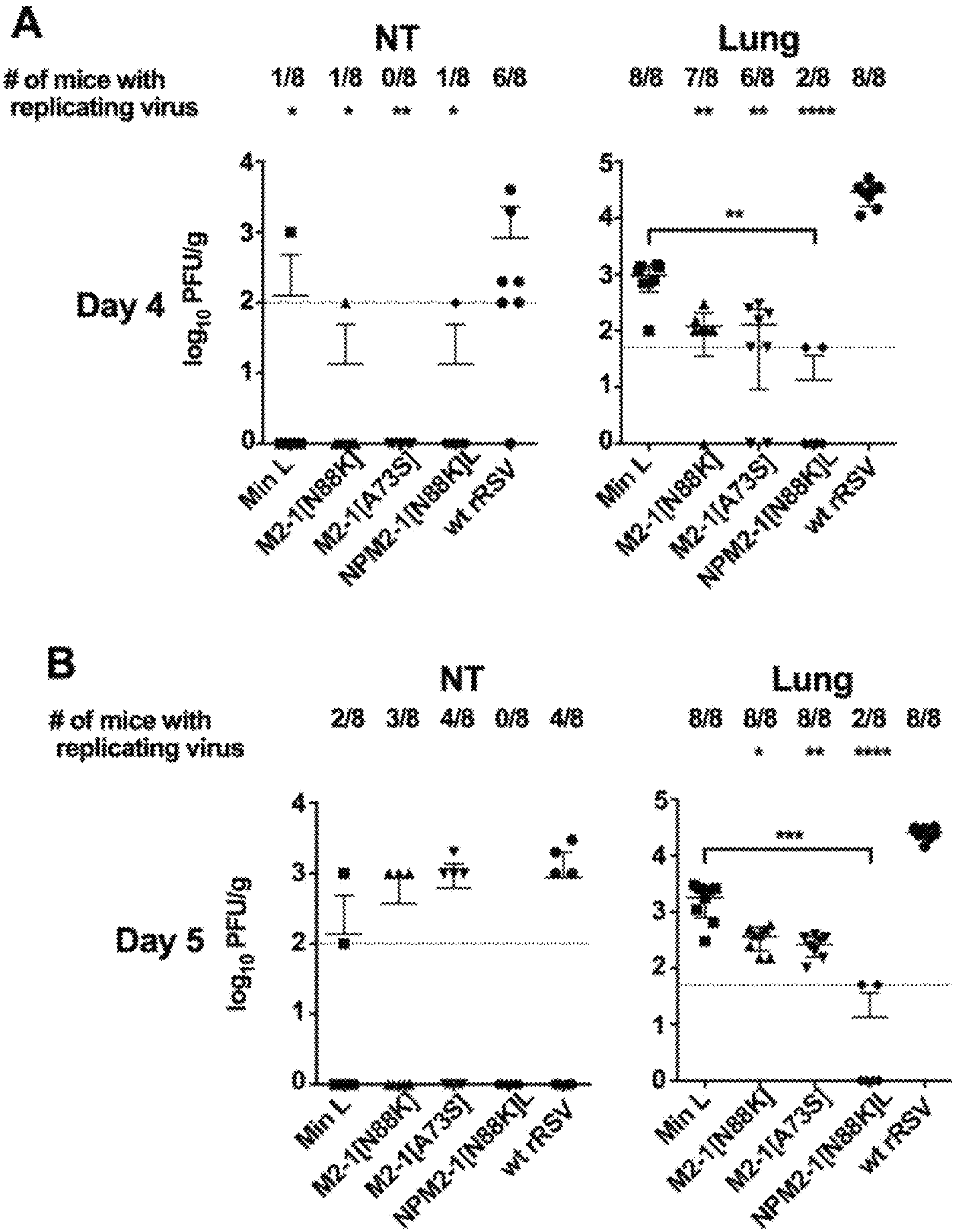
Figure 5:
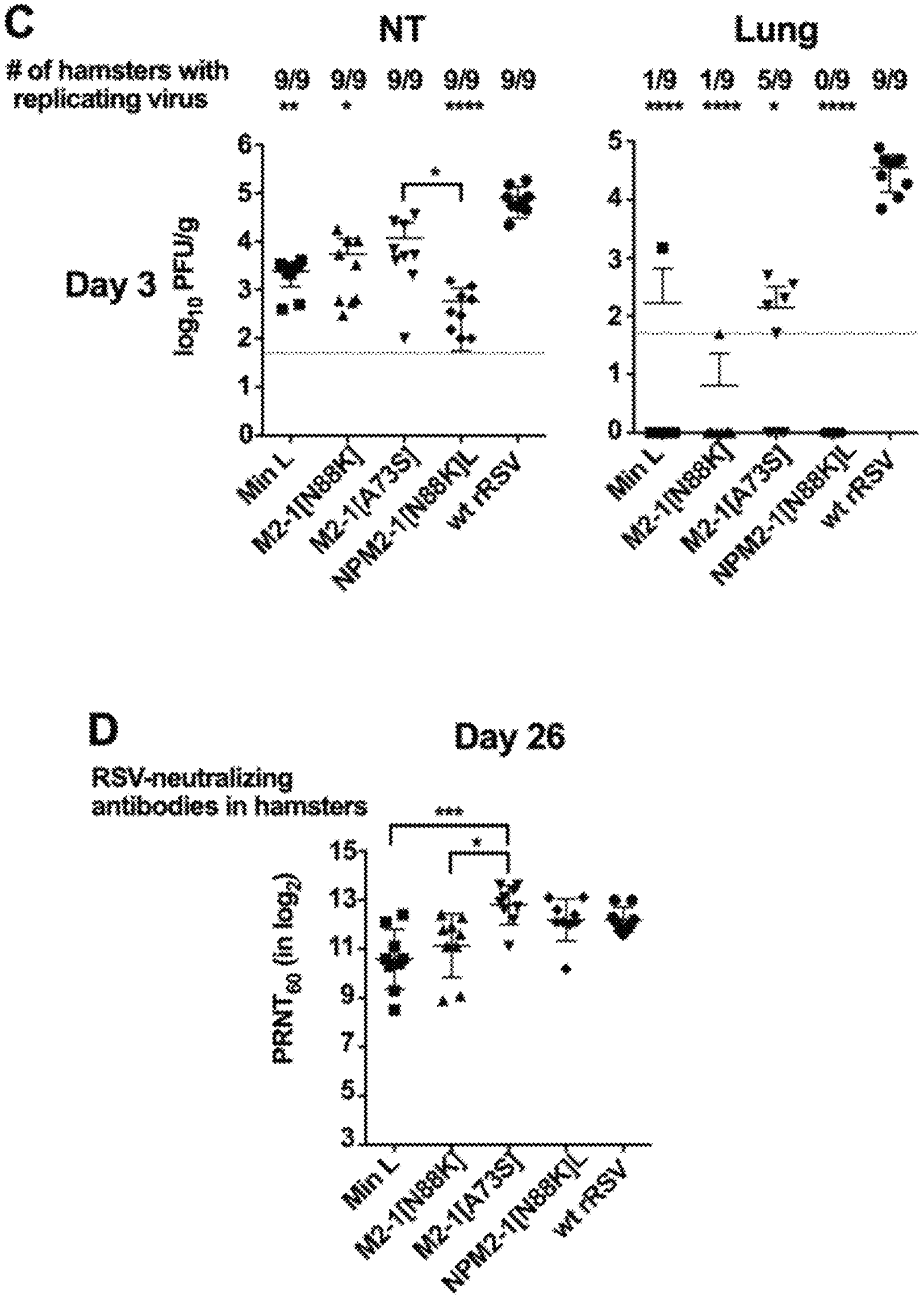

FIG. 5 show the analysis of Min_L derivatives in rodents, which indicates differing effects of M2-1 mutations A73S and N88K and identifies the improved vaccine candidate NPM2-1[N88K]L. Replication of Min_L, Min_L mutants and wt rRSV in mice at day 4 (A) and 5 pi (B) or in hamsters at day 3 pi (C). Groups of 20 mice (A-B) or 18 hamsters (C) were infected intranasally with $10^6$ pfu of the indicated virus/animal. At day 4 (A), 5 (B) and 10 pi (data not shown) for the mouse study or at day 3 for the hamster study (C), RSV titers in nasal turbinates (NT) and lungs were determined as described in the experimental procedures section. The limit of detection is indicated by a dotted line. (D) RSV-neutralizing antibodies at day 26 in hamsters from 9 hamsters per group. The 60% plaque reduction neutralizing antibody titers ($PRNT_{60}$) were determined as described previously. Statistical differences compared with wt rRSV indicated on the top of each graph; statistical differences between Min_L and the Min_L-derived mutants indicated by brackets (*p≤0.05, p≤0.01, *p≤0.001 and ****p≤0.0001).

Figure 6:
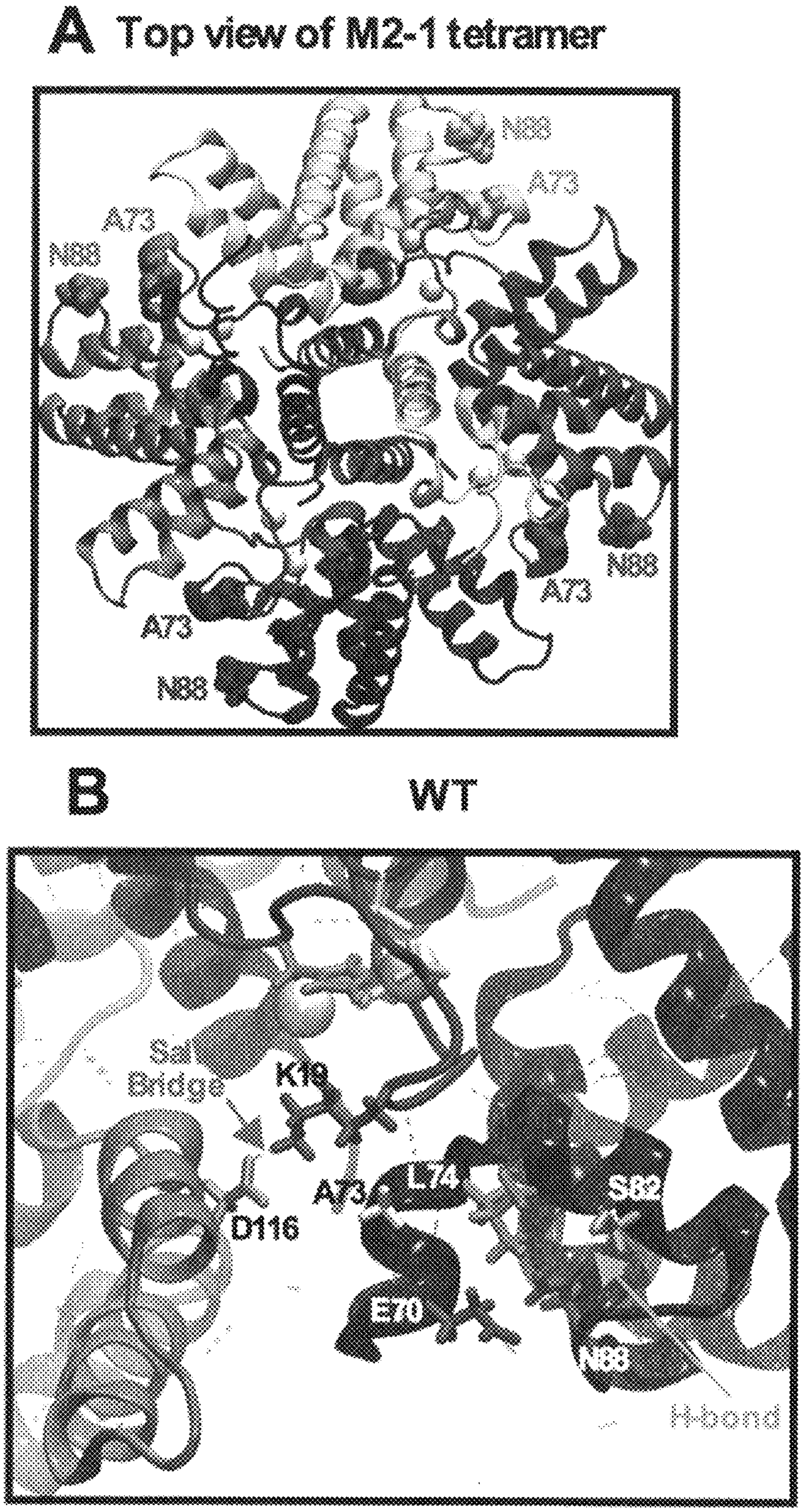
Figure 6:
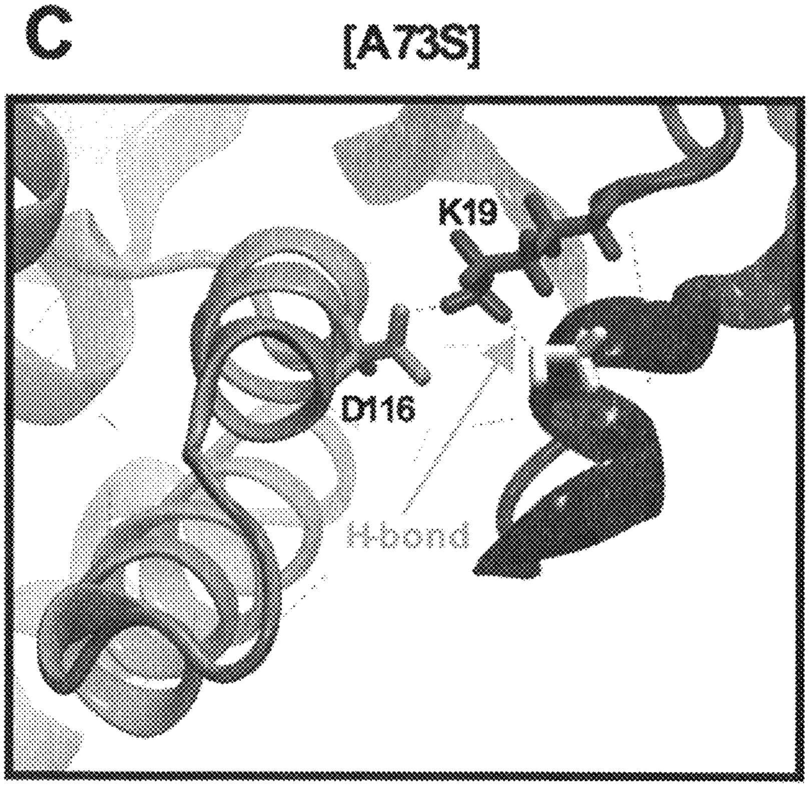
Figure 6:
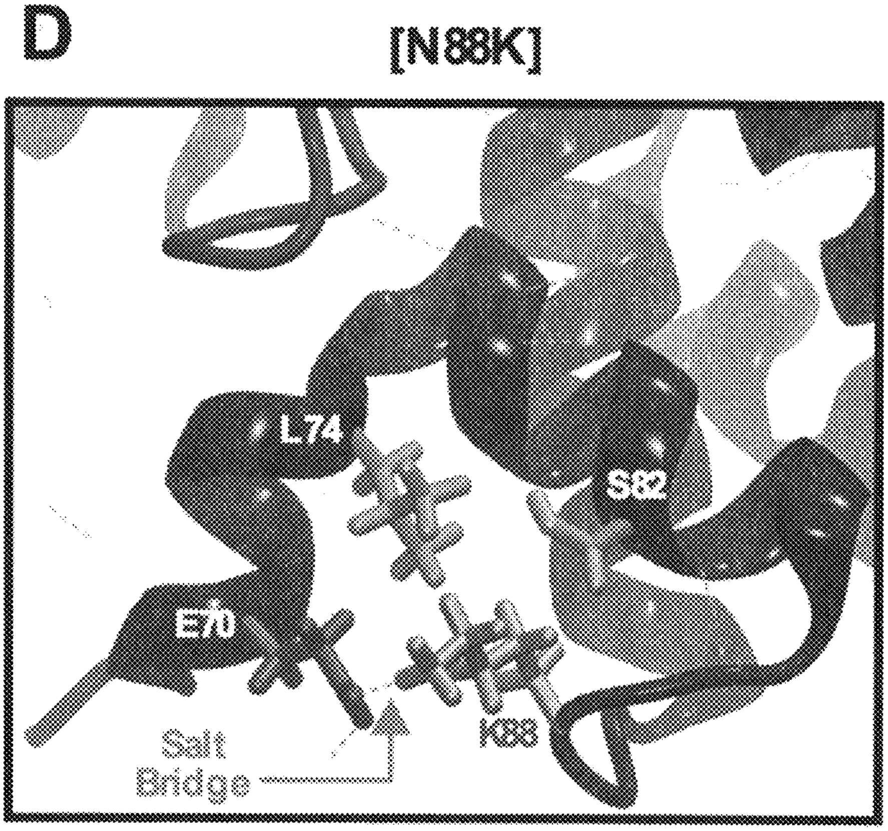

FIG. 6 shows molecular modeling of the impact of de-attenuating mutations on the M2-1 tetramer. (A) Top view of wt M2-1 tetramer. (B) Enlargement of one wt tetramer's region that contains amino acids A73 and N88. (C) Molecular dynamics snapshot of the region proximal to the S73 mutation. The [A73S] mutation is shown and the arrows indicate the predicted new hydrogen bond. (D) Molecular dynamics snapshot of the K88 mutant region. The [N88K] mutation is indicated and an arrow indicates the expected new salt-bridge.

Figure 7:
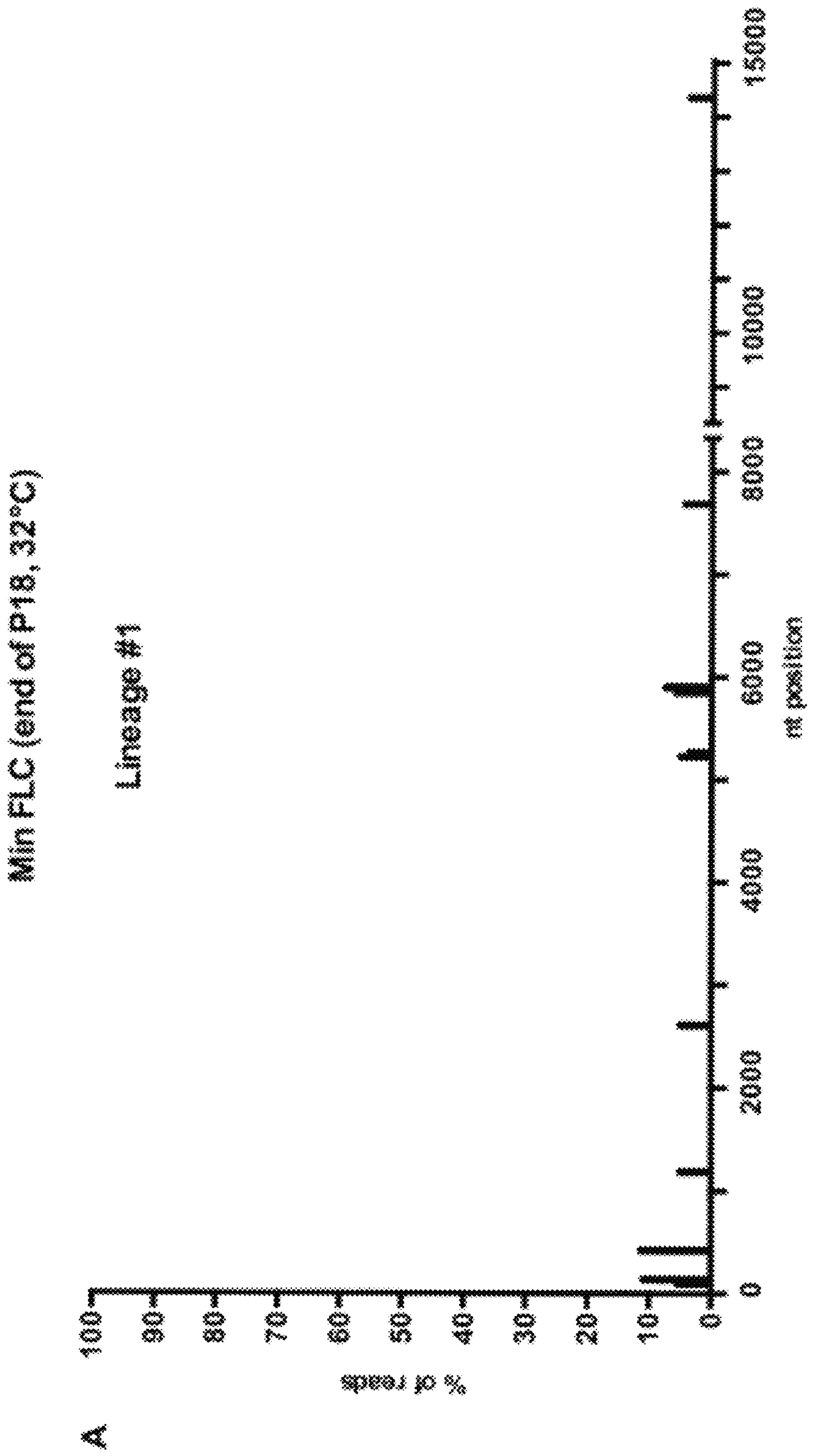
Figure 7:
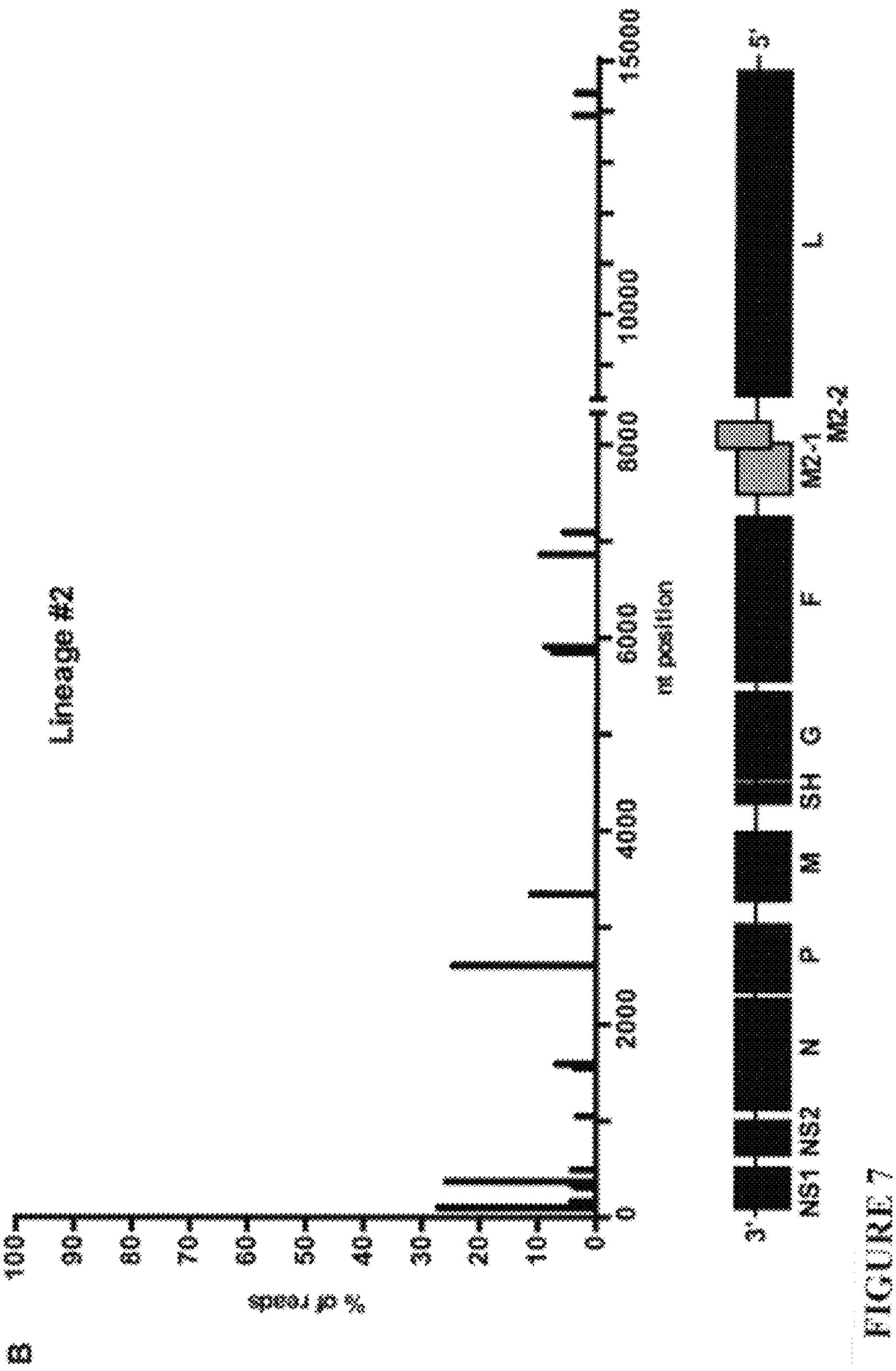

FIG. 7 shows the minimal accumulation of adventitious mutations in Min_FLC during 18 passages at 32° C. Min_FLC was subjected to 18 passages at 32° C. At the end of passage 18, viral RNA was extracted from lineage #1 (A) and #2 (B), and the complete genome was amplified by overlapping RT-PCR and analyzed by deep sequencing (Ion Torrent). Adventitious mutations (which are not specifically identified) are indicated by bars showing their genome position and relative abundance. WT genes are colored in grey shading, while CPD genes are colored in black shading.

Figure 8:
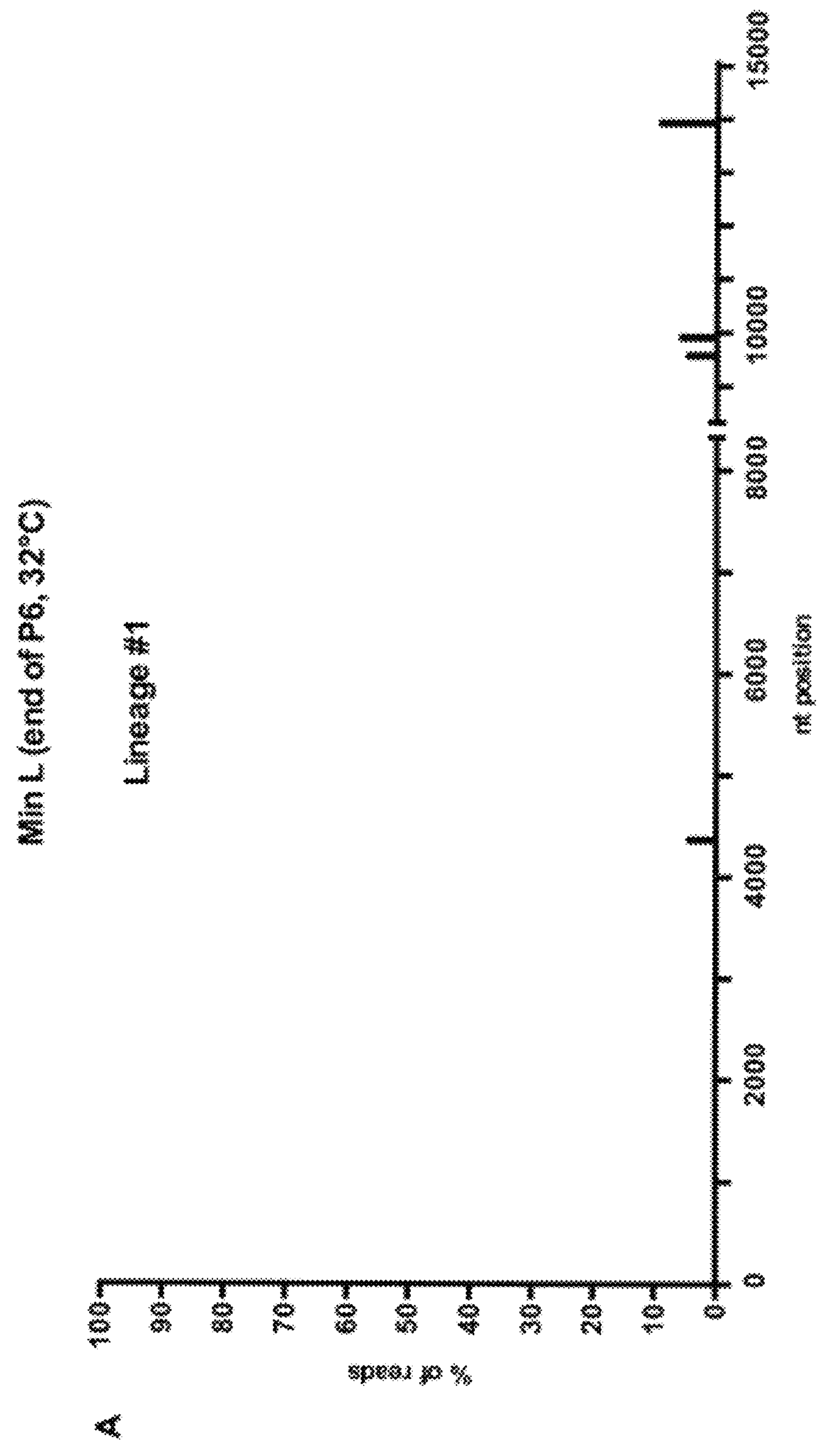
Figure 8:
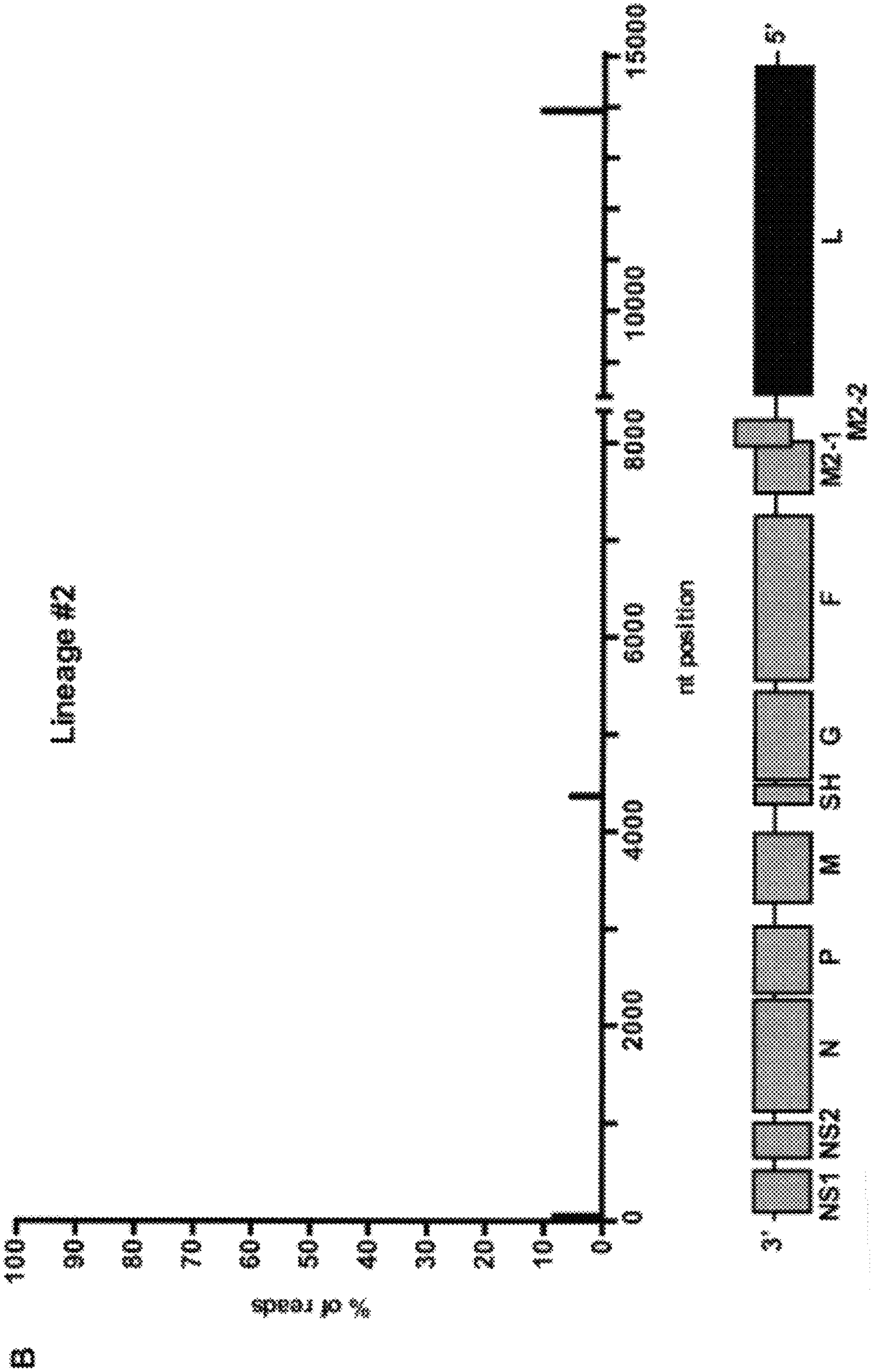

FIG. 8 shows the minimal accumulation of adventitious mutations in Min_L during 6 passages at 32° C. Min_L was sequentially passed 8 times at 32° C. on Vero cells. At the end of passage 6, viral RNA was extracted from lineage #1 (A) and #2 (B), and the complete genome was amplified by overlapping RT-PCR and analyzed by deep sequencing (Ion Torrent). Adventitious mutations are indicated by bars showing their genome position and relative abundance; the specific nucleotide changes are not indicated. WT genes are colored in grey shading, while CPD genes are colored in black shading.

Figure 9:
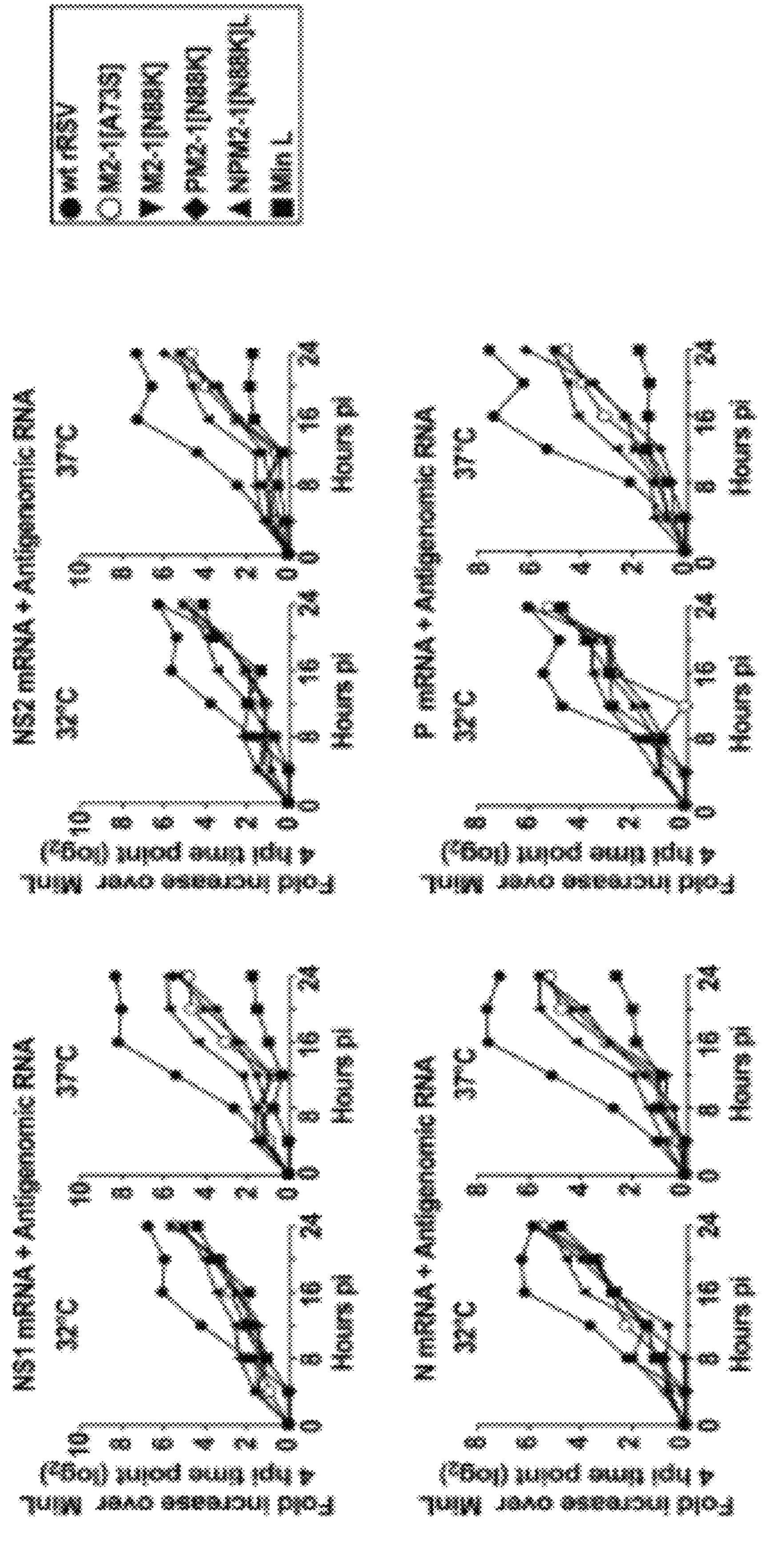
Figure 9:
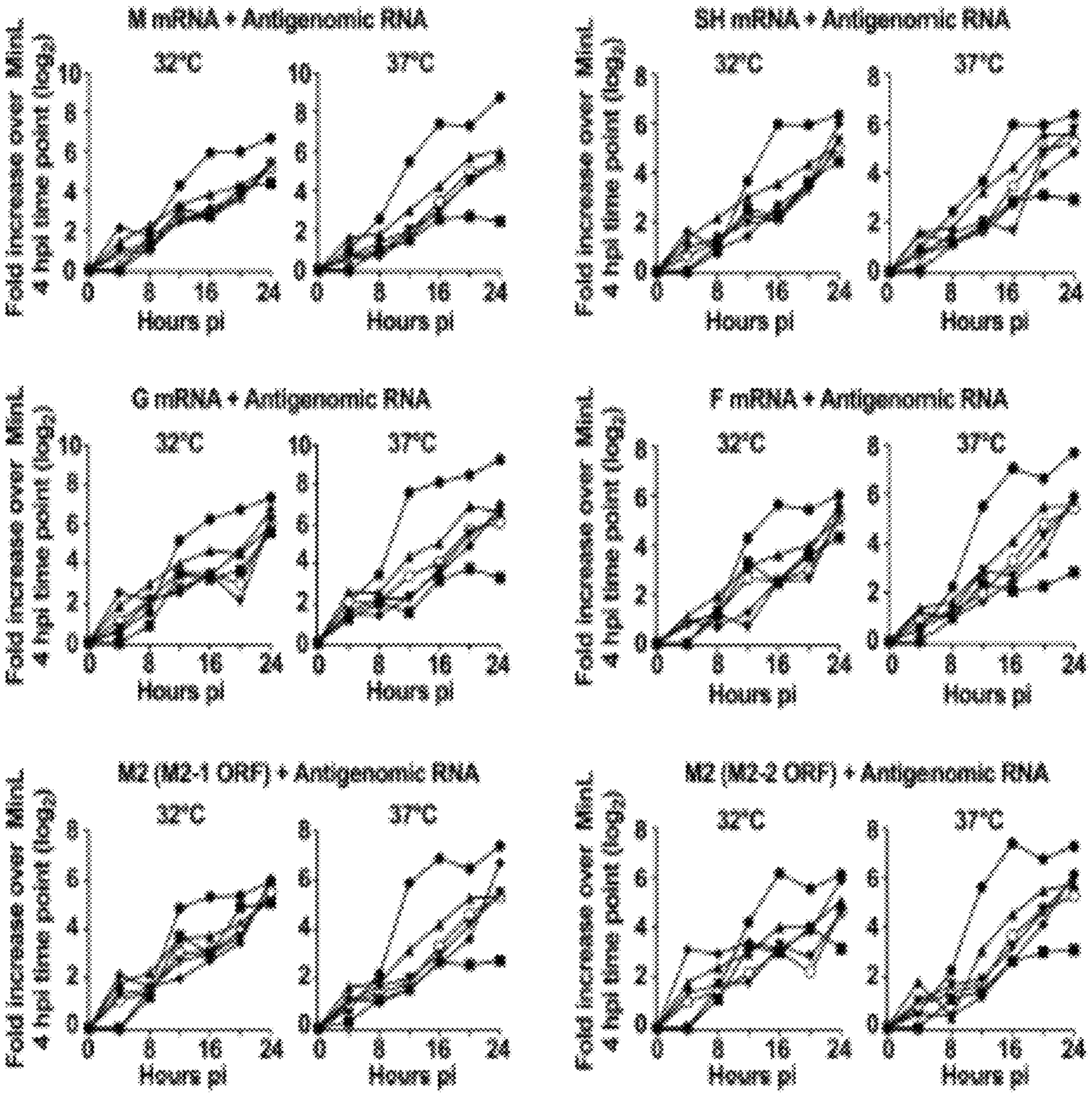

FIG. 9 shows the contributions of specific mutations to the phenotypes of Min_L derivatives: RT-qPCR of cell-associated positive-sense RNA (mRNA+antigenome). The RT-qPCR data during infection of Vero cells with wt rRSV, Min_L, and Min_L-derivatives for the NS1, NS2, N, P, M, SH, G, F, and M2 mRNAs are shown here.

Figure 10:
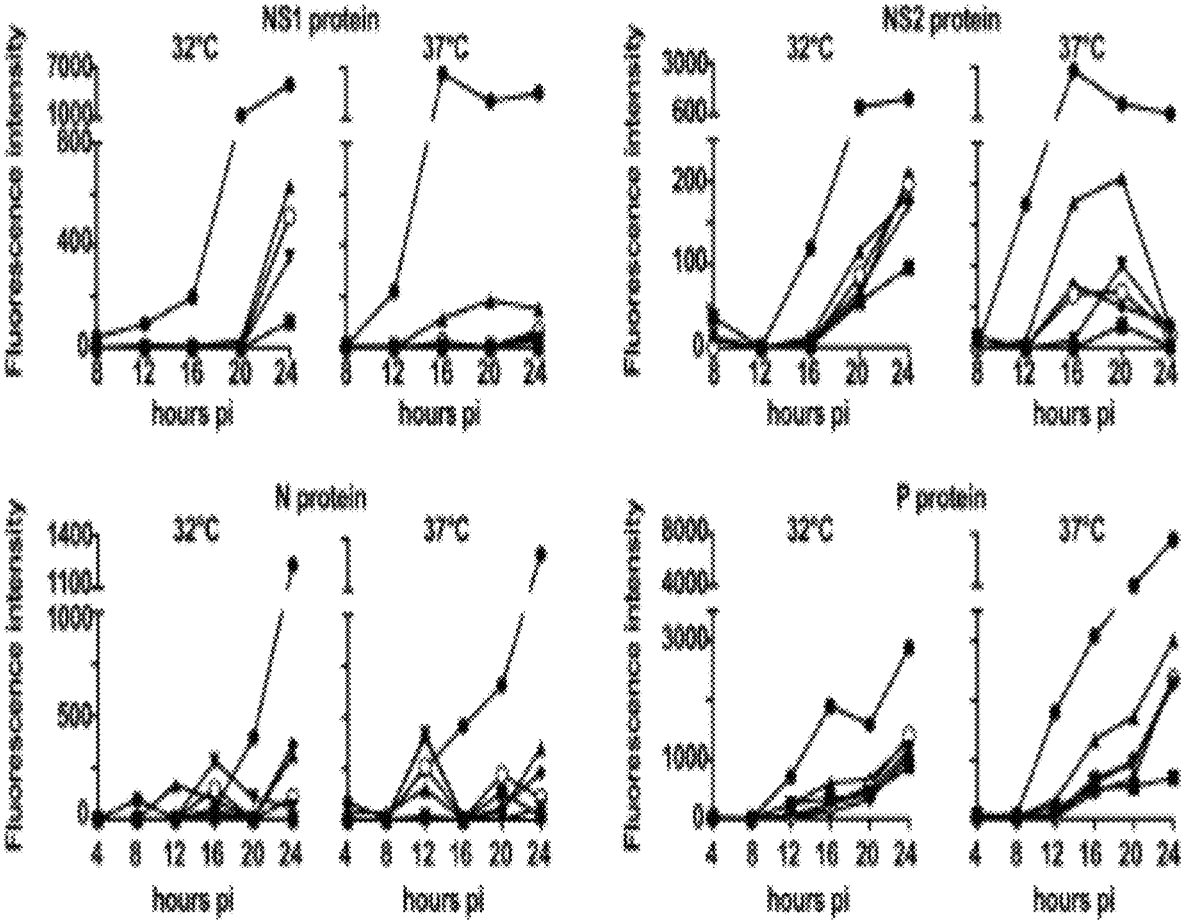
Figure 10:
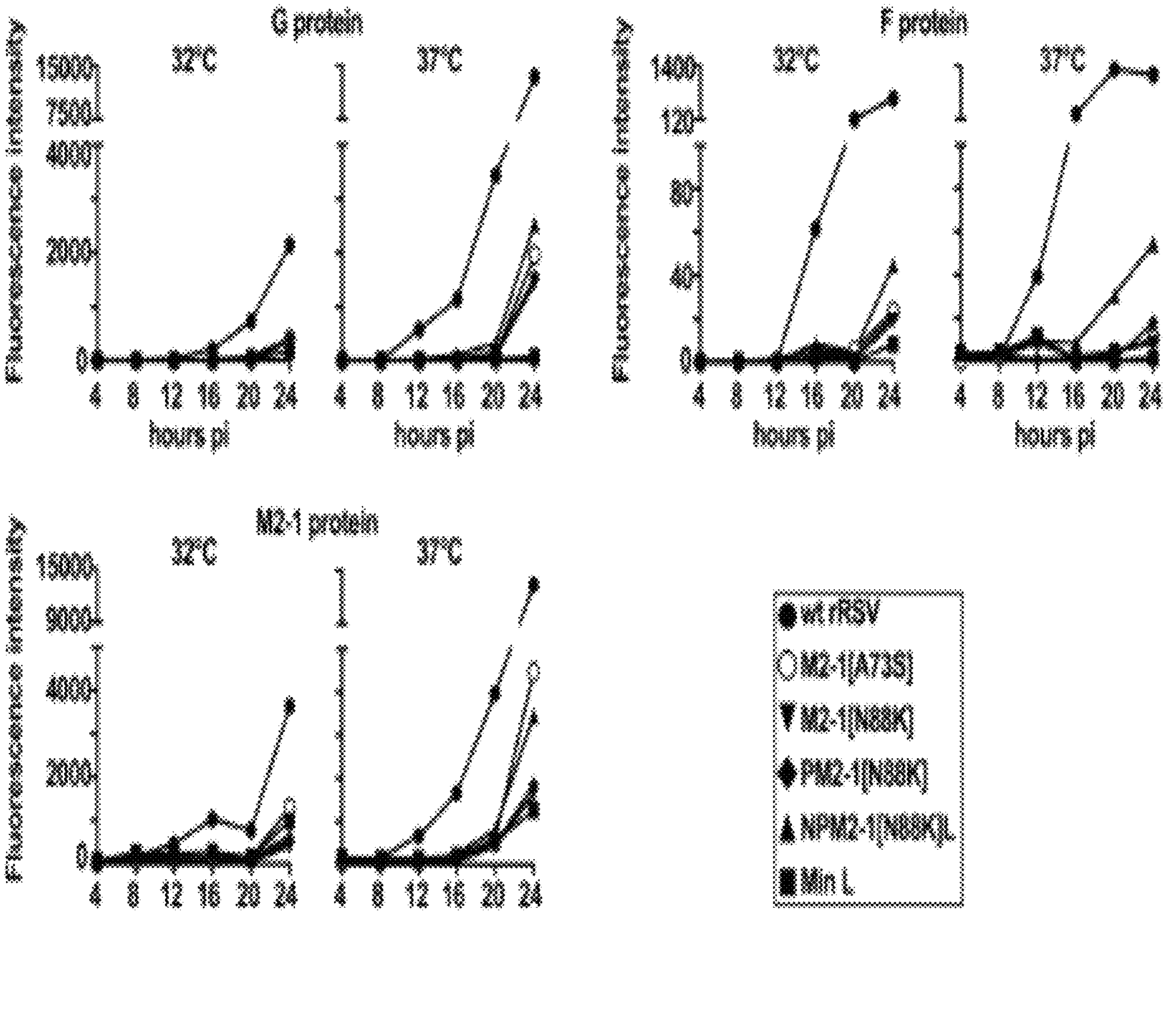

FIG. 10 shows the contributions of specific mutations to the phenotypes of Min_L derivatives: protein expression of Min_L and Min_L-derived mutants. Vero cells were infected at an MOI of 3 pfu/cell at 32 or 37° C. with Min_L, M2-1[A73S], M2-1[N88K], PM2-1[N88K], NPM2-1[N88K]L or wt rRSV. Every 4 h from 4 to 24 hpi, total cell lysates were harvested from one well of a 6-well plate in NuPage LDS sample buffer (Life Technologies). Western blot analysis of NS1, NS2, N, P, G, F and M2-1, was performed as described in the materials and methods section. The GAPDH protein was used as a loading control. Membranes were scanned on the Odyssey® Infrared Imaging System. Data collected was analyzed using Odyssey software, version 3.0. For quantification of identified RSV proteins of interest, background fluorescence was corrected. Values reported indicate the median fluorescence intensity per protein band.

Figure 11:
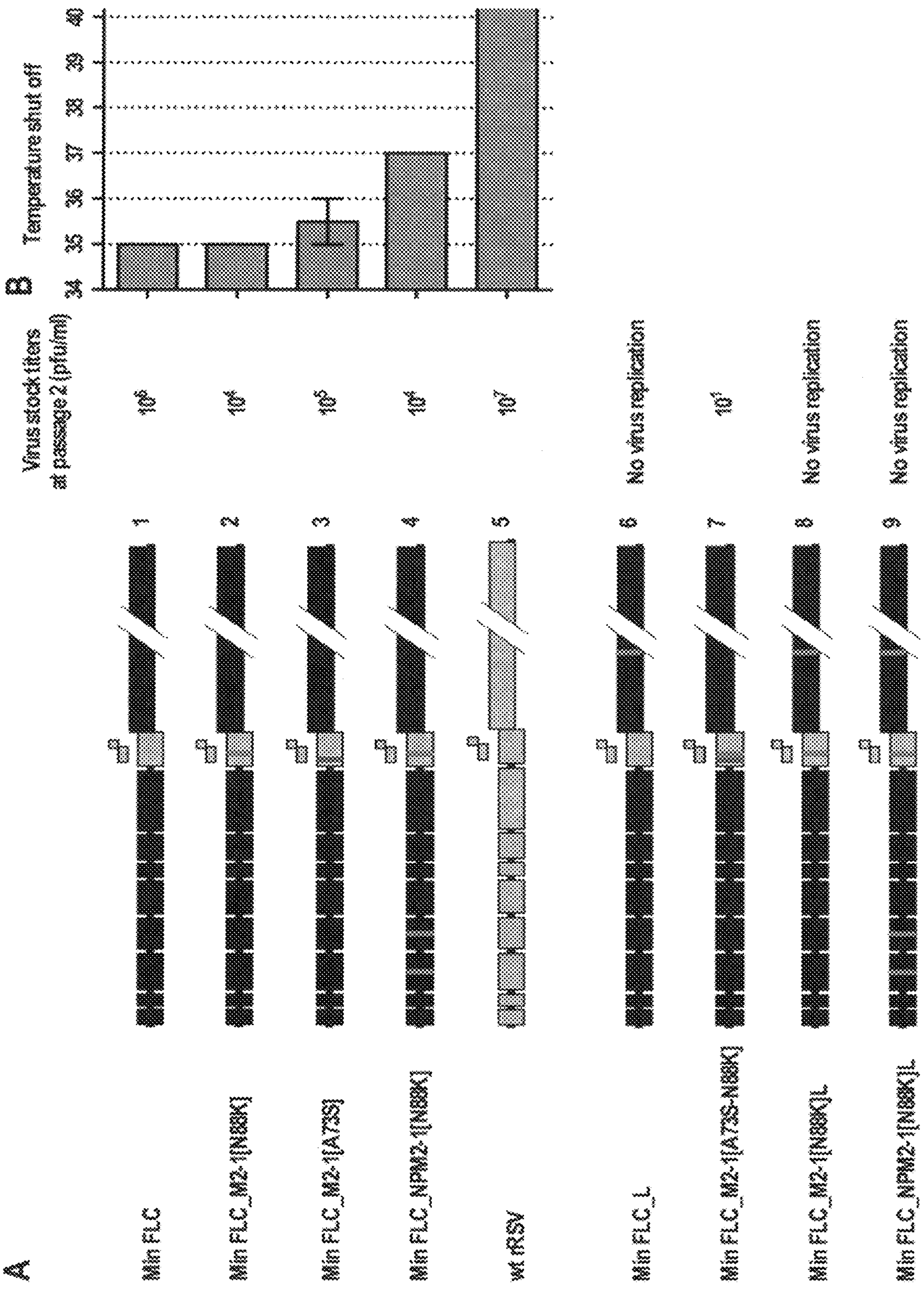

FIG. 11 shows the $T_{SH}$ of Min_FLC derived mutants. The effects of the mutations involved in the loss of temperature sensitivity of Min_L on Min_FLC temperature sensitivity were investigated. (A) To do so, mutations that were identified in Min_L lineage #3 (in N, P, M2-1 [N88K] and L genes) or #8 (M2-1 mutation [A73S]) were re-introduced alone or in the indicated combinations into Min_FLC backbone and the derived cDNA was completely sequenced by Sanger sequencing. Viruses were rescued by reverse genetics, passaged once, and virus stocks at P2 were titrated. Because of the low virus titer of most of the virus stocks, only the mutant virus Min_FLC_M2-1[A73S] was completely sequenced by Sanger sequencing. (B) The is phenotype of some of these Min_FLC-derived mutants was evaluated by efficiency of plaque formation at 32, 35, 36, 37, 38, 39, and 40° C. Plaque assays were performed on Vero cells in duplicate, and incubated in sealed caskets at various temperatures in temperature controlled water-baths as previously described. The experiment was done twice. The median values and the standard deviation is indicated.

Figure 12:
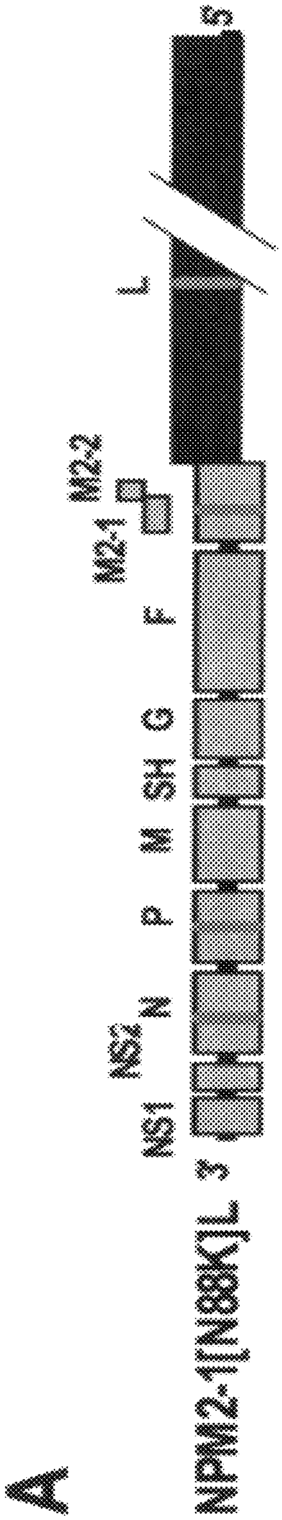
Figure 12:
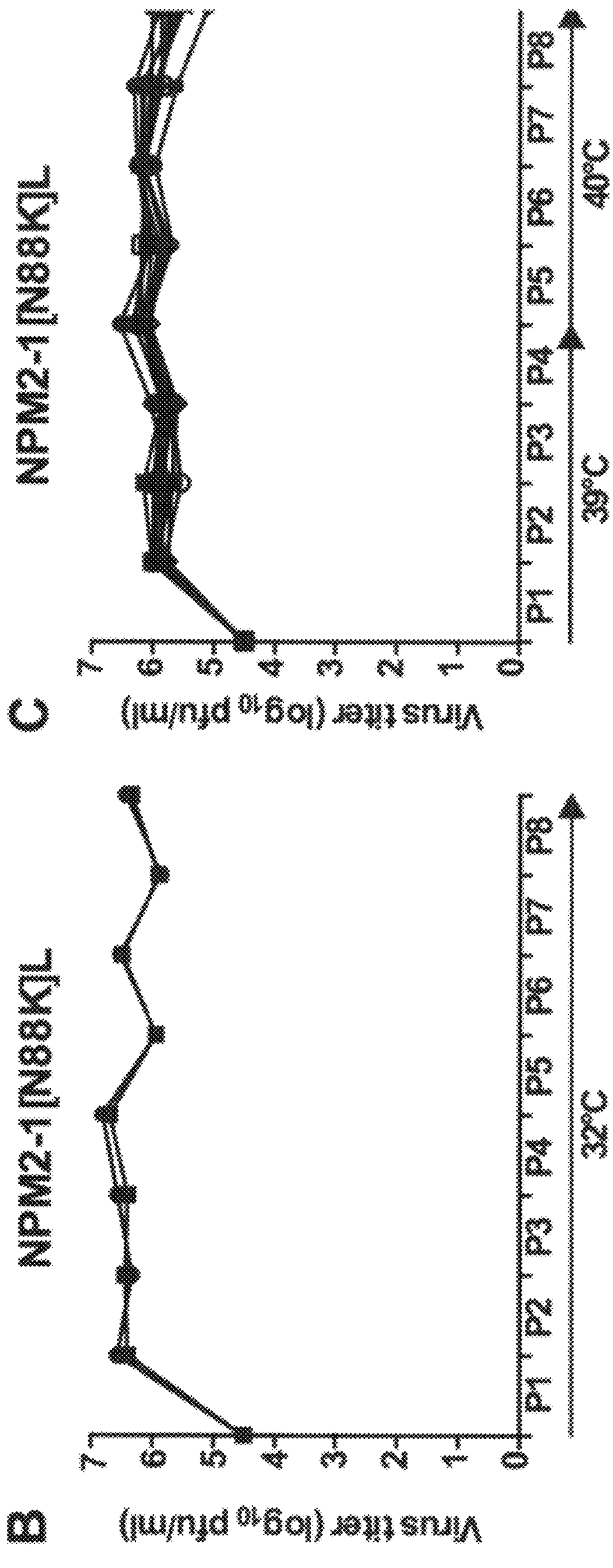

FIG. 12 shows that NPM2-1[N88K]L is phenotypically stable under a temperature stress test. (A) Schematic representation of the RSV genome organization. The abbreviated gene name is indicated. Genes with wt or CPD ORFs are indicted by grey and black shading, respectively. Mutations in N, P, M2-1 and L that were identified in lineage #3 and introduced into Min_L backbone to generate the NPM2-1 [N88K]L virus are indicated by bars in the virus genome. (B) Final virus titers at 32° C. and (C) from the temperature stress passages (increasing temperatures are indicated below the x axis). Each symbol represents one replicate.

FIG. 13 shows the Amino acid sequences of the RSV proteins NS1, NS2, N, P, M, SH, G, F, M2-1, M2-2 and L. These are represented by SEQ ID NO:1-11 respectively.

FIG. 14 shows Nucleotide sequence of recombinant RSV Min_L-NPM2-1[N88K]L. This is represented by SEQ ID NO:14.

DETAILED DESCRIPTION

Provided herein are recombinant RSV strains suitable for use as attenuated, live vaccines in humans. The RSV strains may be produced by introducing one or more mutations in the RSV genome or antigenome sequence selected from the positions described below and listed in tables S1, S2 and S3. These mutations were identified by evaluating phenotypic reversion of de-optimized human respiratory syncytial virus (RSV) vaccine candidates in the context of strong selective pressure.

Codon-pair de-optimized (CPD) versions of RSV were attenuated and temperature-sensitive. During serial passage at progressively increasing temperature, a CPD RSV containing 2,692 synonymous mutations in 9 of 11 ORFs, named Min_FLC, did not lose temperature sensitivity and remained genetically and phenotypically stable during 7 months of passage in vitro at the permissive temperature of 32° C., as well as under conditions of increasing temperature during passage. This is strong evidence for the stability of Min_FLC, and validates the safety of CPD of multiple genes for the development of live-attenuated vaccines for RSV and related viruses, provided that extensive CPD is employed.

However, a CPD RSV in which only the polymerase L ORF was deoptimized, named Min_L, was highly stable at 32° C. but surprisingly, despite the large number of changes involved in its CPD, quickly lost substantial attenuation and evolved to escape temperature sensitivity restriction. Comprehensive sequence analysis of virus populations identified many different potentially de-attenuating mutations in the L ORF, surprisingly many appearing in other ORFs that had not been subjected to CPD. In particular, deep sequencing of the Min_L lineages identified mutations in all but the NS2 ORF, rather than specifically in the CPD L ORF, as might have been expected. Surprisingly, many of the mutations in L occurred at nucleotides and codons that were not involved in CPD. These are shown in tables S1, S2 and S3.

Some of these presumptive de-attenuating mutations, while being de-attenuating in vitro, when incorporated into Min_L with other presumptive de-attenuating mutations, were found to have the surprising effect of being further attenuating than Min_L in vivo.

In one exemplary embodiment, Min_L-NPM2-1[N88K]L (also referred herein as NPM2-1[N88K]L) described in detail below (nucleotide sequence shown in FIG. 14), was more attenuated than Min_L in vivo rather than being de-attenuated. Furthermore, while the NPM2-1[N88K]L virus was highly attenuated in vivo, surprisingly it was as immunogenic as wild type RSV. Additionally, it did not acquire any significant mutations during a further stress test (see FIG. 12), and thus was more genetically stable than Min_L. Thus, Min_L-NPM2-1[N88K]L represented a substantial improvement over Min_L as a vaccine candidate for the following reasons. It was significantly more attenuated in vivo than Min_L, yet as immunogenic as wt RSV. It did not accumulate additional mutations when passaged in stress tests at 39-40° C. It exhibited increased replication compared to Min_L in Vero cells, which is important for vaccine manufacture. Furthermore, as described in detail below, since the M2-1 [N88K] and [A73S] mutations are incompatible, this virus is highly refractory to acquiring the M2-1[A73S] mutation that was de-attenuating in the hamster model.

Accordingly, provided herein are recombinant RSV strains having an attenuated phenotype comprising a RSV genome or antigenome sequence, wherein the RSV genome or antigenome is modified by one or more mutations selected from Table S1, S2 or S3. The mutations listed in Tables S1, S2 or S3 are presumptive de-attenuating mutations but surprisingly may impart attenuation phenotype in vivo. Mutations listed in Tables S1, S2 and S3 present in ≥25% reads are listed in Tables S1-A, S2-A and S3-A respectively, and the most abundant mutations present in ≥50% reads are listed in Tables S1-B, S2-B and S3-B, respectively.

In one embodiment, the invention comprises an isolated polynucleotide molecule encoding a recombinant respiratory syncytial virus (RSV) variant having an attenuated phenotype comprising a RSV genome or antigenome sequence, wherein the RSV genome or antigenome is modified by one or more mutations selected from the positions recited in Table S1. In some embodiments, the RSV genome or antigenome is modified by one or more mutations selected from the positions recited in Table S1-A. In some embodiments, the RSV genome or antigenome is modified by one or more mutations selected from the positions recited in Table S1-B.

In one embodiment, the invention comprises an isolated polynucleotide molecule encoding a recombinant respiratory syncytial virus (RSV) variant having an attenuated phenotype comprising a RSV genome or antigenome sequence, wherein the RSV genome or antigenome is modified by one or more mutations selected from the positions recited in Table S2. In some embodiments, the RSV genome or antigenome is modified by one or more mutations selected from the positions recited in Table S2-A. In some embodiments, the RSV genome or antigenome is modified by one or more mutations selected from the positions recited in Table S2-B.

In one embodiment, the invention comprises an isolated polynucleotide molecule encoding a recombinant respiratory syncytial virus (RSV) variant having an attenuated phenotype comprising a RSV genome or antigenome sequence, wherein the RSV genome or antigenome is modified by one or more mutations selected from the positions recited in Table S3. In some embodiments, the RSV genome or antigenome is modified by one or more mutations selected from the positions recited in Table S3-A. In some embodiments, the RSV genome or antigenome is modified by one or more mutations selected from the positions recited in Table S3-B.

In some embodiments, the RSV genome or antigenome may be modified by a mutation in the L ORF at a position corresponding to or in the codon encoding amino acid residue 1166 of the L protein. In some embodiments, the mutation in the L ORF may be at a position corresponding to T1166 of the L protein as shown in the sequence of FIG. 13 (SEQ ID NO:11). In some embodiments, the mutation may cause an amino acid other than Threonine to be encoded at that position. In some embodiments, the mutation may cause isoleucine to be encoded at that position. This mutation, T1166I is listed in Tables S1, S1-A and S1-B.

In some embodiments, the RSV genome or antigenome may be further modified by one or more additional mutations. The additional mutations may be in the L ORF or any of the other ORFs. For example, in some embodiments, the additional one or more mutations may be in M2-1 ORF, the N ORF or the P ORF.

In some embodiments, the additional mutation may be in the M2-1 ORF at a position corresponding to or in the codon encoding amino acid residue 88 or 73 of the M2-1 protein. In some embodiments, the mutation in the M2-1 ORF may be at a position corresponding to N88 or A73 of the M2-1 protein as shown in sequence of FIG. 13 (SEQ ID NO:9). In some embodiments, the additional mutation in the M2-1 ORF may be at a position corresponding to position N88 of the M2-1 protein, and may cause an amino acid other than asparagine to be encoded at that position. In some embodiments, it may cause lysine to be encoded at that position (N88K). In some embodiments, the additional mutation in the M2-1 ORF may be at a position corresponding to position A73 of the M2-1 protein, and may cause an amino acid other than alanine to be encoded at that position. In some embodiments, the mutation in the codon encoding amino acid residue 73 of the M2-1 protein may cause serine to be encoded at that position (A73S).

In some embodiments, the additional mutation may be in the N ORF at a position corresponding to or in the codon encoding amino acid residue 136 of the N protein. In some embodiments, the mutation in the N ORF may be at a position corresponding to K136 of the N protein as shown in sequence of FIG. 13 (SEQ ID NO:3), and may cause an amino acid other than lysine to be encoded at that position. In some embodiments, the mutation in the codon encoding amino acid residue 136 of the N protein may cause arginine to be encoded at that position (K136R).

In some embodiments, the additional mutation may be in the P ORF at the codon encoding amino acid residue 114 of the P protein. In some embodiments, the mutation in the P ORF may be at a position corresponding to E114 of the P protein as shown in sequence of FIG. 13 (SEQ ID NO:4), and may cause an amino acid other than glutamic acid to be encoded at that position. In some embodiments, the mutation in the codon encoding amino acid residue 136 of the P protein may cause valine to be encoded at that position (E114V).

In some embodiments, the RSV genome or antigenome may be modified to comprise at least two of the mutations described above. For example, it may comprise at least two mutations at positions corresponding to N88 or A73 in M2-1 protein, K136 in the N protein, E114 in the P protein and T1166 in the L protein. In some embodiments, the RSV genome or antigenome may be modified to comprise all four of the mutations described above. Thus, for example, in some embodiments it may comprise mutations at positions corresponding to N88 in M2-1 protein, K136 in the N protein, E114 in the P protein and T1166 in the L protein. In some embodiments it may comprise mutations at positions corresponding to A73 in M2-1 protein, K136 in the N protein, E114 in the P protein and T1166 in the L protein.

In some embodiments, the isolated polynucleotide molecule may comprise a RSV genome or antigenome modified by mutations corresponding to or encoding N88K in M2-1 protein, K136R in the N protein, E114V in the P protein and T1166I in the L protein. In some embodiments, the isolated polynucleotide molecule may comprise a RSV genome or antigenome modified by mutations corresponding to or encoding A73S in M2-1 protein, K136R in the N protein, E114V in the P protein and T1166I in the L protein.

In some embodiments, the RSV genome or antigenome may be deoptimized. Thus, in some embodiments, the attenuated RSVs described herein are produced by introducing codon changes in the viral genome that are not optimally processed by the host cell. The majority of these mutations do not cause a change in the resulting amino acid of proteins encoded by the viral genome, thus allowing for the production of viruses that have the same antigenic features of wild-type viruses. It should be understood, however, that widespread noncoding changes to the codons of the viral genome may result in a selective pressure that gives rise to one or more amino acid mutations in the viruses described herein.

This substitution of synonymous codons alters various parameters, including codon bias, codon pair bias, density of deoptimized codons and deoptimized codon pairs, RNA secondary structure, CpG dinucleotide content, C+G content, translation frameshift sites, translation pause sites, the presence or absence of tissue specific micro RNA recognition sequences, or any combination thereof, in the genome. The main strategies for attenuation by synonymous genome recoding are: codon-deoptimization (CD), codon-pair-deoptimization (CPD), and increasing the dinucleotide CpG and UpA content (which is usually the result of CD and CPD).

In some embodiments, any one of the ORFs of the RSV, including NS1, NS2, N, P, M, SH, G, F, M2-1, M2-2 and L, may be codon-pair deoptimized. In some embodiments, any two or more of the ORFs of the RSV may be codon-pair deoptimized. In some embodiments, any three or more of the ORFs of the RSV may be codon-pair deoptimized. In some embodiments, any four or more of the ORFs of the RSV may be codon-pair deoptimized. In some embodiments, any five or more of the ORFs of the RSV may be codon-pair deoptimized. In some embodiments, any six or more of the ORFs of the RSV may be codon-pair deoptimized. In some embodiments, any seven or more of the ORFs of the RSV may be codon-pair deoptimized. In some embodiments, any eight or more of the ORFs of the RSV may be codon-pair deoptimized. In some embodiments, any nine or more of the ORFs of the RSV may be codon-pair deoptimized. In some embodiments, any ten or more of the ORFs of the RSV may be codon-pair deoptimized. In some embodiments, all of the ORFs of the RSV may be codon-pair deoptimized. In some embodiments, the L ORF of the RSV may be codon-pair deoptimized. In some embodiments, the NS1, NS2, N, P, M and SH ORFs of the RSV may be codon-pair deoptimized. In some embodiments, the G and F ORFs of the RSV may be codon-pair deoptimized. In some embodiments, the NS1, NS2, N, P, M, SH, G, F and L ORFs of the RSV may be codon-pair deoptimized.

In some embodiments, the isolated polynucleotide molecule may comprise a nucleotide sequence that is at least about at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 percent identity (or any percent identity in between) to the nucleotide sequence of SEQ ID NO:14. In some embodiments, the isolated polynucleotide molecule may comprise a nucleotide sequence that is at least about 80% identical to the nucleotide sequence of SEQ ID NO:14. In some embodiments, the isolated polynucleotide molecule may comprise a nucleotide sequence that is at least about 90% identical to the nucleotide sequence of SEQ ID NO:14. In some embodiments, the isolated polynucleotide molecule may comprise a nucleotide sequence that is at least about 95% identical to the nucleotide sequence of SEQ ID NO:14. In some embodiments, the isolated polynucleotide molecule may comprise an isolated polynucleotide comprising the nucleotide sequence of SEQ ID NO:14.

In some embodiments, the described viruses may be combined with known attenuating mutations of RSV and of related viruses to yield graded attenuation phenotypes. A number of such mutations are known in the art and are encompassed in this invention. For example, in some embodiments, the RSV genome or antigenome may be modified by a deletion in the M2-2 ORF, the NS1 ORF or the NS2 ORF.

Given that a variety of RSV strains exist (e.g., RSV A2, RSV B 1, RSV Long), those skilled in the art will appreciate that certain strains of RSV may have nucleotide or amino acid insertions or deletions that alter the position of a given residue. For example, if a protein of another RSV strain had, in comparison with strain A2, two additional amino acids in the upstream end of the protein, this would cause the amino acid numbering of downstream residues relative to strain A2 to increase by an increment of two. However, because these strains share a large degree of sequence identity, those skilled in the art would be able to determine the location of corresponding sequences by simply aligning the nucleotide or amino acid sequence of the A2 reference strain with that of the strain in question. Therefore, it should be understood that the amino acid and nucleotide positions described herein, though specifically enumerated in the context of this disclosure, can correspond to other positions when a sequence shift has occurred or due to sequence variation between virus strains. In the comparison of a protein, or protein segment, or gene, or genome, or genome segment between two or more related viruses, a "corresponding" amino acid or nucleotide residue is one that is thought to be exactly or approximately equivalent in function in the different species.

The numbering used in this disclosure is based on the amino acid sequence of the wild-type RSV A2 strain (GenBank accession number M74568, which is expressly incorporated herein) and all nucleotide sequences described are in positive-sense. The amino acid sequences of the 11 RSV proteins NS1, NS2, N, P, M, SH, G, F, M2-1, M2-2, and L are shown in FIG. 13 and represented in SEQ ID NOS: 1, 2, 3, 4, 5, 6, 7, 8, 9, 10 and 11 respectively.

In some embodiments of the present invention, the recombinant RSV strains may be derived from the recombinant version of strain A2 that is called D46. The complete sequence of D46 is shown in U.S. Pat. No. 6,790,449 (GenBank accession number KT992094, which is expressly incorporated herein). (In some instances and publications, the parent virus and sequence is called D53 rather than D46, a book-keeping difference that refers to the strain of bacteria used to propagate the antigenomic cDNA and has no other known significance or effect. For the purposes of this invention, D46 and D53 are interchangeable.) The nucleotide sequence of D46 differs from the sequence of RSV A2 strain M74568 in 25 nucleotide positions, which includes a 1-nt insert at position 1099.

Additional mutations may be further introduced in combination with the mutations defined above to construct additional viral strains with desired characteristics. For example, the added mutations may specify different magnitudes of attenuation, and thus give incremental increases in attenuation. Thus, candidate vaccine strains can be further attenuated by incorporation of at least one, and preferably two or more different attenuating mutations, for example mutations identified from a panel of known, biologically derived mutant RSV strains. A number of such mutations are discussed here as examples. From this exemplary panel a large "menu" of attenuating mutations can be created, in which each mutation can be combined with any other mutation(s) within the panel for calibrating the level of attenuation and other desirable phenotypes. Additional attenuating mutations may be identified in non-RSV negative stranded RNA viruses and incorporated in RSV mutants of the invention by mapping the mutation to a corresponding, homologous site in the recipient RSV genome or antigenome and mutating the existing sequence in the recipient to the mutant genotype (either by an identical or conservative mutation). Additional useful mutations can be determined empirically by mutational analysis using recombinant minigenome systems and infectious virus as described in the references incorporated herein.

The recombinant RSV vaccine strains of the present invention were made using a recombinant DNA-based technique called reverse genetics (Collins, et al. 1995. Proc Natl Acad Sci USA 92:11563-11567). This system allows de novo recovery of infectious virus entirely from cDNA in a qualified cell substrate under defined conditions. Reverse genetics provides a means to introduce predetermined mutations into the RSV genome via the cDNA intermediate. Specific attenuating mutations were characterized in preclinical studies and combined to achieve the desired level of attenuation. Derivation of vaccine viruses from cDNA minimizes the risk of contamination with adventitious agents and helps to keep the passage history brief and well documented. Once recovered, the engineered virus strains propagate in the same manner as a biologically derived virus. As a result of passage and amplification, the vaccine viruses do not contain recombinant DNA from the original recovery.

The recombinant virus strains that contain various combinations of mutations discussed herein are for exemplary purposes only and are not meant to limit the scope of the present invention. For example, in some embodiments, the recombinant RSV strains of the present invention further comprise a deletion of the non-translated sequences. In one embodiment, such deletion occurs in the downstream end of the SH gene, resulting in a mutation called the "6120 Mutation" herein. It involves deletion of 112 nucleotides of the downstream non-translated region of the SH gene and the introduction of five translationally-silent point mutations in the last three codons and the termination codon of the SH gene (Bukreyev, et al. 2001. J Virol 75:12128-12140). Presence of the term "LID" or "6120" in a recombinant virus name indicates that the recombinant virus contains the 6120 mutation.

The 6120 mutation stabilizes the antigenomic cDNA in bacteria so that it could be more easily manipulated and prepared. In wt RSV, this mutation was previously found to confer a 5-fold increase in replication efficiency in vitro (Bukreyev, et al. 2001. J Virol 75:12128-12140), whereas it was not thought to increase replication efficiency in vivo.

The 6120 mutation was associated with increased replication in seronegative infants and children. Thus, the 6120 mutation provided another means to shift the level of attenuation. Also, the deletion of sequence exemplified by the 6120 mutation in the downstream non-translated region of the SH gene, but in principle could involve any comparable genome sequence that does not contain a critical cis-acting signal (Collins and Karron. 2013. Fields Virology 6th Edition, pp 1086-1123). Genome regions that are candidates for deletion include, but are not limited to, non-translated regions in other genes, in the intergenic regions, and in the trailer region.

In some embodiments the recombinant RSV strains may comprise the "cp" mutation. This mutation refers to a set of five amino acid substitutions in three proteins (N (V267I), F (E218A and T523I), and L (C319Y and H1690Y)) that together (on their own) confer an approximate 10-fold reduction in replication in seronegative chimpanzees, and a reduction in illness (Whitehead, et al. 1998. J Virol 72:4467-4471). We previously showed that the cp mutation is associated with a moderate attenuation phenotype (Whitehead, et al. 1999. J Virol 72:4467-4471).

In addition, previous analysis of 6 biological viruses that had been derived by chemical mutagenesis of cpRSV and selected for the temperature-sensitive (ts) phenotype yielded a total of 6 independent mutations that each conferred a ts attenuation phenotype and could be used in various combinations. Five of these were amino acid substitutions in the L protein, which were named based on virus number rather than sequence position: "955" (N43I), "530" (F521L), "248" (Q831L), "1009" (M1169V), and "1030" (Y1321N) (Juhasz, et al. 1999. Vaccine 17:1416-1424; Collins, et al. 1999. Adv Virus Res 54:423-451; Firestone, et al. 1996. Virology 225:419-422; Whitehead, et al. 1999. J Virol 73:871-877). The sixth mutation (called "404") was a single nucleotide change in the gene-start transcription signal of the M2 gene (GGGGCAAATA to GGGGCAAACA, mRNA-sense) (Whitehead, et al. 1998. Virology 247:232-239). We recently used reverse genetics to increase the genetic stability of the 248 and 1030 mutations (Luongo, et al. 2009. Vaccine 27:5667-5676; Luongo, et al. 2012. J Virol 86:10792-10804). In addition, we created a new attenuating mutation by deleting codon 1313 in the L protein and combining it with an I1314L substitution to confer increased genetic stability (Luongo, et al. 2013. J Virol 87:1985-1996).

In some embodiments, the recombinant strains may comprise one or more changes in the F protein, e.g. the "HEK" mutation, which comprises two amino acid substitutions in the F protein namely K66E and Q101P (described in Connors, et al. 1995. Virology 208:478-484; Whitehead, et al. 1998. J Virol 72:4467-4471). The introduction of the HEK amino acid assignments into the strain A2 F sequence of this disclosure results in an F protein amino acid sequence that is identical to that of an early-passage (human embryonic kidney cell passage 7, HEK-7) of the original clinical isolate of strain A2 (Connors, et al. 1995. Virology 208:478-484; Whitehead, et al. 1998. J Virol 72:4467-4471). It results in an F protein that is much less fusogenic and is thought to represent the phenotype of the original A2 strain clinical isolate (Liang et al. J Virol 2015 89:9499-9510). The HEK F protein also forms a more stable trimer (Liang et al. J Virol 2015 89:9499-9510). This may provide a more authentic and immunogenic form of the RSV F protein, possibly enriched for the highly immunogenic pre-fusion conformation (McLellan et al. Science 2013 340(6136):1113-7; Science 2013 342(6158):592-8.). Thus, mutations can be introduced with effects additional to effects on the magnitude of virus replication.

In some embodiments the recombinant strains may comprise one or more changes in the L protein, e.g. the stabilized 1030 or the "1030s" mutation which comprises 1321K (AAA)/S1313(TCA) (Luongo, et al. 2012. J Virol 86:10792-10804).

In some embodiments the recombinant strains may comprise one or more changes in the N protein, e.g. an amino substitution such as T24A. Deletion of the SH, NS1, and NS2 genes individually and in combination has been shown to yield viruses that retain their ability to replicate in cell culture but are attenuated in vivo in the following order of increasing magnitude: SH<NS2<NS1 (Bukreyev, et al. 1997. J Virol 71:8973-8982; Whitehead, et al. 1999. J Virol 73:3438-3442; Teng, et al. 2000. J Virol 74:9317-9321). Therefore, deletion or other mutations of the SH, NS2, or NS1 genes, or parts of their ORFs, may be combined with a mutation described here. For example, in some embodiments, the recombinant strains may comprise one or more changes in the SH protein, including an ablation or elimination of the SH protein. In some embodiments, the viral strains comprise a deletion in the SH gene. For example, in some embodiments, the viral strains comprise a 419 nucleotide deletion at position 4197-4615 (4198-4616 of), denoted herein as the "ΔSH" mutation. This deletion results in the deletion of M gene-end, M/SH intergenic region, and deletion of the SH ORF as shown in FIG. 6. In some embodiments, the recombinant strains may comprise one or more changes in the NS1 or the NS2 protein, which may include an ablation or elimination of the protein. In some embodiments, the mutation may be an amino substitution such as K51R in the NS2 protein.

Various features can be introduced into RSV strains of the present invention that change the characteristics of the virus in ways other than attenuation. For instance, codon optimization of the ORFs encoding the proteins may be performed. Major protective antigens F and G can result in increased antigen synthesis. The F and/or G protein gene may be shifted upstream (closer to the promoter) to increase expression. The F and/or G protein amino acid sequences can be modified to represent currently-circulating strains, which can be particularly important in the case of the divergent G protein, or to represent early-passage clinical isolates. Deletions or substitutions may be introduced into the G protein to obtain improved immunogenicity or other desired properties. For example, the CX3C fractalkine motif in the G protein might be ablated to improve immunogenicity (Chirkova et al. J Virol 2013 87:13466-13479).

For example, in some embodiments, the nucleotide sequence encoding the G protein of the RSV may be replaced with a nucleotide sequence from the clinical isolate A/Maryland/001/11. In some embodiments, the nucleotide sequence encoding the F protein of the RSV may be replaced with a nucleotide sequence from the clinical isolate A/Maryland/001/11, e.g. F001.

In some embodiments, a native or naturally occurring nucleotide sequence encoding a protein of the RSV may be replaced with a codon optimized sequence designed for increased expression in a selected host, in particular the human. For example, in some embodiments, the nucleotide sequence encoding the F protein of the RSV may be replaced with a codon optimized sequence. In some embodiments, the nucleotide sequence encoding the F protein of the RSV may be replaced with the codon optimized sequence from the clinical isolate A/Maryland/001/11. In some embodiments, the nucleotide sequence encoding the G protein of the RSV may be replaced with the codon optimized nucleotide sequence from the clinical isolate A/Maryland/001/11.

Yet additional aspects of the invention involve changing the position of a gene or altering gene order. For example, the NS1, NS2, SH and G genes may be deleted individually, or the NS1 and NS2 gene may be deleted together, thereby shifting the position of each downstream gene relative to the viral promoter. For example, when NS1 and NS2 are deleted together, N is moved from gene position 3 to gene position 1, P from gene position 4 to gene position 2, and so on. Alternatively, deletion of any other gene within the gene order will affect the position (relative to the promoter) only of those genes which are located further downstream. For example, SH occupies position 6 in Wild type virus, and its deletion does not affect M at position 5 (or any other upstream gene) but moves G from position 7 to 6 relative to the promoter. It should be noted that gene deletion also can occur (rarely) in a biologically-derived mutant virus. For example, a subgroup B RSV that had been passaged extensively in cell culture spontaneously deleted the SH and G genes (Karron et al. Proc. Natl. Acad. Sci. USA 94:13961 13966, 1997; incorporated herein by reference).

Gene order shifting modifications (i.e., positional modifications moving one or more genes to a more promoter-proximal or promoter-distal location in the recombinant viral genome) result in viruses with altered biological properties. For example, RSV lacking NS1, NS2, SH, G, NS1 and NS2 together, or SH and G together, have been shown to be attenuated in vitro, in vivo, or both. In particular, the G and F genes may be shifted, singly and in tandem, to a more promoter-proximal position relative to their wild-type gene order. These two proteins normally occupy positions 7 (G) and 8 (F) in the RSV gene order (NS1-NS2-N-P-M-SH-G-FM2-L). In some embodiments, the order of the nucleotide sequences encoding the G and the F proteins may be reversed relative to the naturally occurring order.

In addition to the above described mutations, the attenuated viruses according to the invention can incorporate heterologous, coding or non-coding nucleotide sequences from any RSV or RSV-like virus, e.g., human, bovine, ovine, murine (pneumonia virus of mice), or avian (turkey rhinotracheitis virus) pneumovirus, or from another enveloped virus, e.g., parainfluenza virus (PIV). Exemplary heterologous sequences include RSV sequences from one human RSV strain combined with sequences from a different human RSV strain. Alternatively, the RSV may incorporate sequences from two or more, wild-type or mutant human RSV subgroups, for example a combination of human RSV subgroup A and subgroup B sequences. In yet additional aspects, one or more human RSV coding or non-coding polynucleotides are substituted with a counterpart sequence from a heterologous RSV or non-RSV virus to yield novel attenuated vaccine strains.

In addition to the recombinant RSVs having the particular mutations, and the combinations of those mutations, described herein, the disclosed viruses may be modified further as would be appreciated by those skilled in the art. For example, the recombinant RSVs may have one or more of its proteins deleted or otherwise mutated or a heterologous gene from a different organism may be added to the genome or antigenome so that the recombinant RSV expresses or incorporates that protein upon infecting a cell and replicating. Furthermore, those skilled in the art will appreciate that other previously defined mutations known to have an effect on RSV may be combined with one or more of any of the mutations described herein to produce a recombinant RSV with desirable attenuation or stability characteristics.

In some embodiments, the mutations described herein, when used either alone or in combination with another mutation, may provide for different levels of virus attenuation, providing the ability to adjust the balance between attenuation and immunogenicity, and provide a more stable genotype than that of the parental virus.

Additional representative viruses from those described in this disclosure may be evaluated in cell culture for infectivity, replication kinetics, yield, efficiency of protein expression, and genetic stability using the methods described herein and illustrated in examples using exemplary recombinant strains. Additional representative strains may be evaluated in rodents and non-human primates for infectivity, replication kinetics, yield, immunogenicity, and genetic stability. While these semi-permissive systems may not reliably detect every difference in replication, substantial differences in particular may be detected. Also recombinant strains may be evaluated directly in seronegative children without the prior steps of evaluation in adults and seropositive children. This may be done, for example, in groups of 10 vaccine recipients and 5 placebo recipients, which is a small number that allows simultaneous evaluation of multiple candidates. Candidates may be evaluated in the period immediately post-immunization for vaccine virus infectivity, replication kinetics, shedding, tolerability, immunogenicity, and genetic stability, and the vaccines may be subjected to surveillance during the following RSV season for safety, RSV disease, and changes in RSV-specific serum antibodies, as described in Karron, et al. 2015, Science Transl Med 2015 7(312):312ra175, which is incorporated herein in its entirety. Thus, analysis of selected representative viruses may provide for relatively rapid triage to narrow down candidates to identify the most optimal.

Reference to a protein or a peptide includes its naturally occurring form, as well as any fragment, domain, or homolog of such protein. As used herein, the term "homolog" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes in one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation. A homolog can have either enhanced, decreased, or substantially similar properties as compared to the naturally occurring protein or peptide. A homolog of a given protein may comprise, consist essentially of, or consist of, an amino acid sequence that is at least about 50%, or at least about 55%, or at least about 60%, or at least about 65%, or at least about 70%, or at least about 75%, or at least about 80%, or at least about 85%, or at least about 90%, or at least about 95%, or at least about 96%, or at least about 97%, or at least about 98%, or at least about 99% identical (or any percent identity between 45% and 99%, in whole integer increments), to the amino acid sequence of the reference protein.

In one aspect of the invention, a selected gene segment, such as one encoding a selected protein or protein region (e.g., a cytoplasmic tail, transmembrane domain or ectodomain, an epitopic site or region, a binding site or region, an active site or region containing an active site, etc.) from one RSV, can be substituted for a counterpart gene segment from the same or different RSV or other source, to yield novel recombinants having desired phenotypic changes compared to wild-type or parent RSV strains. For example, recombinants of this type may express a chimeric protein having a cytoplasmic tail and/or transmembrane domain of one RSV fused to an ectodomain of another RSV. Other exemplary recombinants of this type express duplicate protein regions, such as duplicate immunogenic regions. As used herein, "counterpart" genes, gene segments, proteins or protein regions, are typically from heterologous sources (e.g., from different RSV genes, or representing the same (i.e., homologous or allelic) gene or gene segment in different RSV strains). Typical counterparts selected in this context share gross structural features, e.g., each counterpart may encode a comparable structural "domain," such as a cytoplasmic domain, transmembrane domain, ectodomain, binding site or region, epitopic site or region, etc. Counterpart domains and their encoding gene segments embrace an assemblage of species having a range of size and amino acid (or nucleotide) sequence variations, which range is defined by a common biological activity among the domain or gene segment variants. For example, two selected protein domains encoded by counterpart gene segments within the invention may share substantially the same qualitative activity, such as providing a membrane spanning function, a specific binding activity, an immunological recognition site, etc. More typically, a specific biological activity shared between counterparts, e.g., between selected protein segments or proteins, will be substantially similar in quantitative terms, i.e., they will not vary in respective quantitative activity profiles by more than 30%, preferably by no more than 20%, more preferably by no more than 5-10%.

In alternative aspects of the invention, the infectious RSV produced from a cDNA-expressed genome or antigenome can be any of the RSV or RSV-like strains, e.g., human, bovine, murine, etc., or of any pneumovirus or metapneumovirus, e.g., pneumonia virus of mice or avian metapneumovirus. To engender a protective immune response, the RSV strain may be one which is endogenous to the subject being immunized, such as human RSV being used to immunize humans. The genome or antigenome of endogenous RSV can be modified, however, to express RSV genes or gene segments from a combination of different sources, e.g., a combination of genes or gene segments from different RSV species, subgroups, or strains, or from an RSV and another respiratory pathogen such as human parainfluenza virus (PIV) (see, e.g., Hoffman et al. J. Virol. 71:4272-4277 (1997); Durbin et al. Virology 235(2):323-32 (1997); Murphy et al. U.S. Patent Application Ser. No. 60/047,575, filed May 23, 1997, and the following plasmids for producing infectious PIV clones: p3/7(131) (ATCC 97990); p3/7(131) 2G (ATCC 97889); and p218(131) (ATCC 97991); each deposited Apr. 18, 1997 under the terms of the Budapest Treaty with the American Type Culture Collection (ATCC) of 10801 University Blvd., Manassas, Va. 20110-2209, USA., and granted the above identified accession numbers.

In certain embodiments of the invention, recombinant RSV are provided wherein individual internal genes of a human RSV are replaced with, e.g., a bovine or other RSV counterpart, or with a counterpart or foreign gene from another respiratory pathogen such as PIV. Substitutions, deletions, etc. of RSV genes or gene segments in this context can include part or all of one or more of the NS1, NS2, N, P, M, SH, and L genes, or the M2-1 open reading frames, or non-immunogenic parts of the G and F genes. Also, human RSV cis-acting sequences, such as promoter or transcription signals, can be replaced with, e.g., their bovine RSV counterpart. Reciprocally, means are provided to generate live attenuated bovine RSV by inserting human attenuating genes or cis-acting sequences into a bovine RSV genome or antigenome background.

Thus, infectious recombinant RSV intended for administration to humans can be a human RSV that has been modified to contain genes from, e.g., a bovine RSV or a PIV, such as for the purpose of attenuation. For example, by inserting a gene or gene segment from PIV, a bivalent vaccine to both PIV and RSV is provided. Alternatively, a heterologous RSV species, subgroup or strain, or a distinct respiratory pathogen such as PIV, may be modified, e.g., to contain genes that encode epitopes or proteins which elicit protection against human RSV infection. For example, the human RSV glycoprotein genes can be substituted for the bovine glycoprotein genes such that the resulting bovine RSV, which now bears the human RSV surface glycoproteins and would retain a restricted ability to replicate in a human host due to the remaining bovine genetic background, elicits a protective immune response in humans against human RSV strains.

The ability to analyze and incorporate other types of attenuating mutations into infectious RSV for vaccine development extends to a broad assemblage of targeted changes in RSV clones. For example, any RSV gene which is not essential for growth may be ablated or otherwise modified to yield desired effects on virulence, pathogenesis, immunogenicity and other phenotypic characters. In addition, a variety of other genetic alterations can be produced in a recombinant RSV genome or antigenome for incorporation into infectious recombinant RSV, alone or together with one or more attenuating point mutations adopted from a biologically derived mutant RSV.

As used herein, "heterologous genes" refers to genes taken from different RSV strains or types or non-RSV sources. These heterologous genes can be inserted in whole or in part, the order of genes changed, gene overlap removed, the RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

Deletions, insertions, substitutions and other mutations involving changes of whole viral genes or gene segments in recombinant RSV of the invention yield highly stable vaccine candidates, which are particularly important in the case of immunosuppressed individuals. Many of these mutations will result in attenuation of resultant vaccine strains, whereas others will specify different types of desired phenotypic changes. For example, certain viral genes are known which encode proteins that specifically interfere with host immunity (see, e.g., Kato et al., EMBO. J. 16:578-87 (1997). Ablation of such genes in vaccine viruses is expected to reduce virulence and pathogenesis and/or improve immunogenicity.

Other mutations within RSV of the present invention involve replacement of the 3' end of genome with its counterpart from antigenome, which is associated with changes in RNA replication and transcription. In addition, the intergenic regions (Collins et al., Proc. Natl. Acad. Sci.

USA 83:4594-4598 (1986)) can be shortened or lengthened or changed in sequence content, and the naturally-occurring gene overlap (Collins et al., Proc. Natl. Acad. Sci. USA 84:5134-5138 (1987)) can be removed or changed to a different intergenic region by the methods described herein.

In another embodiment, a sequence surrounding a translational start site (preferably including a nucleotide in the −3 position) of a selected RSV gene is modified, alone or in combination with introduction of an upstream start codon, to modulate RSV gene expression by specifying up- or down-regulation of translation.

Alternatively, or in combination with other RSV modifications disclosed herein, RSV gene expression can be modulated by altering a transcriptional GS signal of a selected gene(s) of the virus. In one exemplary embodiment, the GS signal of NS2 is modified to include a defined mutation to superimpose a is restriction on viral replication.

Yet additional RSV clones within the invention incorporate modifications to a transcriptional GE signal. For example, RSV clones are provided which substitute or mutate the GE signal of the NS1 and NS2 genes for that of the N gene, resulting in decreased levels of readthrough mRNAs and increased expression of proteins from downstream genes. The resulting recombinant virus exhibits increased growth kinetics and increased plaque size, providing but one example of alteration of RSV growth properties by modification of a cis-acting regulatory element in the RSV genome.

In another aspect, expression of the G protein may be increased by modification of the G mRNA. The G protein is expressed as both a membrane bound and a secreted form, the latter form being expressed by translational initiation at a start site within the G gene translational open reading frame. The secreted form may account for as much as one-half of the expressed G protein. Ablation of the internal start site (e.g., by sequence alteration, deletion, etc.), alone or together with altering the sequence context of the upstream start site yields desired changes in G protein expression. Ablation of the secreted form of the G protein also will improve the quality of the host immune response to exemplary, recombinant RSV, because the soluble form of the G protein is thought to act as a "decoy" to trap neutralizing antibodies. Also, soluble G protein has been implicated in enhanced immunopathology due to its preferential stimulation of a Th2-biased response.

In related aspects, levels of RSV gene expression may be modified at the level of transcription. In one aspect, the position of a selected gene in the RSV gene map may be changed to a more promoter-proximal or promoter-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels. In one example, the NS2 gene (second in order in the RSV gene map) is substituted in position for the SH gene (sixth in order), yielding a predicted decrease in expression of NS2. Increased expression of selected RSV genes due to positional changes can be achieved up to 10-fold, 30-fold, 50-fold, 100-fold or more, often attended by a commensurate decrease in expression levels for reciprocally, positionally substituted genes.

In some exemplary embodiments, the F and G genes may be transpositioned singly or together to a more promoter-proximal or promoter-distal site within the (recombinant) RSV gene map to achieve higher or lower levels of gene expression, respectively. These and other transpositioning changes yield novel RSV clones having attenuated phenotypes, for example due to decreased expression of selected viral proteins involved in RNA replication. In yet other embodiments, RSV useful in a vaccine formulation may be conveniently modified to accommodate antigenic drift in circulating virus. Typically the modification will be in the G and/or F proteins. The entire G or F gene, or the segments encoding particular immunogenic regions thereof, is incorporated into the RSV genome or antigenome cDNA by replacement of the corresponding region in the infectious clone or by adding one or more copies of the gene such that several antigenic forms are represented.

Progeny virus produced from the modified RSV cDNA are then used in vaccination protocols against the emerging strains. Further, inclusion of the G protein gene of RSV subgroup B as a gene addition will broaden the response to cover a wider spectrum of the relatively diverse subgroup A and B strains present in the human population.

An infectious RSV clone of the invention may also be engineered according to the methods and compositions disclosed herein to enhance its immunogenicity and induce a level of protection greater than that provided by infection with a wild-type RSV or an incompletely attenuated parental virus or clone. For example, an immunogenic epitope from a heterologous RSV strain or type, or from a non-RSV source such as PIV, can be added by appropriate nucleotide changes in the polynucleotide sequence encoding the RSV genome or antigenome. Recombinant RSV can also be engineered to identify and ablate (e.g., by amino acid insertion, substitution or deletion) epitopes associated with undesirable immunopathologic reactions. In other embodiments, an additional gene may be inserted into or proximate to the RSV genome or antigenome which is under the control of an independent set of transcription signals. Genes of interest may include, but are not limited to, those encoding cytokines (e.g., IL-2 through IL-15, especially IL-2, IL-6 and IL-12, etc.), gamma-interferon, and include those encoding cytokines (e.g., IL-2 through IL-15, especially IL-2, IL-6 and IL-12, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

In addition to the above described modifications to recombinant RSV, different or additional modifications in RSV clones can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

Introduction of the foregoing, defined mutations into an infectious RSV clone can be achieved by a variety of well-known methods. By "infectious clone" is meant cDNA or its product, synthetic or otherwise, which can be transcribed into genomic or antigenomic RNA capable of producing an infectious virus. The term "infectious" refers to a virus or viral structure that is capable of replicating in a cultured cell or animal or human host to produce progeny virus or viral structures capable of the same activity. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA is well-known by those of ordinary skill in the art and has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. A mutated subfragment can then be assembled into the complete antigenome or genome cDNA. Mutations can vary from single nucleotide changes to replacement of large cDNA pieces containing one or more genes or genome regions.

Recombinant RSV may be produced by the intracellular coexpression of a cDNA that encodes the RSV genomic RNA, together with those viral proteins necessary to generate a transcribing, replicating nucleocapsid. Plasmids encoding other RSV proteins may also be included with these essential proteins. Alternatively, RNA may be synthesized in in vitro transcription reactions and transfected into cultured cells.

Accordingly, also described herein are isolated polynucleotides that encode the described mutated viruses, make up the described genomes or antigenomes, express the described genomes or antigenomes, or encode various proteins useful for making recombinant RSV in vitro. Polynucleotides comprising the sequences of any of the SEQ ID NOs described herein are included in the present invention. Further included are polynucleotides comprising sequences that consist or consist essentially of any of the aforementioned sequences, sequences that possess at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 percent identity (or any percent identity in between) to any of the aforementioned SEQ ID NOs, as well as polynucleotides that hybridize to, or are the complements of the aforementioned molecules.

These polynucleotides can be included within or expressed by vectors in order to produce a recombinant RSV. Accordingly, cells transfected with the isolated polynucleotides or vectors are also within the scope of the invention and are exemplified herein. Thus, in some embodiments, the present invention includes a vector comprising the isolated polynucleotide molecules described above. In some embodiments, the present invention includes a cell comprising the isolated polynucleotide molecules described above.

In related aspects of the invention, compositions (e.g., isolated polynucleotides and vectors incorporating an RSV-encoding cDNA) and methods are provided for producing an isolated infectious recombinant RSV bearing an attenuating mutation. Included within these aspects of the invention are novel, isolated polynucleotide molecules and vectors incorporating such molecules that comprise a RSV genome or antigenome which is modified as described herein. Also provided is the same or different expression vector comprising one or more isolated polynucleotide molecules encoding the RSV proteins. These proteins also can be expressed directly from the genome or antigenome cDNA. The vector (s) is/are preferably expressed or coexpressed in a cell or cell-free lysate, thereby producing a mutant RSV particle or subviral particle.

In one aspect, the invention includes a method for producing one or more purified RSV protein(s) is provided which involves infecting a host cell permissive of RSV infection with a recombinant RSV strain under conditions that allow for RSV propagation in the infected cell. After a period of replication in culture, the cells are lysed and recombinant RSV is isolated therefrom. One or more desired RSV protein(s) is purified after isolation of the virus, yielding one or more RSV protein(s) for vaccine, diagnostic and other uses.

The above methods and compositions for producing attenuated recombinant RSV mutants yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2-1 proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell free lysate containing an expression vector which comprises an isolated polynucleotide molecule encoding attenuated recombinant RSV genome or antigenome as described above, and an expression vector (the same or different vector) which comprises one or more isolated polynucleotide molecules encoding the N, P, L and RNA polymerase elongation factor proteins of RSV. One or more of these proteins also can be expressed from the genome or antigenome cDNA. Upon expression the genome or antigenome and N, P, L, and RNA polymerase elongation factor proteins combine to produce an infectious RSV viral or sub-viral particle.

The recombinant RSV of the invention are useful in various compositions to generate a desired immune response against RSV in a host susceptible to RSV infection. Attenuated rRSV strains of the invention are capable of eliciting a protective immune response in an infected human host, yet are sufficiently attenuated so as to not cause unacceptable symptoms of severe respiratory disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

In another aspect of the invention, the recombinant RSV strains may be employed as "vectors" for protective antigens of other pathogens, particularly respiratory tract pathogens such as parainfluenza virus (PIV). For example, recombinant RSV having a T1166I mutation may be engineered which incorporate, sequences that encode protective antigens from PIV to produce infectious, attenuated vaccine virus.

In some embodiments, the invention includes a pharmaceutical composition comprising an immunologically effective amount of the recombinant RSV variant encoded by the isolated polynucleotide molecules described above. In some embodiments, the invention includes a method of vaccinating a subject or a method of inducing an immune response comprising administering the pharmaceutical composition. The composition may be administered by any suitable method, including but not limited to, via injection, aerosol delivery, nasal spray, nasal droplets, oral inoculation, or topical application. In some embodiments, it may be administered by, via injection, aerosol delivery, nasal spray, nasal droplets. The composition may be administered intranasally or subcutaneously or intramuscularly. In some embodiments, it may be administered intranasally. The methods and routes of administration are further described in detail below.

In related aspects, the invention provides a method for stimulating the immune system of an individual to elicit an immune response against RSV in a mammalian subject. The method comprises administering an immunogenic formulation of an immunologically sufficient or effective amount of an attenuated RSV in a physiologically acceptable carrier and/or adjuvant.

In some embodiments, the invention includes a live attenuated RSV vaccine comprising the recombinant RSV variant encoded by the isolated polynucleotide molecules described above. In some embodiments, the invention includes a pharmaceutical composition comprising the RSV vaccine. In a related aspect, the invention includes a method of making a vaccine comprising expressing the isolated polynucleotide molecules described above.

The vaccines may comprise a physiologically acceptable carrier and/or adjuvant and an isolated attenuated recombinant RSV particle or subviral particle. In some embodiments, the vaccine is comprised of an attenuated recombinant RSV having at least one and preferably two or more mutations described herein or other nucleotide modifications to achieve a suitable balance of attenuation and immunogenicity.

To select candidate vaccine viruses from the host of recombinant RSV strains provided herein, the criteria of viability, efficient replication in vitro, attenuation in vivo, immunogenicity, and phenotypic stability are determined according to well-known methods. Viruses which will be most desired in vaccines of the invention must maintain viability, must replicate sufficiently in vitro well under permissive conditions to make vaccine manufacture possible, must have a stable attenuation phenotype, must be well-tolerated, must exhibit replication in an immunized host (albeit at lower levels), and must effectively elicit production of an immune response in a vaccine sufficient to confer protection against serious disease caused by subsequent infection from wild-type virus. Clearly, the heretofore known and reported RSV mutants do not meet all of these criteria. Indeed, contrary to expectations based on the results reported for known attenuated RSV, viruses of the invention are not only viable and more attenuated then previous mutants, but are more stable genetically in vivo than those previously studied mutants.

To propagate a RSV virus for vaccine use and other purposes, a number of cell lines which allow for RSV growth may be used. RSV grows in a variety of human and animal cells. Preferred cell lines for propagating attenuated RS virus for vaccine use include DBSFRhL-2, MRC-5, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by well-known clarification procedures, e.g., centrifugation, and may be further purified as desired using procedures well known to those skilled in the art.

RSV which has been attenuated as described herein can be tested in various well known and generally accepted in vitro and in vivo models to confirm adequate attenuation, resistance to phenotypic reversion, and immunogenicity for vaccine use. In in vitro assays, the modified virus, which can be a multiply attenuated, biologically derived or recombinant RSV, is tested for temperature sensitivity of virus replication or "ts phenotype," and for the small plaque phenotype. Modified viruses are further tested in animal models of RSV infection. A variety of animal models (e.g., murine, cotton rat, and primate) have been described and are known to those skilled in the art.

In accordance with the foregoing description and based on the Examples below, the invention also provides isolated, infectious RSV compositions for vaccine use. The attenuated virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium. For example, attenuated RSV of the invention may be produced by an infected cell culture, separated from the cell culture and added to a stabilizer.

RSV vaccines of the invention contain as an active ingredient an immunogenically effective amount of RSV produced as described herein. Biologically derived or recombinant RSV can be used directly in vaccine formulations. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or in frozen form that is thawed prior to use, or lyophilized, the lyophilized preparation being combined with a sterile solution prior to administration, as mentioned above. The compositions may contain pharmaceutically acceptable auxiliary substances as required to approximate physiological conditions, which include, but are not limited to, pH adjusting and buffering agents, tonicity adjusting agents, wetting agents and the like, for example, sodium acetate, sodium lactate, sodium chloride, potassium chloride, calcium chloride, sucrose, magnesium sulfate, phosphate buffers, HEPES (4-(2-hydroxyethyl)-1-piperazineethanesulfonic acid) buffer, sorbitan monolaurate, and triethanolamine oleate. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Worchester, Mass.), MPL™ (3-O-deacylated monophosphoryl lipid A; RIBI ImmunoChem Research, Inc., Hamilton, Mont.), and interleukin-12 (Genetics Institute, Cambridge, Mass.).

Upon immunization with a RSV vaccine composition, the host responds to the vaccine by producing antibodies specific for RSV virus proteins, e.g., F and G glycoproteins. In addition, innate and cell-mediated immune responses are induced, which can provide antiviral effectors as well as regulating the immune response. As a result of the vaccination the host becomes at least partially or completely immune to RSV infection, or resistant to developing moderate or severe RSV disease, particularly of the lower respiratory tract.

The host to which the vaccine is administered can be any mammal susceptible to infection by RSV or a closely related virus and capable of generating a protective immune response to antigens of the vaccinizing strain. Thus, suitable hosts include humans, non-human primates, bovine, equine, swine, ovine, caprine, lagamorph, rodents, such as mice or cotton rats, etc. Accordingly, the invention provides methods for creating vaccines for a variety of human and veterinary uses.

The vaccine compositions containing the attenuated RSV of the invention are administered to a subject susceptible to or otherwise at risk of RSV infection in an "immunogenically effective dose" which is sufficient to induce or enhance the individual's immune response capabilities against RSV. An RSV vaccine composition may be administered by any suitable method, including but not limited to, via injection, aerosol delivery, nasal spray, nasal droplets, oral inoculation, or topical application. In the case of human subjects, the attenuated virus of the invention is administered according to well established human RSV vaccine protocols (Karron et al. JID 191:1093-104, 2005). Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV specific maternally-derived serum antibodies, which typically are found in the very young. Also, while the parenteral administration of RSV antigens can sometimes be associated with immunopathologic complications, this has never been observed with a live virus.

In some embodiments, the vaccine may be administered intranasally or subcutaneously or intramuscularly. In some embodiments, it may be administered to the upper respiratory tract. This may be performed by any suitable method, including but not limited to, by spray, droplet or aerosol delivery. Often, the composition will be administered to an individual seronegative for antibodies to RSV or possessing transplacentally acquired maternal antibodies to RSV.

In all subjects, the precise amount of RSV vaccine administered and the timing and repetition of administration will be determined by various factors, including the patient's state of health and weight, the mode of administration, the nature of the formulation, etc. Dosages will generally range from about 3.0 $\log_{10}$ to about 6.0 $\log_{10}$ plaque forming units ("PFU") or more of virus per patient, more commonly from about 4.0 $\log_{10}$ to 5.0 $\log_{10}$ PFU virus per patient. In one embodiment, about 5.0 $\log_{10}$ to 6.0 $\log_{10}$ PFU per patient may be administered during infancy, such as between 1 and 6 months of age, and one or more additional booster doses could be given 2-6 months or more later. In another embodiment, young infants could be given a dose of about 5.0 $\log_{10}$ to 6.0 $\log_{10}$ PFU per patient at approximately 2, 4, and 6 months of age, which is the recommended time of administration of a number of other childhood vaccines. In yet another embodiment, an additional booster dose could be administered at approximately 10-15 months of age. In any event, the vaccine formulations should provide a quantity of attenuated RSV of the invention sufficient to effectively stimulate or induce an anti-RSV immune response (an "effective amount").

In some embodiments, the vaccine may comprise attenuated recombinant RSV virus that elicits an immune response against a single RSV strain or antigenic subgroup, e.g., A or B, or against multiple RSV strains or subgroups. In this regard, rRSV can be combined in vaccine formulations with other RSV vaccine strains or subgroups having different immunogenic characteristics for more effective protection against one or multiple RSV strains or subgroups. They may be administered in a vaccine mixture, or administered separately in a coordinated treatment protocol. to elicit more effective protection against one RSV strain, or against multiple RSV strains or subgroups.

The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates measured by flow cytometry or for cytotoxic activity against indicator target cells displaying RSV antigens. In this regard, individuals are also monitored for signs and symptoms of upper respiratory illness.

In some embodiments, neonates and infants are given multiple doses of RSV vaccine to elicit sufficient levels of immunity. Administration may begin within the first month of life, and at intervals throughout childhood, such as at two months, four months, six months, one year and two years, as necessary to maintain sufficient levels of protection against natural RSV infection. In other embodiments, adults who are particularly susceptible to repeated or serious RSV infection, such as, for example, health care workers, day care workers, family members of young children, the elderly, individuals with compromised cardiopulmonary function, are given multiple doses of RSV vaccine to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered RSV strain expressing a cytokine or an additional protein rich in T cell epitopes may be particularly advantageous for adults rather than for infants. Vaccines produced in accordance with the present invention can be combined with viruses of the other subgroup or strains of RSV to achieve protection against multiple RSV subgroups or strains, or selected gene segments encoding, e.g., protective epitopes of these strains can be engineered into one RSV clone as described herein. In such embodiments, the different viruses can be in admixture and administered simultaneously or present in separate preparations and administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

The level of attenuation of vaccine virus may be determined by, for example, quantifying the amount of virus present in the respiratory tract of an immunized host and comparing the amount to that produced by wild-type RSV or other attenuated RS viruses which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RSV in the nasopharynx of an infected host are well known in the literature. Specimens are obtained by aspiration or washing out of nasopharyngeal secretions and virus quantified in tissue culture or other by laboratory procedure. See, for example, Belshe et al., J. Med. Virology 1:157-162 (1977), Friedewald et al., J. Amer. Med. Assoc. 204:690-694 (1968); Gharpure et al., J. Virol. 3:414-421 (1969); and Wright et al., Arch. Ges. Virusforsch. 41:238-247 (1973). The virus can conveniently be measured in the nasopharynx of host animals, such as chimpanzees.

The invention also provides methods for producing an infectious RSV from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, Land M2-1 protein.

A native RSV genome typically comprises a negative-sense polynucleotide molecule which, through complementary viral mRNAs, encodes eleven species of viral proteins, i.e., the nonstructural proteins NS1 and NS2, N, P, matrix (M), small hydrophobic (SH), glycoprotein (G), fusion (F), M2-1, M2-2, and L, substantially as described in Mink et al., Virology 185: 615-624 (1991), Stec et al., Virology 183: 273-287 (1991), and Connors et al., Virol. 208:478-484 (1995). For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Additional RSV proteins needed for a productive infection can also be supplied by coexpression.

Alternative means to construct cDNA encoding the genome or antigenome include by reverse transcription-PCR using improved PCR conditions (e.g., as described in Cheng et al., Proc. Natl. Acad. Sci. USA 91:5695-5699 (1994); Samal et al., J. Virol 70:5075-5082 (1996)) to reduce the number of subunit cDNA components to as few as one or two pieces. In other embodiments, different promoters can be used (e.g., T3, SP6) or different ribozymes (e.g., that of hepatitis delta virus). Different DNA vectors (e.g., cosmids) can be used for propagation to better accommodate the large size genome or antigenome.

The N, P, L and M2-1 proteins may be encoded by one or more expression vectors which can be the same or separate from that which encodes the genome or antigenome, and various combinations thereof. Additional proteins may be included as desired, encoded by its own vector or by a vector encoding a N, P, L, or M2-1 protein or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., Virology, 210:202-205 (1995)). The viral proteins, and/or T7 RNA polymerase, can also be provided from transformed mammalian cells, or by transfection of preformed mRNA or protein.

In summary, the materials, information, and methods described in this disclosure provide an array of attenuated strains with graded attenuation phenotypes, and provide guidance in selecting suitable vaccine candidate strains based on clinical benchmarks.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims. The examples below are provided for the purpose of illustration and are not intended to limit the scope of the present invention.

Each publication, sequence or other reference disclosed below and elsewhere herein is incorporated herein by reference in its entirety, to the extent that there is no inconsistency with the present disclosure. The disclosures of U.S. Provisional Application 62/399,133 filed Sep. 23, 2016 entitled Improved codon-pair-deoptimized vaccine candidates for human respiratory syncytial virus; U.S. Provisional Application 62/400,476 filed Sep. 27, 2016 entitled Vaccine candidates for respiratory syncytial virus (RSV) having attenuated phenotypes; and Published U.S. application US 2015-0368622 entitled Attenuation of human respiratory syncytial virus by genome scale codon-pair deoptimization are incorporated in their entirety by reference.

EXAMPLES

Materials and Methods

The following materials and methods were used in the examples below.

Virus harvest and titration. Vero cells were scraped into the tissue culture medium, vortexed for 30 sec, clarified by low speed centrifugation, and snap-frozen. Virus titers in the clarified fluids were determined by immunoplaque assay on Vero cells at 32° C.

Virus stocks were generated by scraping infected cells into media, followed by vortexing for 30 sec, clarification of the supernatant by centrifugation. Virus aliquots were snap frozen and stored at −80° C. Virus titers were determined by plaque assay on Vero cells with an 0.8% methylcellulose overlay. After a 10 to 12-day incubation at 32° C., plates were fixed with 80% cold methanol, and plaques were visualized by immunostaining with a cocktail of three RSV-specific monoclonal antibodies. Titers were expressed as pfu per ml. Viral RNA was isolated from all virus stocks, and sequence analysis of the viral genomes was performed from overlapping RT-PCR fragments by Sanger sequencing, confirming that the genomic sequences of the recombinant viruses were correct and free of adventitious mutations. The only sequences that were not directly confirmed for each genome were the positions of the outer-most primers, namely nucleotides 1-23 and 15,174-15,222.

Ion torrent deep sequencing. Purified viral RNA from clarified culture fluids was copied into 8 overlapping fragments spanning the viral genome. Libraries were prepared following the Ion torrent protocol, loaded into a semiconductor sequencing chip, and sequenced on a Personal Genome Machine (Ion Torrent). A nucleotide variant was called if it occurred >50 times with an average read depth of 1000× and a P-value <10-7 (Quality score >70).

Viral RNAs were extracted using the Qiagen Viral RNA extraction kit from the indicated aliquots of viruses that were passed during the temperature stress test of Min_L or Min_FLC. Viral RNAs were reverse transcribed using the superscript II RT (Life Technologies) following the manufacturer recommendations. Then, the cDNAs were amplified by PCR using RSV specific primers and the pfx DNA polymerase enzyme (Life Technologies) in eight overlapping fragments that cover the whole viral genome. Each PCR product was purified using the QIAquick PCR purification kit (Qiagen).

Equal amounts of DNA from each of the eight PCR reactions were pooled into a 1.5 ml LoBind tube (Eppendorf). The DNA was subjected to enzymatic shearing using the ShearEnzyme (Ion Torrent) for 30 min at 37° C. in a heat block. The sheared DNA was then purified using 1.8 volumes of Agencourt magnetic beads (Beckman). The Agencourt beads were washed twice with 0.2 ml of 70% ethanol, air dried for 5 min, and re-suspended with 20-30 μl of 10 mM Tris-HCl pH7.5 buffer followed by incubation at room temperature for 5 min. DNA was recovered in the supernatant by placing the 1.5 ml LoBind tube containing the Agencourt beads on a magnetic rack for 2 minutes (min). The DNA was treated with end-repairing enzyme (Ion Torrent) according to the manufacturer's instructions. The end-repaired DNA was purified with 1.8 volumes of Agencourt beads and recovered in a magnetic rack as described above.

Approximately 100 ng of repaired DNA from each sample were used to ligate with a specific barcode adapter and a sequencing adaptor in a 20 μl reaction volume containing ligase and buffer (Ion Torrent) according to the manufacturer's instruction. The ligation reaction was carried out at room temperature for 30 min and terminated by adding 4 μl of 0.5M EDTA pH8.0. Equal volumes of different ligated DNA libraries were then combined in a 1.5 ml LoBind tube and purified with 1.8 volumes of Agencount and the DNA libraries were recovered as described above. The DNA further underwent nick-translation using Bst 2.0 DNA polymerase and buffer (NEB). Digested DNA was purified using a spin column MinElute kit (Qiagen).

Approximately 100 ng of the DNA libraries were then added into a PCR mix using the Platinum High Fidelity DNA polymerase master mix (Life Technologies) followed by 2 cycles of PCR amplification at 95° C. for 10 min followed by 2 cycles at 95° C. for 30 sec, 58° C. for 30 sec, and 72° C. for 30 sec. The PCR products were further purified with 1.8 volume of Agencourt and DNA was recovered using a magnetic rack as described above. The DNA was quantified using the Qubit system (Invitrogen).

Approximately 70 million DNA molecules in 1 ml of PCR solution were mixed with a fixed ratio (0.5-1.0) of Ion sphere particles (ISP) (Ion Torrent) in the presence of PCR reaction mix and oil (Ion Torrent) to form tens of millions of droplets of emulsion particles. These droplets were passed through an enclosed capillary PCR plate in OneTouch (Ion Torrent) which carried out the emulsion PCR amplification as the liquid and particles pass through the plate continuously. The ISPs were recovered by centrifugation in OneTouch in a pair of collection tubes. At the end of the OneTouch emulsion PCR, the collection tubes were centrifuged for 3 min at 15,000 g to remove most supernatant. The ISPs were washed once in 1 ml wash buffer (Ion Torrent) and centrifuged for 3 min at 15,500 g to remove most supernatant. ISPs containing amplified DNA were further enriched from ISPs without DNA by incubating with Dynabeads® MyOne™ Streptavidin Cl magnetic beads at room temperature for 10 min in a rotating rack. The enriched IPSs were recovered by placing the tube on a magnetic rack for 2 min, washed twice with 0.2 ml of wash buffer by pipetting and placing on a magnetic rack for 2 min and by discarding the supernatant. The ISPs were eluted from the Dynabeads® MyOne™ Streptavidin Cl magnetic beads by incubation with 0.4 ml 0.125N NaOH and 0.1% Tween 20 for 7 min at room temperature in a rotating rack. The eluted ISPs were washed twice with wash buffer and centrifuged for 4 min at 15,500 g to remove most supernatant. The ISPs were resuspended by pipetting and placed on a magnetic rack for 2 min to remove last traces of Dynabeads® MyOne™ beads.

100 μl of solution was transferred to a new tube as the final library of ISPs ready for QC testing and sequencing. For sequencing, the ISPs were centrifuged for 3 min at 15,500 g to remove most of the supernatant. The ISPs were resuspended by pipetting and transferred into a 0.2 ml PCR tube containing 150 μl annealing buffer. Five microliter Control Ion Spheres™ (Ion Torrent) was added to the ISPs mix and centrifuged for 3 min at 15,500 g to remove most supernatant from the top to leave 15 μl at the bottom followed by adding 12 μl sequencing primer, denatured and annealed at 95° C. for 2 min, and 2 min at 37° C. 3 μl DNA polymerase (Ion Torrent) was added, and samples were loaded into a semiconductor sequencing chip 316 or 318 (Ion Torrent) to perform DNA sequencing on a Personal Genome Machine (PGM) (Ion Torrent).

DNA sequences were analyzed against Min_FLC or Min_L reference sequences using VariantCaller 3.2 software from Ion Torrent on the Ion Torrent Server. The analysis pipeline was set at the default somatic variant configuration. A nucleotide variant was called if the variant occurred >50 times with an average read depth of 1000× and a P-value $<10^{-7}$ (Quality score >70) as previously described. The raw read data were also manually verified using a genome browser IVG (The Broad Institute).

Deep sequencing of long PCR fragments. Purified viral RNA from culture fluids was reverse transcribed using the Maxima H minus first strand cDNA synthesis kit (Thermo Scientific). Using RSV specific primers and the SequalPrep long PCR kit (Life Technologies), the cDNAs were used to generate a PCR product of 8.2 kb spanning the genome from the 3' end to the middle of the M2-2 ORF. DNA template libraries were prepared, sequenced, and analyzed using PacBio kits and instrumentation and CluCon software.

The coexistence or not of mutations that arose in the M2-1 and P genes during the first 4 passages of Min_L lineage #3 at 38 and 39° C. was investigated by deep sequencing. To do so, viral RNAs from aliquots of viruses derived from these passages were extracted using the Qiagen viral extraction kit as described above. Then, the viral RNAs were reverse transcribed using the Maxima H minus first strand cDNA synthesis kit (Thermo Scientific) following the manufacturer recommendations. Using RSV specific primers and the SequalPrep long PCR kit (life technologies), cDNAs were then used to generate a PCR product of 8.2 kb that covered a region from the 3' end of the genome to the M2-2 gene.

To prepare PacBio SMRTbell DNA template libraries, PCR products were purified as described above and then concentrated using 0.45 volumes of AMPure PB magnetic beads. To allow the DNA to bind to beads, the mixture was mixed in a VWR vortex mixer at 2000 rpm for 10 min at room temperature. After a short spinning to pellet beads, each tube was placed in a magnetic bead rack and the supernatant was carefully discarded. Beads were then washed twice with 1.5 ml of freshly prepared 70% ethanol. After removal of the ethanol, the bead pellet was allowed to dry for about 1 min. Then, the tube was removed from the magnetic bead rack and centrifuged to pellet the beads. DNA was then eluted using the Pacific Biosciences Elution Buffer. To repair any DNA damage, the concentrated DNA was incubated at 37° C. for 20 min in a LoBind tube in DNA damage repair buffer, NAD+, ATP high, dNTP and a DNA damage repair enzyme mix. Then, DNA was then incubated at 25° C. for 5 min with a DNA end repair mix. After the reaction, DNA was purified using AMPure PB beads as described above, and eluted off the beads in 30 μl of elution buffer.

Then, end repaired DNA was annealed with a blunt end adapter in a reaction containing the adapter, buffer, ATP and a ligase for 15 min at 25° C. Ligase was inactivated at 65° C. for 10 min. Finally an exonuclease step for 1 h at 37° C. was included to remove any failed ligation products. SMRTbell DNA template libraries were then purified three times using AMPure PB beads as described above.

After purification, SMRTbell library templates were sequenced in SMRTcells with the PacBio RSII instrument using the PacBio DNA Polymerase Binding Kit P6. Each sample library was sequenced on 2 SMRTcells using MagBead loading and movie collection time of 240 minutes.

Data were analyzed using CluCon software. All reads were aligned to the reference Min_L sequence. Only reads that span 99% of the full target (8161 bases or greater) were analyzed; yielding 32,738 near-full-length reads per time point on average (minimum 24,131 reads, maximum 41,118 reads). The algorithm identifies variant positions by examining the alignments and finding positions where the minor frequencies observed cannot be explained statistically by chance noise. Fully-phased haplotypes are then estimated by tallying what was sequenced in each of the near-full length reads at the variant positions. A statistical test is used to discard "noisy" haplotypes or those that are simply explained by other true observed haplotypes that have been corrupted by sequencing noise.

Determination of the temperature shut-off of CPD rRSVs. The is phenotype of each of the rRSV viruses was evaluated by efficiency of plaque formation at 32, 35, 36, 37, 38, 39, and 40° C. Plaque assays were performed on Vero cells in duplicate, and incubated in sealed caskets at various temperatures in temperature controlled water-baths as previously described. The shut-off temperatures ($T_{SH}$) is defined as the lowest restrictive temperature at which there is a reduction in plaque number compared to 32° C. that is 100-fold or greater than that observed for wt RSV at the 2 temperatures.

Kinetics of virus replication in vitro. Multi-cycle and single cycle growth kinetics were performed on confluent monolayers of Vero cells at both 32 and 37° C. in six-well plates.

In the multi-cycle growth kinetic experiments, Vero cells were infected in duplicate at an MOI of 0.01 pfu/cell with the indicated viruses. From day 0 to 14, viruses were collected by scraping infected cells into media followed by vortexing for 30 sec, clarification of the supernatant by centrifugation. Virus inoculum and the daily aliquots were snap frozen and stored at −80° C. Virus titers were determined by plaque assay as described above.

In the single cycle growth kinetic experiments, three wells of Vero cells in 6-well plates were infected at an MOI of 3 pfu/well at 32 or 37° C. with the indicated viruses. Every four hours from four to 24 h post-infection, cell-associated RNA was collected from one well using the RNeasy mini kit (Qiagen) following the manufacturer's instructions. For Western blot analysis, total cell lysates were collected in NuPage LDS sample buffer (Life Technologies) and then homogenized using a QIAshredder spin column (Qiagen). Finally, the last well was used to collect virus and determined the virus titers, as described above.

Strand specific rRSV RNA quantification. Cell-associated RNA derived from single cycle replication experiments was used to specifically quantify viral negative sense (genomic) and positive sense (mRNA and antigenomic) RNA as described previously. qPCR results were analyzed using the comparative threshold cycle (ΔCt) method, normalized to 18S rRNA, and then expressed as log 2 fold increase over the indicated reference sample.

Cell-associated RNA derived from single cycle replication experiments was used to specifically quantify viral negative sense (genomic) and positive sense (mRNA and antigenomic) RNA as described previously. Taqman assays for antigenomic/mRNA specific for each of the 11 wt RSV genes were designed using Primer Express 3.0 software (Life Technologies). Specifically, for the L gene, three different taqman assays were designed for the wt sequence and four for the CPD sequence.

One microgram of DNA-digest RNA was reverse transcribed using Superscript III (Life Technologies) in a 20 μl reaction using a tagged first strand primers, specific either to genome or to antigenomic/mRNA. After a five-fold dilution, each of the cDNAs was amplified in triplicate with a tag-specific primer, a second gene-specific primer, and a probe. Thus, only cDNAs containing the tagged RT primer sequence were amplified. The probe sequence was RSV gene-specific. To normalize results, 18S rRNA was quantified in parallel using first strand cDNA generated with random primers, and a standard 18S rRNA taqman assay (Applied Biosystems). qPCR results were analyzed using the comparative threshold cycle (ΔCt) method, normalized to 18S rRNA, and then expressed as $log_2$ fold increase over the Min_L 4 h time point, with the exception of wt L quantification, for which data was expressed as fold increase over the wt 4 h time point. Negative controls without first strand primer were included for each of the strand-specific qPCRs to demonstrate the absence of non-specific priming during first strand cDNA synthesis.

Western blot analysis. Cell lysates prepared from single cycle infection experiments described above were separated on NuPAGE 4-12% Bis-Tris SDS-PAGE gels with MES electrophoresis buffer (Life Technologies) in parallel with Odyssey Two-Color Protein Molecular Weight Marker (Li-Cor). 30 μg of proteins were transferred to PVDF-F membranes (Millipore) in 1× NuPAGE buffer. The membranes were blocked with Odyssey blocking buffer (LI-COR) and incubated with primary antibody in presence of 0.1% Tween-20. The primary antibodies and the dilutions used were as follows: mouse anti-RSV N, P, G, F and M2-1 monoclonal antibodies (1:1,000) were purchased from Abcam; rabbit polyclonal antiserum that recognized both NS1 and NS2 was generated by peptide immunization of rabbits (Abgent) with a synthetic peptide representing the C-terminal 14 amino acids of NS2 (the C-termini of NS2 and NS1 are identical for the last 4 amino acids, which presumably accounts for the cross-reactivity); rabbit anti-GAPDH polyclonal antibody (1:200) used as loading control (Santa-Cruz Biotechnologies, Inc.). The secondary antibodies used at a 1:15,000 dilution were goat anti-rabbit IgG IRDye 680 (Li-Cor) and goat anti-mouse IgG IRDye 800 (Li-Cor). Membranes were scanned on the Odyssey® Infrared Imaging System. Data was analyzed using Odyssey software, version 3.0 (Li-Cor). For quantification of identified RSV proteins of interest, fluorescence signals were background corrected. Values indicate the median fluorescence intensity of each protein band.

Determination of plaques sizes. Virus plaque sizes were determined by plaque assay on Vero cells using twenty-four well plates. Vero cells monolayers were inoculated with 30 pfu per well of previously tittered and sequenced virus stocks. After 2 h adsorption, a 0.8% methylcellulose overlay was added to each well. After a 12-day incubation at 32° C., plates were fixed with 80% cold methanol. Then, wells were incubated with a cocktail of three RSV-specific monoclonal antibodies (Bukreyev et al. 2001) in blocking buffer (Odyssey buffer, Licor) for one hour. After washing with blocking buffer, plaques were stained with goat anti-mouse IRdye 680LT (Licor) secondary antibody, and plaques were visualized using the Odyssey® Infrared Imaging System. Images were analyzed using Image J and the area of more than 1000 plaques per virus was measured and expressed in pixel2. Distribution of the virus plaque sizes was compared for statistical significance using the Kolmogorov-Smirnov test followed by Bonferroni correction (Prism 6.0, GraphPad). Sets of data were only considered statistically different at $p \leq 0.05$.

Evaluation of the replication of CPD rRSVs in mice and hamsters Animal studies were approved by the NIAID Animal Care and Use Committee, and performed using previously described methods.

All animal studies were approved by the National Institutes of Health (NIH) Institutional Animal Care and Use Committee (ACUC). Replication of CPD viruses was evaluated in the upper and lower respiratory tract of six-week-old BALB/c mice as described previously. Group of 20 mice were inoculated intranasally under isoflurane anesthesia with $10^6$ pfu of wt rRSV, Min_L, M2-1[A73S], M2-1[N88K] or NPM2-1[N88K]L. On days 4 and 5, eight mice from each group were sacrificed by carbon dioxide inhalation. The remaining four mice in each group were sacrificed on day 10. Nasal turbinates (NT) and lung tissues were harvested and homogenized separately in Leibovitz (L)-15 medium containing 1×SPG, 2% L-glutamine, 0.06 mg/mL ciprofloxacin, 0.06 mg/mL clindamycin phosphate, 0.05 mg/mL gentamycin, and 0.0025 mg/mL amphotericin B. Virus titers were determined in duplicate on Vero cells incubated at 32° C. as described above. The limit of virus detection was 100 and 50 pfu/g for the NT and lung specimens, respectively.

Replication of CPD viruses was evaluated in the upper and lower respiratory tract of six-week-old Golden Syrian hamsters and immunogenicity was also investigated. On day 0, groups of 18 hamsters were inoculated intranasally under methoxyflurane anesthesia with $10^6$ pfu of wt rRSV, Min_L, M2-1[A73S], M2-1[N88K] or NPM2-1[N88K]L.

On day 3, which corresponds to the peak of replication of wt rRSV in hamsters, 9 hamsters from each group were sacrificed by carbon dioxide inhalation. NT and lung tissue were harvested and homogenized as described above. Virus titers were determined in duplicate on Vero cells incubated at 32° C. as described above. The limit of virus detection was 50 pfu/g in the NTs and lungs.

Two days before immunization and on day 26 post-immunization, blood from nine hamsters per group was collected for serum collection and to measure of RSV antibody titers. On day 31, the hamsters were challenged by intranasal administration of $10^6$ pfu of wt rRSV. Three days after challenge the hamsters were sacrificed by carbon dioxide inhalation. NT and lung tissue were harvested and wt rRSV titers were determined in duplicate on Vero cells incubated at 32° C. as described above.

Molecular dynamics analysis of M2-1 tetramer. Mutations were introduced to the crystal structure of the transcription antiterminator M2-1 protein of human RSV (PDB ID 4C3D) using the SYBYL program (Certara). Molecular dynamics simulations were performed using the NAMD program (v.2.9).

Mutations were made to the crystal structure of the transcription antiterminator M2-1 protein of human RSV (PDB ID 4C3D) using the SYBYL program (Certara, St. Louis, Mo.). Mutants or wt RSV M2-1 were explicitly solvated with TIP3P water molecules and $Na^+$ and $Cl^-$ counterions using the VMD program. All atom, isobaric-isothermal (1 atm, 310 K) molecular dynamics simulations were performed with periodic boundary conditions using the NAMD program (v.2.9) on the Biowulf Linux cluster at the National Institutes of Health, Bethesda, Md. after explicitly solvating and energy minimizing followed by warming to 310 K in 10 K increments. Electrostatic interactions were calculated using the Particle-Mesh Ewald summation. The CHARMM27 force field was used with CHARMM atom types and charges. For all simulations, a 2 fsec integration time step was used along with a 12 Å cutoff. Langevin dynamics were used to maintain temperature at 310 K and a modified Nosé-Hoover Langevin piston was used to control pressure. Simulations were run for 100 nsec.

Statistical analysis. Distribution of the plaques sizes were analyzed using Kolmogorov-Smirnov test followed by Bonferroni correction. Virus replication and antibody responses in the animal experiments were analyzed using the nonparametric Kruskal-Wallis test with Dunn's post hoc analysis. A log 10 transformation was applied to data sets when necessary to obtain equal standard deviation among groups. Statistics were performed using Prism 6 (GraphPad Software). Data were only considered significant at $p<0.05$.

Example 1: Generation of the Min_L and Min_FLC RSV Constructs

The design of the CPD RSV genes and the construction and rescue of Min_L and Min_FLC have been described previously in U.S published application US 2015-0368622 and in Le Nouen et al. (2014). Briefly, previously described computational algorithms (Coleman et al. 2008 and Mueller et al. 2010) were used to design CPD ORFs based on the RSV strain A2. Min_L contains the CPD L ORF, which exhibits 1,378 silent mutations compared to wild-type (wt) L ORF. Min_FLC (for full-length clone) contained all CPD ORFs except M2-1 and M2-2, which were kept unmodified because these overlapping ORFs engage in coupled stop-start translation that depends on sequence (and possibly secondary structure) that is presently incompletely defined. Min_FLC contains 2,692 silent mutations compared to wt RSV (FIG. 1, panel (A)). The amino acid sequence of Min_L and Min_FLC is identical to that of wt RSV. The viruses were constructed using the RSV 6120 backbone, which has a 112-nt deletion in the downstream NTR of the SH gene and 5 silent nucleotide point mutations involving the last three codons and termination codon of the SH ORF. These changes in the SH gene stabilized the RSV cDNA during propagation in *E. coli* (Bukreyev et al. 2004). Wt RSV in this study was the 6120 virus. Min_L and Min_FLC virus stocks were completely sequenced by Sanger and Ion Torrent deep sequencing and found free of adventitious mutations. The nucleotide sequence of Min_FLC is presented in SEQ ID NO:12 and that of Min_L is presented in SEQ ID NO:13.

Example 2: Codon-Pair Deoptimization (CPD) of Multiple RSV Genes Yielded a Very Stable Temperature Sensitive (Ts) Phenotype Restricted to Replication at 32-34° C.

Figure 1:
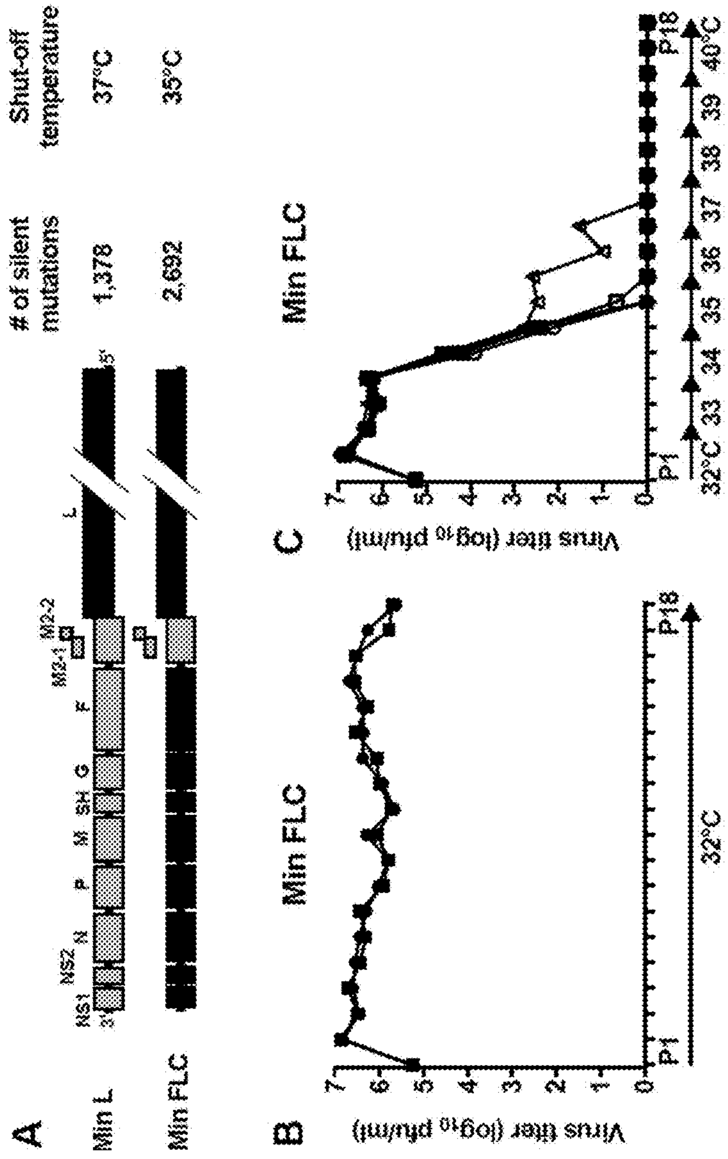
FIG. 1 shows that Min_FLC was phenotypically stable during a temperature stress test, but Min_L was not. (A) Gene maps of Min_L and Min_FLC showing ORFs that are wt (grey) or CPD (black). The number of introduced mutations in each virus and the shut-off temperature ($T_{SH}$) in Vero cells are indicated. (B-E) Incubation temperature and virus yield at each passage level during serial passage in temperature stress tests. Replicate cultures of Vero cells in T25 flasks were infected with the indicated virus at MOI 0.1 and, when the viral cytopathic effect was extensive, or when cells started to detach (for passages of Min_FLC at 37° C. and beyond, (C)), flasks were harvested and clarified culture fluids were passaged 1:5 to a fresh flask. Each starting replicate flask initiated an independent serial passage (lineage). Aliquots of clarified culture fluids were frozen for titration and sequence analysis. (B, C) Temperature stress test of Min_FLC. Two control flasks inoculated with Min_FLC (B) were passaged 18 times at the permissive temperature of 32° C. Ten additional replicates (C) were passaged from 32 to 40° C. with 2 passages at each temperature. (D, E) Temperature stress test of Min_L. Two control flasks inoculated with Min_L (D) were passaged 8 times at the permissive temperature of 32° C. Ten additional replicates (E) were passaged from 37 to 40° C. with 2 passages at each temperature. Lineages #3 and 8 are shown. (F, G) Accumulation of most abundant mutations (>30% of the reads in at least one passage) in lineages #3 (F) and #8 (G) during the passage series, determined by deep sequencing (see Tables S2 and S3 for detailed data).
Figure 1:
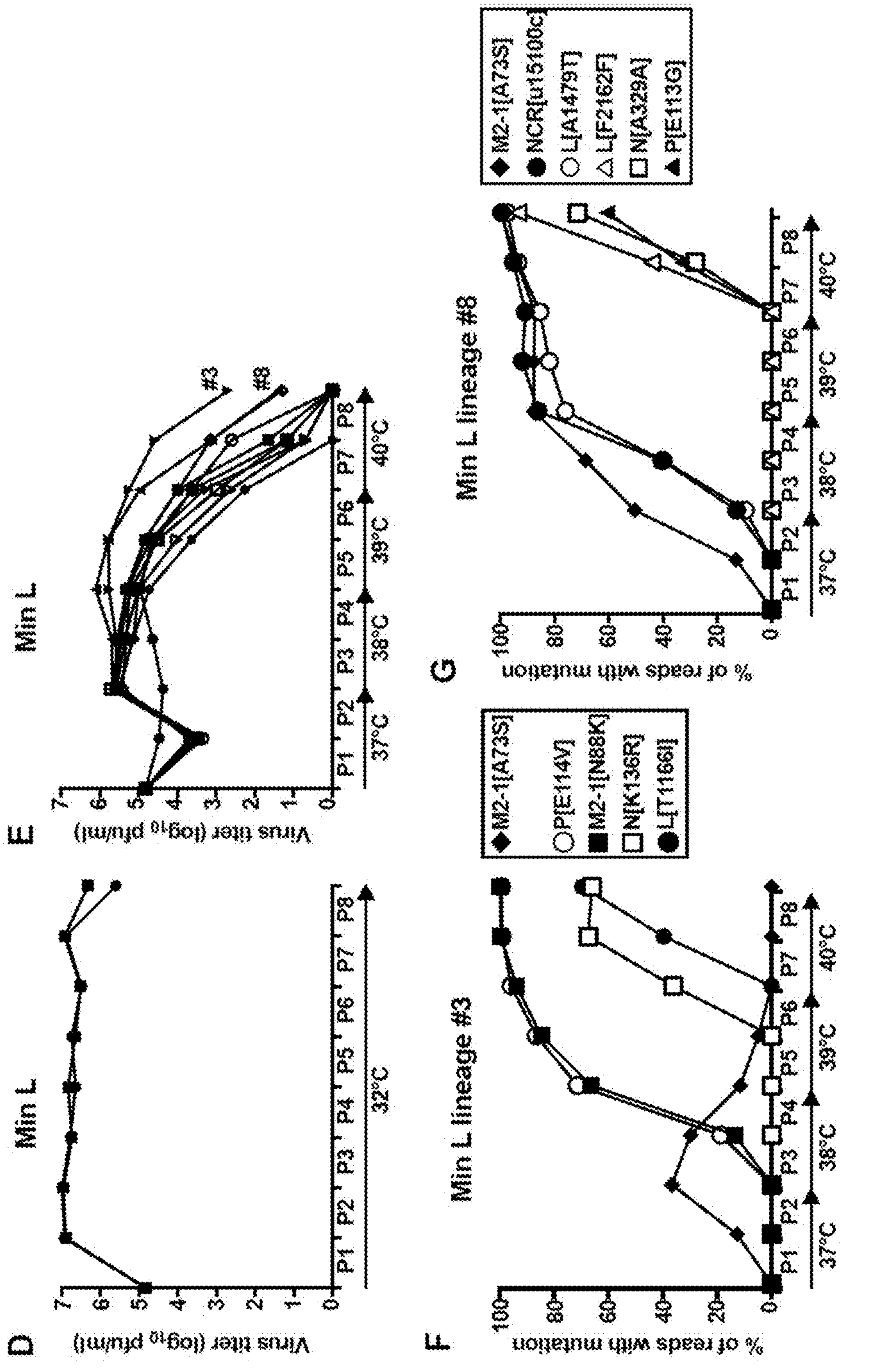

As mentioned above, Min_FLC (for full-length clone) is a mutant in which 9 of the 11 RSV ORFs (excepting only M2-1 and M2-2) were CPD, resulting in a total of 2,692 silent mutations (FIG. 1, panel (A)). Min_FLC is highly temperature-sensitive, with a shut-off temperature ($T_{SH}$) of 35° C. for plaque formation, whereas wild-type (wt) rRSV readily forms plaques at 40° C. $T_{SH}$ is defined as the lowest restrictive temperature at which the difference in titer compared to that at 32° C. is reduced ≥100-fold compared to the difference in titer of wt rRSV at the two temperatures.

To investigate Min_FLC stability, a temperature stress test was employed, representing a surrogate model for genetic stability during virus replication and spread from the cooler upper to the warmer lower respiratory tract. Ten independent 25-$cm^2$ replicate flasks of Vero cells were infected with an initial MOI of 0.1 plaque forming unit (pfu)/cell of Min_FLC and subjected to serial passage at progressively increasing temperatures for a total of 18 passage stages, representing 7 months of continuous culture. (The flasks were incubated at the indicated starting temperatures until extensive cytopathology was observed. Viruses were harvested, and serially passed at increasingly restrictive temperatures (1° C. temperature increase, every other passage).) Two additional replicate flasks were infected and passaged in parallel at the permissive temperature of 32° C. as controls (FIG. 1, panels (B) & (C)). One ml (out of a total of 5 ml) of the supernatant was used to inoculate the next passage. After each passage, aliquots were frozen for titration and sequence analysis by Sanger sequencing and/or deep sequencing as indicated. Virus titers were determined by plaque assay at the permissive temperature (32° C.).

At 32° C., Min_FLC replicated consistently to titers of $10^6$ to $10^7$ pfu/ml (FIG. 1, panel (B)). Deep sequencing of the complete genomes of the two control lineages after 18 passages revealed only low-level, sporadic mutations (FIG. 7), showing that Min_FLC was genetically stable under permissive conditions. In the flasks incubated at increasing temperature, Min_FLC replicated efficiently at 32 and 33° C. ($10^6$ to $10^7$ pfu/ml, FIG. 1, panel (C)). However, after the first passage at 34° C. (P5), virus replication was reduced 200-fold in all 10 lineages, and at the end of the second passage at 35° C. (P8), virus was undetectable in 9 lineages. In the 10th lineage, no virus was detected at the end of the first passage at 37° C. (P11). In contrast, as noted, wt rRSV exhibits no growth restriction at temperatures up to at least 40° C.

Thus, Min_FLC was highly restricted, if not inactive at temperatures above 34-35° C. (the latter being its $T_{SH}$). Consequently, Min_FLC cannot escape its Ts phenotype and is phenotypically stable under stress conditions. Sequencing was not performed on Min_FLC specimens passed under increasingly restrictive temperatures due to the rapid decrease in titers. These results fulfilled the expectation of phenotypic stability for a CPD virus.

Example 3: Temperature Stress on the Min_L Virus Promoted the Emergence of Multiple Mutations in Multiple Genes The Min_L virus in which the L ORF alone (representing 48% of the aggregate RSV ORFs) was CPD, resulting in 1,378 silent mutations (51% as many changes as in Min_FLC). Min_L has a $T_{SH}$ of 37° C. Ten replicate flasks were infected with Min_L and passaged serially at progressively increasing temperatures for a total of 8 passages, corresponding to 2 months of continuous culture, and 2 additional replicate flasks were infected and passaged in parallel at 32° C. as controls (FIG. 1, panels (D) & (E)).

As expected, Min_L replicated efficiently ($10^7$ pfu/ml) at each passage at 32° C. (FIG. 1, panel (D)). Sequence analysis of RNA from the control lineages at P6 by deep sequencing (FIG. 8) and at P8 by Sanger sequencing (data not shown) revealed only sporadic, low-level mutations. In the 10 lineages passaged at increasing temperature, the titers of Min_L in 9 flasks was decreased by about 20-fold at the end of P1 (37° C.) (FIG. 1, panel (E)). However, during the second passage at 37° C., titers in the same 9 lineages increased by about 200-fold, suggesting that selection and outgrowth of temperature-adapted mutants was already occurring. Following P3 (38° C.), virus titers in all 10 lineages decreased steadily: at P8 (second passage at 40° C.), virus was undetectable in 7 lineages, whereas in 2 other lineages, titers were very low (20 pfu/ml each). The remaining lineage (#3, colored in green) had a titer of 500 pfu/ml. Thus, the various Min_L lineages appeared to undergo a partial loss of the temperature-sensitivity phenotype, but ultimately were strongly restricted at 40° C.

For each of the 10 lineages passaged at increasing temperature, whole-genome deep sequencing was performed at the end of P6 (the second passage at 39° C.), when virus replication was still detectable in each lineage. Mutations present in ≥45% of the sequencing reads are shown in Table 1. Remarkably, many of these prominent mutations were in genes not subjected to CPD. Specifically, of these 23 prominent mutations, 21 were distributed among 6 ORFs (P, M, SH, G, M2-1 and L) and 2 were in extragenic regions. Of the 23 mutations, 11 (48%) and 5 (22%) occurred in the M2-1 and L ORFs, respectively. Of the 21 mutations present in ORFs, all but one were missense mutations, suggesting a bias for amino acid change. This positive selection for amino acid change suggests that at least part of the adaptation of Min_L to selective stress involved changes in structure/function in various viral proteins. Some mutations were common to several lineages. Specifically, the mutation [A73S] in the anti-termination transcription factor M2-1 was prominent in 8 out of the 10 lineages. Another M2-1 mutation (N88K) and a mutation in L (A1479T) were prominent in 2 lineages. M2-1 was the only gene to have one or more prominent mutations in every lineage.

Table S1 shows mutations that were present in ≥5% of the reads from the P6 specimens from the same experiment. With this lower cut-off, many more mutations were evident in every gene except NS2. Similar to the prominent mutations that were shown in Table 1, these less prominent mutations were mostly missense mutations. In the CPD L ORF, only 17 out of the total of 31 mutations (55%) involved a nt or a codon that had been modified during CPD (Table S1).

Whole-genome deep sequencing analysis was performed to evaluate the temporal appearance of mutations in the full passage series of lineages #3 and #8, which were of interest because they maintained the highest titers during the stress test (FIG. 1, panel (E)) and thus have the greatest de-attenuation. The appearance and frequency of the more abundant mutations are shown graphically in FIG. 1, panels (F) (lineage #3) and (G) (lineage #8). A more detailed listing of the mutations is shown in Tables S2 and S3.

In both lineages, a single mutation ([A73S] in M2-1) appeared at P1 (13% of each lineage) and then increased at P2 (37 and 51% in lineage #3 and 8, respectively). From P2, the two lineages went into different evolutionary trajectories. In lineage #3, between P2 and P3, while the frequency of M2-1 mutation [A73S] started to decline (30%), 10 other mutations in M2-1 appeared and constituted approximately 15 to 30% of the population (Table S2). One of these M2-1 mutations, namely [N88K], became abundant (71%) in P4, closely concurrent with an equally abundant (66%) mutation [E114V] in P (FIG. 1, panel (F). The other M2-1 mutations declined and were undetectable beyond P5, suggestive of a selective sweep. Two additional prominent mutations were acquired at P6 (N[K136R]) and P7 (L[T1166I]). In lineage #8, mutation [A73S] in M2-1 was fixed at P4 (88%). At P2, two additional mutations (in the 5' trailer region and in L) were acquired and became prominent and fixed by the end of P4. After the first passage at 40° C. (P7), some additional mutations were acquired, three of which became prominent by the end of P8; one silent in L, one silent in N, and one in P[E113G].

Figure 2:
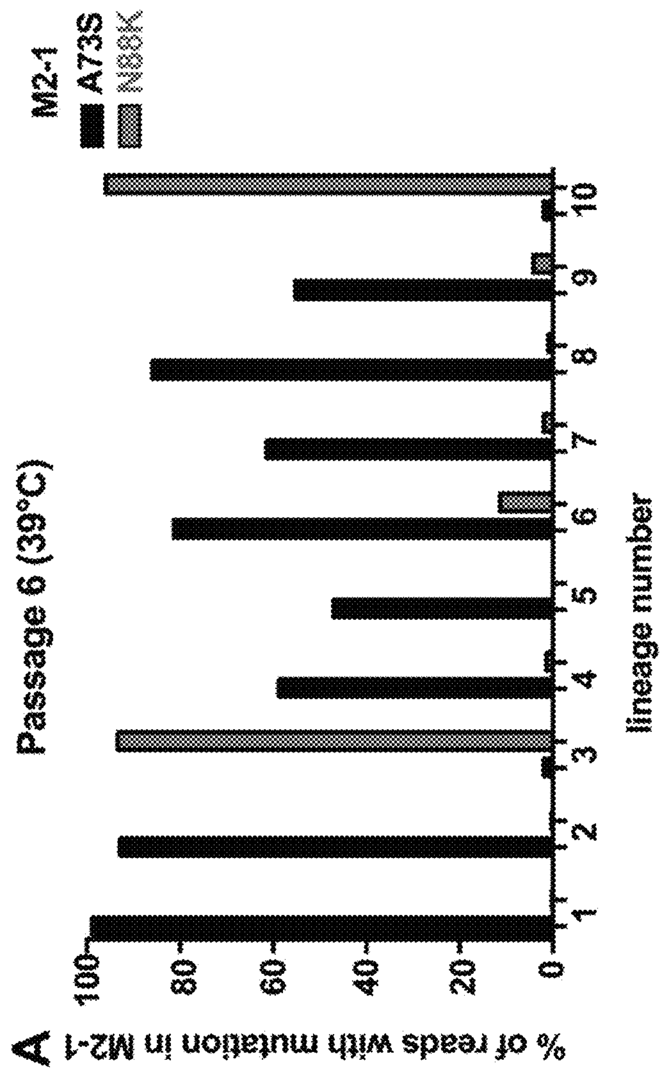
FIG. 2 shows that M2-1 mutations [A73S] and [N88K] segregated into different viral subpopulations. (A) Percentage of deep sequencing reads that contained M2-1 mutation [A73S] or [N88K] at P6 (the second passage at 39° C.) of each of the 10 lineages from the experiment in FIG. 1, panel (E). (B) Lack of linkage between M2-1 mutations [A73S] and [N88K], illustrated by the percentage of deep sequencing reads that contained the indicated combinations of assignments at codons 73 (wt versus [A73S]) and 88 (wt versus [N88K]) in the same read; based on reads from the experiment in FIG. 1, panel (F) that spanned both codons. (C) Extent of linkage between M2-1 mutations [A73S] and [N88K] and other mutations during the first 4 passages of lineage #3 (FIG. 1, panels (E) and (F)), determined by PacBio sequencing of continuous reads corresponding to an 8.2 kb region of the RSV genome from the 3' end to the middle of the M2-2 ORF. Four major virus subpopulations were identified, and mutations that are linked on the same genomes are indicated.
Figure 2:
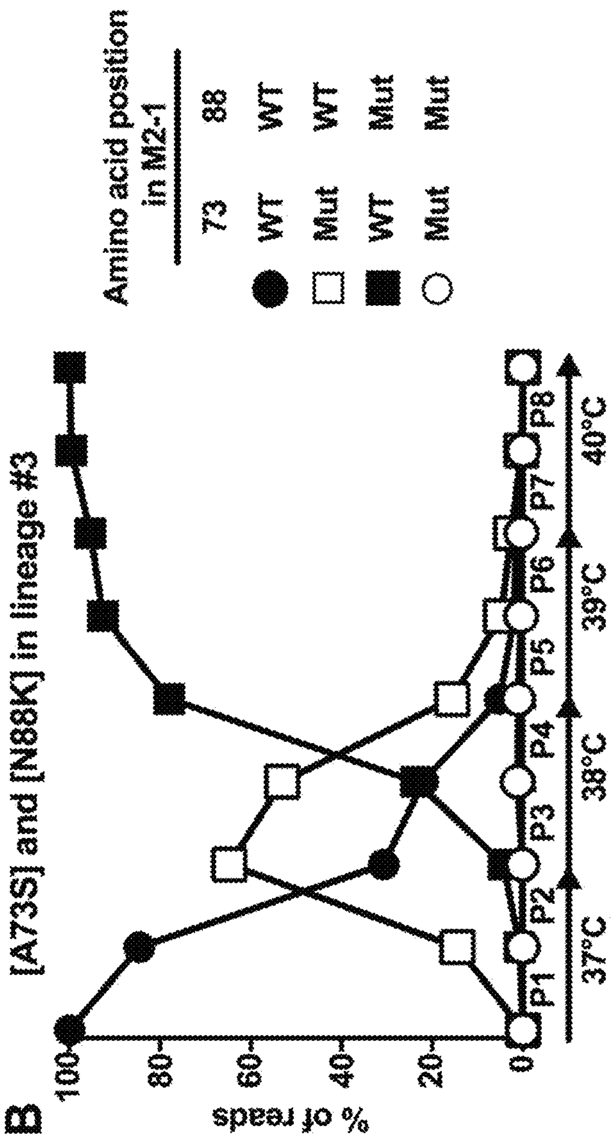
Figure 2:
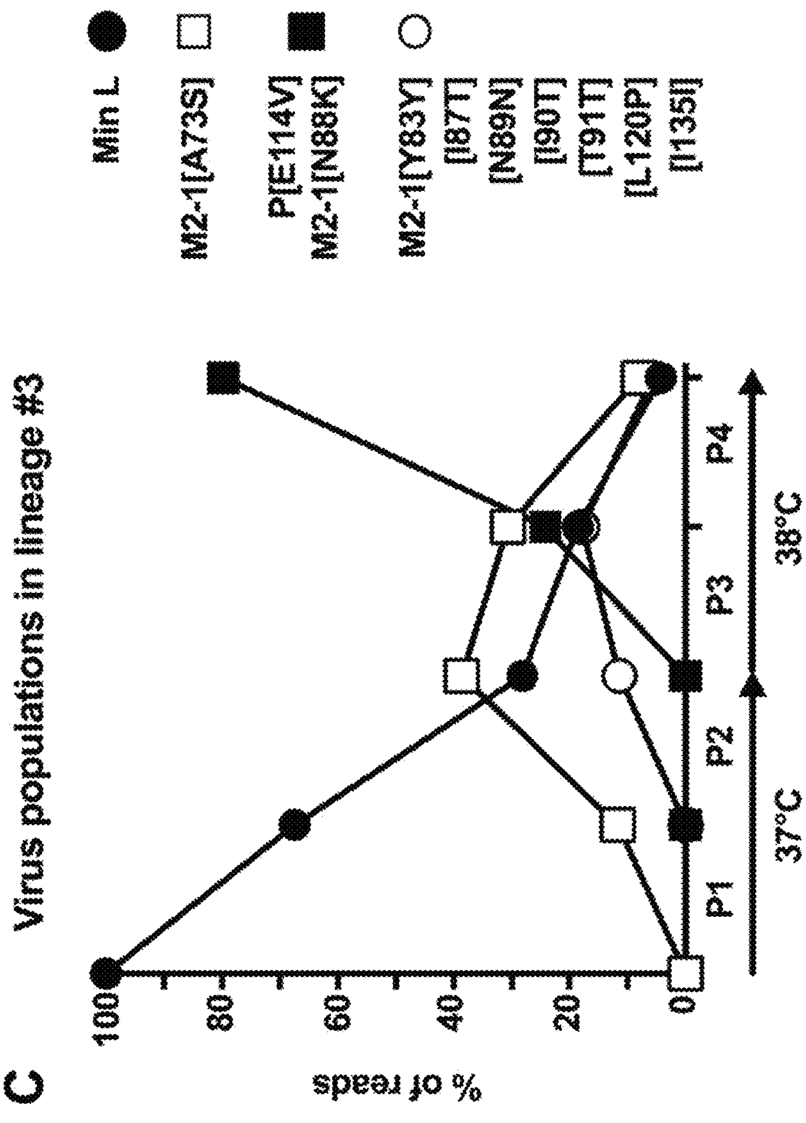

Example 4: The Two Mutations N88K and A73S in the Anti-Termination Transcription Factor M2-1 are Prominent but Incompatible All 10 lineages at P6 had either M2-1 mutation [A73S] or [N88K] (Table 1, FIG. 2, panel (A)). Thus, these 2 M2-1 mutations seemed to segregate. In addition, the disappearance of the [A73S] mutation during passage series of lineage #3 coincided with the appearance and increase of [N88K], until the latter was present in the complete population (FIG. 1, panel (F)). The deep sequencing results of lineage #3 were re-evaluated, scoring only those reads that spanned both position 73 and 88 in M2-1, thus providing a linkage analysis. At P3 and P4, only 1% of the reads had both mutations (FIG. 2, panel (B)), suggesting that these two mutations in M2-1 are incompatible in the same genome and thus constitute 2 separate virus populations.

To further characterize the dynamics of the main virus populations in lineage #3, linkage of the major mutations that appeared during the first 4 passages was investigated using PacBio long read, single molecule sequencing, which provided complete reads of an entire 8.2 kb region from the 3' genome end to the middle of the M2-2 ORF. This showed that the first 4 passages contained four major virus subpopulations (FIG. 2, panel (C)). One was the original Min_L virus, which progressively decreased with passage. Another subpopulation that carried the M2-1 mutation [A73S] alone peaked at P2 and almost disappeared in P4. Another carried 7 mutations in M2-1 (3 synonymous, 4 non-synonymous) that appeared together at P2, reached a maximum at P3 (about 20%) and then disappeared. Finally, the fourth subpopulation contained the P[E114V] and M2-1[N88K] mutations that appeared together at P3 and became prominent at P4.

Example 5: Introduction of the Mutation(s) N[K136R], P[E114V], M2-1[N88K], M2-1[A73S] and L[T1166I] into Min_L Direct identification of mutation(s) responsible for the loss of temperature sensitivity of Min_L was investigated by introducing into Min_L, individually and in combinations, major mutations that had been identified in lineage #3, namely N[K136R], P[E114V], M2-1[N88K], and L[T1166I] (FIG. 1, panel (F)), as well as the M2-1 mutation [A73S] that was one of the prominent mutations in replicate #8 (FIG. 1, panel (G)). The resulting 12 viruses (FIG. 3, panel (A)) were recovered and sequenced completely, confirming the correct sequences and absence of further mutations.

This was performed using the Quickchange Lightning Site-directed Mutagenesis kit (Agilent) following the manufacturer's recommendations. cDNAs were completely sequenced by Sanger sequencing using a set of specific primers. CPD viruses with targeted mutations were then rescued from cDNA as described previously. Briefly, BSR T7/5 cells were transfected using Lipofectamine 2000 (Life technologies) and a plasmid mixture containing 5 μg of full-length cDNA, 2 μg each of pTM1-N and pTM1-P, and 1 μg each of pTM1-M2-1 and pTM1-L. After overnight incubation at 37° C., transfected cells were harvested by scraping into media, added to sub-confluent monolayers of Vero cells, and incubated at 32° C. The rescued viruses were harvested between 11 and 14 days post-transfection.

Figure 3:
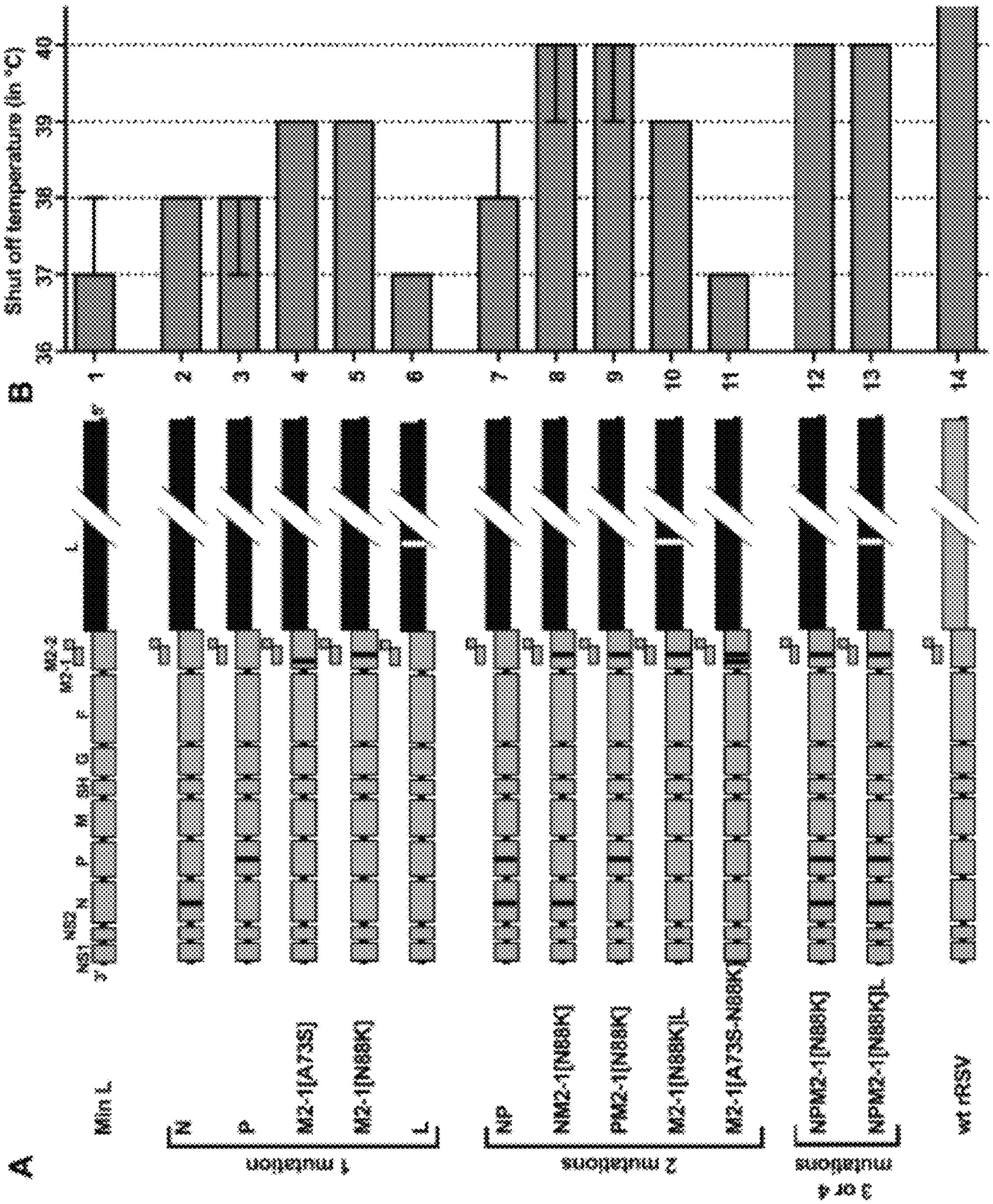
FIG. 3 shows the effects of specific mutations on the temperature sensitivity and in vitro replication of Min_L derivatives. Five major mutations identified in lineage #3 (N[K136R], P[E114V], L[T1166I], M2-1[N88K] and M2-1 [A73S], FIG. 1, panel (F)) were introduced individually and in combinations by site-directed mutagenesis and reverse genetics into Min_L for phenotypic analysis. The Min_L- derived viruses were named based on the gene names bearing the introduced mutations, with the M2-1 mutation specified in brackets. (A) Mutations are indicated in the viral genome map. (B) $T_{SH}$, determined by the efficiency of plaque formation at 32, 35, 36, 37, 38, 39, and 40° C. using published methods. The experiment was done 4 times for viruses #1, 5, 12 and 14, 3 times for viruses #2, 3, 7, 8 and 9, 2 times for viruses #4 and 11 and once for viruses #6, 10 and 13 (bars graphs: medians and range). (C, D) Replication of Min_L-derived mutants in vitro. Vero cells were infected at 32° C. and 37° C. (MOI of 0.01). Titers correspond to the mean of two replicate titrations of two replicates for each time point. The standard deviation is indicated. Due to the large number of viruses, the analysis was divided between experiments #1 (C) and #2 (D).
Figure 3:
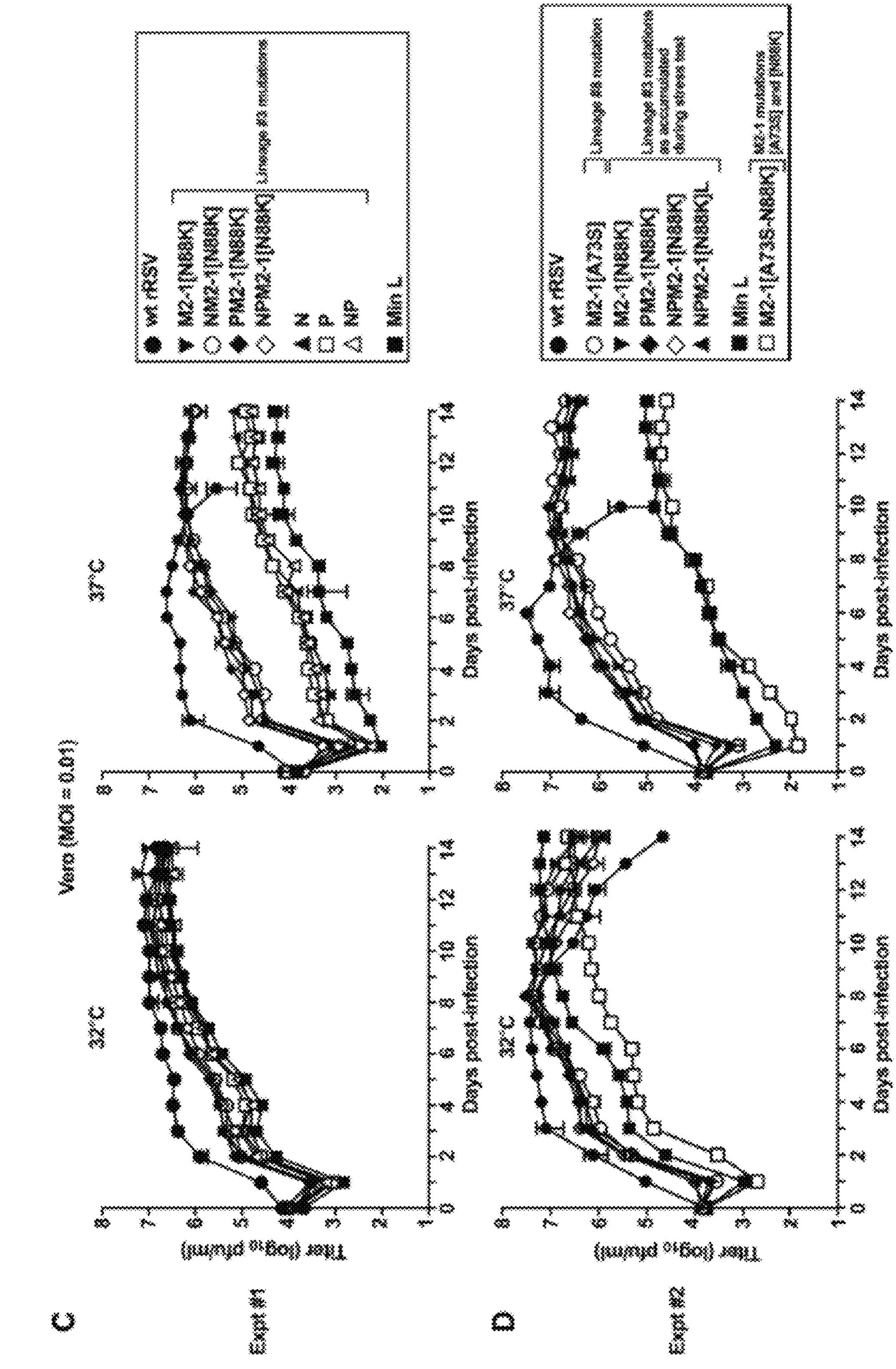

The introduction of the N[K136R] or P[E114V] mutation alone conferred approximately a 1° C. increase in $T_{SH}$ (FIG. 3, panel (B)) compared with Min_L, whereas L[T1166I] alone did not have an effect. Interestingly, the introduction of M2-1[A73S] or [N88K] alone induced a 2° C. increase in $T_{SH}$, suggesting that either of these two M2-1 mutations alone played the greatest role in the de-attenuation of Min_L. The combination of the N or P mutation with M2-1[N88K] conferred a further, small increase in $T_{SH}$ (average of 2.5° C. from three independent experiments). The combination of the N, P, and M2-1[N88K] mutations induced a 3° C. increase in $T_{SH}$ (40° C.) compared to Min_L, which was not further increased by the addition of the L mutation. This illustrated the additive role of the N, P, and M2-1[N88K] mutations in the increase in the $T_{SH}$ of lineage #3. The combination of M2-1[A73S] and [N88K] did not confer any increase in the $T_{SH}$ of Min_L, illustrating their incompatibility, as predicted based on the deep sequencing results.

The effects of these mutations on the kinetics and efficiency of Min_L replication in Vero cells was also studied (FIG. 3, panels (C) & (D)). The effects of the mutations were more evident at 37° C. (FIG. 3, panels (C), (D), right panels) than at 32° C. (left panels), as would be expected for temperature-sensitivity mutations. The N and P mutations alone and in combination had only a small effect on increasing viral replication compared to Min_L. In contrast, the introduction of either the M2-1[N88K] or the [A73S] mutation alone resulted in a substantial increase in replication, and this was not much affected by the further addition of the N, P, and L mutations. In addition, virus bearing both of the incompatible M2-1[A73S] and [N88K] mutations replicated similar to or less efficiently than Min_L at 37° C. and 32° C., respectively (FIG. 3, panel (D), left and right panels). Thus, the M2-1[N88K] or [A73S] mutations played the major role in restoring the ability of Min_L to replicate in Vero cells, but they were incompatible.

Further, the effects of the introduced mutations on the kinetics of viral gene transcription, viral genomic RNA synthesis, protein expression, and virus particle production in a single infection cycle (FIG. 4, panels (A) to (E)) was investigated. Vero cells were infected at an MOI of 3 pfu/cell with the indicated viruses, and samples were collected for analysis every 4 h for 24 h.

Analysis of the accumulation of the 9 smaller RSV mRNAs (i.e., all except L) was performed by positive-sense-specific RT-qPCR assays specific for each mRNA. Data for the P mRNA, which are generally representative, are shown in FIG. 4, panel (A), and the complete data set for these 9 mRNAs is shown in FIG. 9. In general, transcription was greatly reduced at 37° C. for Min_L compared to wt rRSV. The introduction of either M2-1 mutation into Min_L resulted in a substantial restoration of transcription. The further addition of the N, P, and L mutations to M2-1[N88K] provided a further modest, but mostly consistent, increase. Western blot analysis showed that, as expected, the viral protein accumulation occurred later than that of the mRNAs but otherwise the pattern was similar to the mRNA accumulation (FIG. 4, panel (B) and FIG. 10).

The accumulation of the RSV L mRNA by positive-sense-specific, L-specific RT-qPCR (FIG. 4, panel (C)) was examined. At 32° C., a basal level of L mRNA was detected in Min_L-infected cells, but there was essentially no increase with time, in contrast to the progressive increase with time observed with wt L mRNA. The extensive sequence differences in the wt and CPD L genes necessitated the use of different primer pairs for wt rRSV versus Min_L derivatives, precluding direct comparison of relative abundances at the different time points. At 37° C., CPD L mRNA was undetectable, indicating a strong restriction at this temperature. The addition of the M2-1[N88K] or [A73S] mutation to Min_L partly restored CPD L gene transcription at both 32 and 37° C. The additional inclusion of the N, P, and L mutations further increased L gene expression.

The production of cell-associated genomic RNA (FIG. 4, panel (D)) by Min_L was almost undetectable at either 32 or 37° C. but was detected at 24 hpi at both 32 and 37° C. by M2-1[A73S] and M2-1[N88K], and in further increased amounts in NPM2-1[N88K]L infected cells. Genomic RNA production by wt rRSV was detectable starting at 12 hpi at both 32 and 37° C. and was higher compared to NPM2-1[N88K]L.

The production of infectious virus particles was concurrent with the accumulation of genomic RNA (FIG. 4, panel (E)). At 32° C., Min_L virus titers started to increase only at 24 hpi, while no increase was detected at 37° C. M2-1[A73S] and M2-1[N88K] virus particles started to accumulate earlier (20 hpi at both temperatures) and at higher levels (6- and 110-fold higher at 32 and 37° C., respectively) than Min_L particles. NPM2-1[N88K]L virus production was first detected at 16 hpi at both temperatures and also at greater amounts (9 and 300-fold higher at 32 and 37° C., respectively) than Min_L virus production. Infectious wt rRSV was first observed at 12 hpi at both temperatures (FIG. 4, panel (E)), at higher level than NPM2-1[N88K]L (10-fold higher at both 32 and 37° C.).

The plaque sizes produced in Vero cells were measured, as an additional parameter for virus fitness (FIG. 4, panels (F) & (G)). Wt rRSV produced plaques of significantly larger size than Min_L ($p \leq 0.05$). Addition of the M2-1[A73S] or [N88K] mutations to Min_L increased virus fitness, resulting in plaque sizes that were not significantly different from those of wt rRSV ($p > 0.05$ compared with wt rRSV). Plaques induced by M2-1[A73S][N88K] were smaller than Min_L plaques, further confirming that these two M2-1 mutations are incompatible.

Thus, the two most prominent mutations acquired under stress were two missense mutations ([A73S] and [N88K]) in the M2-1 ORF, encoding the RSV transcription anti-termination factor. Reintroduction of either of these mutations by reverse genetics rescued a substantial part of the replicative fitness of Min_L at 37° C., increasing viral gene transcription, protein expression, particle production, and plaque size. These two M2-1 mutations partly restored the transcription of the CPD L gene at 37° C., which otherwise was below the level of detection at this temperature. The partial restoration of L gene expression would be expected to increase the production of the polymerase, although that was not directly monitored here due to its low abundance and a lack of available antibody. We presume that an increase in the production of L protein would then increase transcription of all of the RSV genes, indirectly increase the synthesis of viral proteins, increase RNA replication, and ultimately indirectly increase the production of progeny virus. These effects on the accumulation of viral mRNAs, proteins, genomic RNA, and progeny virions indeed were observed. Thus, the acquisition of either of two mutations in M2-1 adapted Min_L at 37° C., by increasing transcription of the CPD L gene.

The mechanism(s) behind the rescued CPD L gene expression by the two M2-1 mutations remains unknown. The RSV M2-1 protein is necessary for the efficient synthesis of full-length mRNAs, which otherwise terminate prematurely. The M2-1 protein also increases the synthesis of polycistronic read-through mRNAs. It likely binds nascent mRNA co-transcriptionally and prevents termination by the viral polymerase. In addition, the M2-1 protein binds directly to P. The binding of P and RNA to M2-1 was found to be mutually exclusive due to partially overlapping interaction surfaces. Although A73 and N88 are away from the RNA/P binding interface, they could possibly be on the path of the exiting nascent RNA molecule. A simple model would be that the 1,378 nt changes that were introduced during CPD affected the L gene template so as to reduce the efficiency of transcription elongation of the nascent L mRNA. L transcription was partly restored by the M2-1 mutations through some effect on the polymerase complex. The prominent mutations that were acquired under stress were most frequent in the M2-1 ORF, but also were found in P, N, and L ORFs, all of which encode viral proteins involved in RNA synthesis. These additional N, P and L mutations further increased the efficiency of CPD L gene transcription possibly by also increasing the efficiency of transcription elongation on the CPD L gene.

Example 6: Computer-Based Molecular Dynamics Simulations (MDS)

Computer-based molecular dynamics simulations (MDS) was used to investigate possible effects of the M2-1 [A73S]

and [N88K] mutations on M2-1 structure (FIG. 6). The M2-1 tetramer is shown in FIG. 6, panel (A) with specific views in panels (B), (C), and (D). In the wt M2-1 tetramer, a salt bridge is predicted to exist between K19 of one monomer and D116 of the adjoining monomer. These amino acids are shown for the red and cyan monomers (FIG. 6, panel (B)). MDS suggests that the salt bridge helps stabilize the interaction between adjacent monomers. The A73 residue of a third monomer is predicted to be in close proximity but not involved in interactions. When A73 is changed to serine ([A73S], FIG. 6, panel (C)), the salt bridge between K19 and D116 is predicted to be maintained. In addition, unlike the alanine, a serine at codon 73 is predicted to form a hydrogen bond with K19 and in some MDS time frames a hydrogen bond with D116 (not shown). Thus, S73 could provide new stabilizing links between each adjoining monomers. The predicted effect of the N88K mutation is to increase stability within rather than between monomers. Specifically, in the wt M2-1 tetramer structure, N88 is predicted to form a hydrogen bond with S82 (FIG. 6, panel (B)). In contrast, a lysine residue at codon 88 is predicted to form an intra-monomer salt-bridge with E70 (FIG. 6, panel (D)). The K88 would no longer interact with S82. In addition, the hydrophobic carbon chain of K88 is predicted to form a number of intra-monomer van der Waals interactions with L74. Thus, the prominent M2-1 mutations acquired during the stress test are predicted to create new interactions between (A73S) and within (N88K) M2-1 monomers. This increased stability presumably could contribute to rescue transcription of the CPD L gene. Interestingly, this increased stability is not expected to be maintained when both mutations are present together. Indeed, these two mutations could possibly form an H-bonded pair between the side chains of the S73 and K88 which would result in less flexibility of the loop on which K88 resides. This reduced flexibility could explain the incompatibility of these 2 mutations.

Interestingly, mutations that were found in P ([E113G] and [E114V]) are localized in the interaction domain of P with M2-1. Mutations at these 2 positions were shown to increase the affinity of P for M2-1. This work further supports the theory that the compensatory mutations act by increasing the stability of the ribonucleoprotein complex, which we hypothesize may facilitate transcription of the CPD L gene.

As mentioned, a single mutation in the M2-1 gene (A73S) that appeared in the first passage of Min_L at 37° C. and was found in 8 of 10 cultures was sufficient to rescue Min_L replication at that temperature. In addition, this single mutation conferred increased replication to Min_L in hamsters. We had anticipated that de-attenuation of a CPD ORF would involve multiple changes in the CPD sequence conferring incremental de-attenuation. However, this study shows that a single mutation in a different gene was sufficient to yield substantial de-attenuation. Therefore deoptimization involving large numbers of nt changes does not necessarily provide a stable attenuation phenotype.

Example 7: Introduction of De-Attenuating Mutations from Min_L into Min_FLC

The major mutations that were introduced into Min_L, namely N[K136R], P[E114V], M2-1[N88K], M2-1[A73S], and L[T1166I], were introduced in various combinations into Min_FLC and assessed for virus titer following recovery (FIG. 11, panel (A)) and $T_{SH}$ (FIG. 11, panel (B)). The M2-1[N88K] and [A73S] mutations individually did not increase the fitness of Min_FLC as measured by viral titer or $T_{SH}$. The combination of the N, P, and M2-1[N88K] mutations conferred a 2° C. increase in $T_{SH}$, but this virus only grew to a low titer.

Surprisingly, the introduction of the L[T1166I] mutation into Min_FLC alone or in combinations with one or more of the other mutations appeared to inhibit recovery. Thus, none of these mutations improved the overall fitness of Min_FLC, even though it bears the same CPD L gene as Min_L. This result suggests that multiple CPD ORFs augment phenotypic stability under selective pressure.

Example 8: Evaluation of Min_L Derivatives in Mice and Hamsters

The replication of the Min_L derivatives was evaluated in vivo (FIG. 5). BALB/c mice were infected intranasally (IN) with $10^6$ pfu of each virus. Nasal turbinates (NT) and lungs were harvested on days 4 (n=8 per virus), 5 (n=8), and 10 (n=4) post-infection (pi). At the peak of virus replication (day 5 pi; FIG. 5, panel (B)), virus was detected in the NT of only 2 mice infected with Min_L, and 3 mice infected with M2-1[N88K]. Replication of M2-1[A73S] was detected in 4 of 8 mice, which was comparable to wt rRSV. NPM2-1[N88K]L replication was not detected in the NT of any of the mice. In the lungs on day 5, replication of M2-1[N88K] and M2-1[A73S] was slightly reduced compared with Min_L, but was not statistically different, and replication of NPM2-1[N88K]L was strongly reduced in the lungs compared to Min_L. The day 10 titers are not shown because virus was recovered only from 2 animals, in the M2-1[A73S] group at trace levels.

The same set of viruses was compared in hamsters (FIG. 5, panel (C)). On day 3, NT and lungs were harvested from 9 hamsters per virus. In the NT, Min_L replication was reduced approximately 100-fold compared to wt rRSV ($p \leq 0.01$). Replication of M2-1[N88K] was modestly increased compared to Min_L, but remained significantly attenuated compared to wt rRSV. In contrast, the titers of M2-1[A73S] were further increased compared to Min_L, and were not statistically different from wt rRSV. Interestingly, replication of NPM2-1[N88K]L in the NTs was reduced compared to Min_L. In the lungs, Min_L and M2-1[N88K] were detected in only 1 out of 9 hamsters for each virus, and replication of NPM2-1[N88K]L was undetectable. In contrast, replication of M2-1[A73S] was increased compared to Min_L, as 5 out of 9 hamsters exhibited virus replication to about $10^2$ pfu/g. Thus, in hamsters, the mutation M2-1[A73S] increased the replication of Min_L, a marker of de-attenuation, while the M2-1 [N88K] mutation did not affect the replication of Min_L, and the combination of the N, P, L, and M2-1[N88K] mutations decreased replication.

Despite a significant restriction of replication, Min_L and the Min_L-derived viruses induced titers of antibodies that were not statistically different from those induced by wt rRSV (FIG. 5, panel (D)). The M2-1[A73S] virus induced significantly higher levels of RSV-neutralizing serum antibodies than Min_L and M21-1[N88K]. Interestingly, the NPM2-1[N88K]L virus also was comparable to wt rRSV in inducing RSV-neutralizing antibodies despite its highly restricted replication. On day 31, hamsters were challenged IN with wt rRSV, and NT and lungs were harvested 3 days post-challenge. No detectable challenge virus replication was detected except for a trace of virus in one animal in the Min_L group (not shown).

Example 9: Genetic Stability of the Min_L-NPM2-1[N88K]L Virus

The observation that the NPM2-1[N88K]L virus was more highly attenuated than Min_L and yet was as immunogenic as wt rRSV identified this virus as a promising vaccine candidate. Therefore, its stability was evaluated in a temperature stress test involving 4 passages at 39° C. and 4 passages at 40° C., corresponding to 2 months of continuous passage (FIG. 12). Sanger sequencing of the complete genome of the final passage of the 10 different stressed lineages and the 2 control flasks did not detect any abundant mutations (not shown). This showed that introduction of the N, P, M2-1[N88K], and L mutations into Min_L to create the promising NPM2-1[N88K]L virus conferred genetic stability. The nucleotide sequence of Min_L-NPM2-1[N88K]L is shown in FIG. 14 and represented by SEQ ID NO: 14.

TABLE 1

Mutations detected in individual lineages of Min_L at the end of P6 (second passage at 39° C.) of the temperature stress test, present at ≥45% frequency[a].

| | | | Percentage of reads with mutation in indicated lineage number[a] | | | | | | | | | |
|---|---|---|---|---|---|---|---|---|---|---|---|---|
| Gene | Nt mutation | Aa mutation | 1 | 2 | 3 | 4 | 5 | 6 | 7 | 8 | 9 | 10 |
| Intergenic NS2-N | g1123a | — | | | | | | | 85 | | | |
| P | a2687u | E114V | | | 96 | | | | | | | |
| M | u3798a | N179K | | 61 | | | | | | | | |
| SH | c4369a | H22Q | | | | | | | | | 81 | |
| SH | c4387g | I28M | | | | | | | | | 71 | |
| G | a5384g | E232 (silent) | | | | | | 47 | | | | |
| M2-1 | g7823u | A73S | 99 | 93 | | 61 | 48 | 83 | 63 | 87 | 57 | |
| M2-1 | c7870a | N88K | | | 94 | | | | | | | 96 |
| M2-1 | a8013g | E136G | | | | | | 48 | | | | |
| L | u10548c[b] | Y684H[b] | 97 | | | | | | | | | |
| L | u10797c[b,c] | S767P[b,c] | | | | | | | | | | 82 |
| L | g12933a | A1479T | | 63 | | | | | | 85 | | |
| L | a13783c[b] | Y1762S[b] | | | | | | 83 | | | | |
| 5' extragenic (trailer) | u15100c | — | | | | | | | | 75 | | |

[a]Percentage of reads with the indicated mutation; only mutations present in ≥45% of the reads are shown. Nucleotide numbering is based on RSV sequence M74568 (biological wt RSV strain A2). Mutations present in ≥5% of reads from this same experiment are shown in Table S1.
[b]Mutation involving a codon that had been changed as part of CPD of the L ORF.
[c]Mutation involving a nucleotide position that had been changed as part of CPD of the L ORF.

TABLE S1

Mutations detected (at a frequency of ≥5%) in each of the 10 lineages of Min_L at the end of P6 (second passage at 39° C.) of the temperature stress test[a].

| | | | Lineage number and the percentage of reads with the indicated mutation[a] | | | | | | | | | |
|---|---|---|---|---|---|---|---|---|---|---|---|---|
| Gene | Nt mutation | Aa mutation | 1 | 2 | 3 | 4 | 5 | 6 | 7 | 8 | 9 | 10 |
| NS1 | g101a | M1I | | | | 26 | | | | | | |
| NS1 | c439a | S114Y | | | 6 | 10 | | 9 | | | 12 | |
| NS1 | a441c | K115Q | | | | 25 | | 19 | | | 32 | |
| Intergenic NS2-N | g1104a | — | | | | | | 7 | | | | |
| Intergenic NS2-N | g1120a | — | 10 | | | | | | | | | |
| Intergenic NS2-N | g1123a | — | 11 | | | | | | 85 | | | |
| N | a1547g | K136R | | | 32 | | | | 8 | | | |
| N | c1737u | G199 (silent) | | | | | | | | | | |
| N | a2293g | K385E | | | | | 7 | | | | | |
| N | a2295g | K385 (silent) | | | 19 | | | | | | | |
| P | a2386g | N14D | | | | | | | 12 | | | |
| P | u2434c | S30P | 12 | | | | | | | | | |
| P | g2683a | E113K | | | | | | | | | 13 | |
| P | a2687u/g | E114V | | | 96 | 34 | | | | | | |
| P | a2695c | S117R | | | | | 20 | | | | | |
| P | g2926a | A194T | | | | | | | | | 16 | |
| Intergenic P-M | g3167a | — | | | | | 10 | 18 | | | | |
| Intergenic P-M | g3191c | — | 23 | | | | | | | | 17 | 16 |
| M | a3428g | N56S | | | | | | 6 | | | | |
| M | u3798a | N179K | | 61 | | | | | | | | |
| M | a3821u | N187I | | | | 11 | | 10 | 15 | | | |
| SH | c4369a | H22Q | | 9 | 11 | 36 | 10 | 26 | | | 81 | 12 |
| SH | c4387g | I28M | | | | | | | | | 71 | |
| G | a5384g | E232 (silent) | | | | | | 47 | | | | |
| G | g5499a | E271K | | | | | | | | | 18 | |
| Intergenic G-F | u5646a | / | | | | | | | | | | 11 |
| F | u5755a | F32I | | | 26 | | | | | | | |
| F | g6115a | V152I | | | | | | | 5 | | | |
| F | g6382u | A241S | | | | | | | | | 30 | |

TABLE S1-continued

Mutations detected (at a frequency of ≥5%) in each of the 10 lineages of Min_L at the end of P6 (second passage at 39° C.) of the temperature stress test[a].

| | | | Lineage number and the percentage of reads with the indicated mutation[a] | | | | | | | | | |
|---|---|---|---|---|---|---|---|---|---|---|---|---|
| Gene | Nt mutation | Aa mutation | 1 | 2 | 3 | 4 | 5 | 6 | 7 | 8 | 9 | 10 |
| F | g6425a | S255N | | | | | | | | | | 6 |
| F | u7298c | L546P | | | | | | | | 7 | | |
| F | g7330u | V557F | | | | | | | | 7 | | |
| F | a7381u | N574Y | | | 10 | | | | | | | |
| Intergenic F-M2 | c7552a | — | | | | | | 5 | | | | |
| M2-1 | c7807g | D67E | | | | | | | 14 | | | |
| M2-1 | g7823u | A73S | 99 | 93 | | 61 | 48 | 83 | 63 | 87 | 57 | |
| M2-1 | u7852c | S82 (silent) | | | | | | | | | 16 | |
| M2-1 | u7855c | Y83 (silent) | | | | 11 | 5 | | | | | |
| M2-1 | u7857c | I84T | | | | 11 | | | 12 | | 14 | |
| M2-1 | u7866c | I87T | | | | 23 | 8 | | 15 | | 23 | |
| M2-1 | u7866a | I87K | | | | | | | | 11 | | |
| M2-1 | c7870a | N88K | | | 94 | | | 13 | | | | 96 |
| M2-1 | a7872c | N89T | | | | | 30 | | | | | |
| M2-1 | u7873c | N89 (silent) | | | | 18 | | | | | | |
| M2-1 | a8013g | E136G | | 21 | | | 39 | 48 | 19 | | | |
| M2-2 | u8255c | N32 (silent) | | | 11 | | | | | | | |
| M2-2 | c8268u | L37 (silent) | | | | | | | 5 | | | |
| M2-2 | c8428a | S90Stop | | | | 5 | | | | | | |
| L gene start | a8494g | — | | | | | | | | 6 | | |
| L | a8514g | N6D | 11 | | | | | | | | | |
| L | u8563a[b] | V22E[b] | | | | | | 8 | 6 | | | |
| L | u8950c[b] | V151A[b] | | | | | | 32 | | | | |
| L | g8985a[b] | A163T[b] | | | | | | | 12 | | | |
| L | a9560g | K354 (silent) | | | | | | | | | 15 | |
| L | c10029u[b,c] | R511C[b,c] | | | | | | | | | | 14 |
| L | c10298g[b,c] | C600W[b,c] | | 6 | | | | | | | | |
| L | a10301g | V601 (silent) | | 7 | | | 8 | | | | | |
| L | a10527u | I677L | | | | | | | 6 | | | |
| L | u10548c[b] | Y684H[b] | 97 | | | | | | | | | |
| L | u10797c[b,c] | S767P[b,c] | | | | | | | | | | 82 |
| L | a10972u[b] | E825V[b] | | 5 | | | | | | | | |
| L | u11278a[b] | I927N[b] | | 7 | | | | | | | | 8 |
| L | g11535a[b] | V1013I[b] | | | | | | | | 6 | | |
| L | a11575g | D1026G | | | | 21 | | | | | | |
| L | u11775g | F1093V | | 6 | | | | | | | | |
| L | a11783g | K1095 (silent) | | 8 | | | | 7 | | | | 6 |
| L | c11790u | Q1098Stop | | 6 | | | | | | | | |
| L | u11795c | H1099 (silent) | | 5 | | | | | | | | |
| L | a11956g[b] | K1153R[b] | 20 | | | | | | | | | |
| L | a12078g | M1194V | | | | | | 17 | | | | 12 |
| L | g12114a | V1206I | | | | | 11 | | | | | |
| L | a12210c[b,c] | S1238R[b,c] | | | | | | | | | 8 | |
| L | u12386a | D1296E | | | 7 | | | | | | | |
| L | g12933a | A1479T | | 63 | | 7 | | 8 | | 85 | 11 | |
| L | a13783c[b] | Y1762S[b] | | | | | | 83 | | | | |
| L | u14045c[b,c] | I1849[b,c] (silent) | | | | | | | | | | 25 |
| L | c14204g[b,c] | Y1902Stop[b,c] | | | | | | 6 | | | | |
| L | c14411u[b,c] | I1971[b,c] (silent) | | | | | | | | 18 | | |
| L | c14805u | H2103Y | | | | 36 | | | | | | |
| L | c14834u[b,c,d] | H2112[b,c,d] (silent) | | | | | | | 6 | | | |
| 5' extragenic | u15100c | / | | | | | | | | 75 | | |
| 5' extragenic | a15143g | / | | | | | | | 20 | | | |

[a]Percentage of reads with the indicated mutation; only mutations present in ≥5% of the reads are shown. Mutations detected in ≥50% of the reads are highlighted in yellow and mutations detected in 25 to 49% of reads are highlighted in green. Nucleotide numbering is based on RSV sequence M74568.

[b]Mutations involving a codon that had been changed as part of CPD of L.

[c]Mutations involving a nucleotide that had been changed as part of CPD of L.

[d]Mutation involving a nucleotide that had been changed as part of CPD of L and that restored wt sequence.

TABLE S1-A

Mutations detected (at a frequency of ≥25%) in each of the 10 lineages of Min_L at the end of P6 (second passage at 39° C.) of the temperature stress testa.

| | | | Lineage number and the percentage of reads with the indicated mutationa | | | | | | | | | |
|---|---|---|---|---|---|---|---|---|---|---|---|---|
| Gene | Nt mutation | Aa mutation | 1 | 2 | 3 | 4 | 5 | 6 | 7 | 8 | 9 | 10 |
| NS1 | g101a | M1I | | | | 26 | | | | | | |
| NS1 | a441c | K115Q | | | | 25 | | 19 | | | 32 | |
| Intergenic NS2-N | g1123a | — | 11 | | | | | | 85 | | | |
| N | a1547g | K136R | | | 32 | | | | | | | |
| P | a2687u/g | E114V | | | 96 | 34 | | | | | | |
| M | u3798a | N179K | | 61 | | | | | | | | |
| SH | c4369a | H22Q | | 9 | 11 | 36 | 10 | 26 | | | 81 | 12 |
| SH | c4387g | I28M | | | | | | | | | 71 | |
| G | a5384g | E232 (silent) | | | | | | 47 | | | | |
| F | u5755a | F32I | | | 26 | | | | | | | |
| F | g6382u | A241S | | | | | | | | | 30 | |
| M2-1 | g7823u | A73S | 99 | 93 | | 61 | 48 | 83 | 63 | 87 | 57 | |
| M2-1 | c7870a | N88K | | | 94 | | | 13 | | | | 96 |
| M2-1 | a7872c | N89T | | | | | 30 | | | | | |
| M2-1 | a8013g | E136G | | 21 | | | 39 | 48 | 19 | | | |
| L | u8950c[b] | V151A[b] | | | | | | 32 | | | | |
| L | u10548c[b] | Y684H[b] | 97 | | | | | | | | | |
| L | u10797c[b,c] | S767P[b,c] | | | | | | | | | | 82 |
| L | g12933a | A1479T | | 63 | | 7 | | 8 | | 85 | 11 | |
| L | a13783c[b] | Y1762S[b] | | | | | | 83 | | | | |
| L | u14045c[b,c] | I1849[b,c] (silent) | | | | | | | | | | 25 |
| L | c14805u | H2103Y | | | | 36 | | | | | | |
| 5' extragenic | u15100c | / | | | | | | | | 75 | | |

[a]Percentage of reads with the indicated mutation; only mutations present in ≥25% of the reads are shown. Nucleotide numbering is based on RSV sequence M74568.
[b]Mutations involving a codon that had been changed as part of CPD of L.
[c]Mutations involving a nucleotide that had been changed as part of CPD of L.

TABLE S1-B

Mutations detected (at a frequency of ≥50%) in each of the 10 lineages of Min_L at the end of P6 (second passage at 39° C.) of the temperature stress test[a].

| | | | Lineage number and the percentage of reads with the indicated mutation[a] | | | | | | | | | |
|---|---|---|---|---|---|---|---|---|---|---|---|---|
| Gene | Nt mutation | Aa mutation | 1 | 2 | 3 | 4 | 5 | 6 | 7 | 8 | 9 | 10 |
| Intergenic NS2-N | g1123a | — | 11 | | | | | | 85 | | | |
| P | a2687u/g | E114V | | | 96 | 34 | | | | | | |
| M | u3798a | N179K | | 61 | | | | | | | | |
| SH | c4369a | H22Q | | 9 | 11 | 36 | 10 | 26 | | | 81 | 12 |
| SH | c4387g | I28M | | | | | | | | | 71 | |
| M2-1 | g7823u | A73S | 99 | 93 | | 61 | 48 | 83 | 63 | 87 | 57 | |
| M2-1 | c7870a | N88K | | | 94 | | | 13 | | | | 96 |
| L | u10548c[b] | Y684H[b] | 97 | | | | | | | | | |
| L | u10797c[b,c] | S767P[b,c] | | | | | | | | | | 82 |
| L | g12933a | A1479T | | 63 | | 7 | | 8 | | 85 | 11 | |
| L | a13783c[b] | Y1762S[b] | | | | | | 83 | | | | |
| 5' extragenic | u15100c | / | | | | | | | | 75 | | |

[a]Percentage of reads with the indicated mutation; only mutations present in ≥50% of the reads are shown. Nucleotide numbering is based on RSV sequence M74568.

[b]Mutations involving a codon that had been changed as part of CPD of L.

[c]Mutations involving a nucleotide that had been changed as part of CPD of L.

TABLE S2

Accumulation of mutations in passages 1 to 8 (from 37 to 40° C.) in lineage #3 during the temperature stress test[a].

| Gene | Nt mutation | Aa mutation | P1 (37) | P2 (37) | P3 (38) | P4 (38) | P5 (39) | P6 (39) | P7 (40) | P8 (40) |
|---|---|---|---|---|---|---|---|---|---|---|
| | | | Passage (P) number (temperature) and the percentage of reads with the indicated mutation | | | | | | | |
| NS1 gene start | g45a | / | | | | | | | 22 | 17 |
| NS1 | u308c | N70 (silent) | | | | | | | 14 | 25 |
| NS1 | c439a | S114Y | | | 5 | 5 | 4 | 6 | | |
| N | a1547g | K136R | | | | | | 33 | 67 | 66 |
| P | a2687u | E114V | | | 19 | 71 | 87 | 96 | 99 | 100 |
| M | a3281g | K7R | | | | | | | 9 | 15 |
| M2-1 | c7807g | D67E | | 8 | 5 | | | | | |
| M2-1 | g7823u | A73S | 13 | 37 | 30 | 12 | 5 | | | |
| M2-1 | u7833c | V76A | | 7 | 5 | | | | | |
| M2-1 | u7855c | Y83 (silent) | | 19 | 26 | 12 | 6 | | | |
| M2-1 | u7866c | I87T | | 21 | 29 | 14 | 7 | | | |
| M2-1 | c7870a | N88K | | | 14 | 66 | 85 | 95 | 100 | 100 |
| M2-1 | u7873c | N89 (silent) | | 16 | 26 | 13 | 6 | | | |
| M2-1 | u7875c | I90T | | 19 | 26 | 12 | 5 | | | |
| M2-1 | u7879c | T91 (silent) | | 14 | 22 | 10 | 4 | | | |
| M2-1 | u7965c | L120P | | 18 | 25 | 12 | 5 | | | |
| M2-1 | u8011c | 1135 (silent) | | 19 | 27 | 12 | 6 | | | |
| L | u8930c[b,c] | G144[b,c] (silent) | | | | | | | 16 | 23 |
| L | u8950c[b] | V151A[b] | | | | | | | 17 | 24 |
| L | u10548c[b] | Y684H[b] | | | 4 | 10 | 12 | | | 20 |
| L | u10556c | D686 (silent) | | | 5 | 6 | 7 | | | |
| L | u10562c[b,c,d] | Y688[b,c] (silent) | | | 7 | 14 | 10 | | | |
| L | u10569c[b] | Y691H[b] | | | 4 | 7 | | | | |
| L | u10571c[b,c,d] | Y691[b,c,d] (silent) | | | 6 | 9 | 10 | | | |
| L | a10572g[b] | I692V[b] | | | 6 | 7 | 6 | | | |
| L | c11995u[b] | T1166I[b] | | | | | | | 40 | 68 |
| L | a12078g | M1194V | | 15 | 19 | 8 | 9 | | | |
| L | c12239u[b,c,d] | N1247[b,c,d] (silent) | | | | | | | 10 | 12 |
| L | a13361c | T1621 (silent) | | | | 5 | 5 | | | |

[a]Percentage of reads with the indicated mutation; only mutations detected in at least 2 consecutive passages with ≥5% of the reads in 1 passage are shown. The temperatures of the specific passages are shown in parentheses. Mutations detected in ≥50% of the reads at a given passage are highlighted in yellow and mutations detected in 25 to 49% of the reads are highlighted in green. Nucleotide numbering is based on RSV sequence M74568.

[b]Mutations involving a codon that had been changed as part of CPD of L.

[c]Mutations involving a nucleotide that had been changed as part of CPD of L.

[d]Mutations involving a nucleotide that had been changed as part of CPD of L and that restored wt sequence.

TABLE S2-A

Accumulation of mutations in passages 1 to 8 (from 37 to 40° C.) in lineage #3 during the temperature stress test[a].

| Gene | Nt mutation | Aa mutation | P1 (37) | P2 (37) | P3 (38) | P4 (38) | P5 (39) | P6 (39) | P7 (40) | P8 (40) |
|---|---|---|---|---|---|---|---|---|---|---|
| | | | Passage (P) number (temperature) and the percentage of reads with the indicated mutation | | | | | | | |
| NS1 | u308c | N70 (silent) | | | | | | | 14 | 25 |
| N | a1547g | K136R | | | | | | 33 | 67 | 66 |
| P | a2687u | E114V | | | 19 | 71 | 87 | 96 | 99 | 100 |
| M2-1 | g7823u | A73S | 13 | 37 | 30 | 12 | 5 | | | |
| M2-1 | u7855c | Y83 (silent) | | 19 | 26 | 12 | 6 | | | |
| M2-1 | u7866c | I87T | | 21 | 29 | 14 | 7 | | | |
| M2-1 | c7870a | N88K | | | 14 | 66 | 85 | 95 | 100 | 100 |
| M2-1 | u7873c | N89 (silent) | | 16 | 26 | 13 | 6 | | | |
| M2-1 | u7875c | I90T | | 19 | 26 | 12 | 5 | | | |
| M2-1 | u7965c | L120P | | 18 | 25 | 12 | 5 | | | |
| M2-1 | u8011c | I135 (silent) | | 19 | 27 | 12 | 6 | | | |
| L | c11995u[b] | T1166I[b] | | | | | | | 40 | 68 |

[a]Percentage of reads with the indicated mutation; only mutations detected in at least 2 consecutive passages with ≥25% of the reads in 1 passage are shown. The temperatures of the specific passages are shown in parentheses. Nucleotide numbering is based on RSV sequence M74568.

bMutations involving a codon that had been changed as part of CPD of L.

[c]Mutations involving a nucleotide that had been changed as part of CPD of L.

[d]Mutations involving a nucleotide that had been changed as part of CPD of L and that restored wt sequence.

TABLE S2-B

Accumulation of mutations in passages 1 to 8 (from 37 to 40° C.) in lineage #3 during the temperature stress test[a].

| | | | Passage (P) number (temperature) and the percentage of reads with the indicated mutation | | | | | | | |
|---|---|---|---|---|---|---|---|---|---|---|
| Gene | Nt mutation | Aa mutation | P1 (37) | P2 (37) | P3 (38) | P4 (38) | P5 (39) | P6 (39) | P7 (40) | P8 (40) |
| N | a1547g | K136R | | | | | | 33 | 67 | 66 |
| P | a2687u | E114V | | | 19 | 71 | 87 | 96 | 99 | 100 |
| M2-1 | c7870a | N88K | | | 14 | 66 | 85 | 95 | 100 | 100 |
| L | c11995u$^{b}$ | T1166I$^{b}$ | | | | | | | 40 | 68 |

[a]Percentage of reads with the indicated mutation; only mutations detected in at least 2 consecutive passages with ≥50% of the reads in 1 passage are shown. The temperatures of the specific passages are shown in parentheses. Nucleotide numbering is based on RSV sequence M74568.

[b]Mutations involving a codon that had been changed as part of CPD of L.

TABLE S3

Accumulation of mutations in passages 1 to 8 (from 37 to 40° C.) in lineage #8 during the temperature stress test[a].

| | | | Passage (P) number (temperature) and the percentage of reads with the indicated mutation | | | | | | | |
|---|---|---|---|---|---|---|---|---|---|---|
| Gene | Nt mutation | Aa mutation | P1 (37) | P2 (37) | P3 (38) | P4 (38) | P5 (39) | P6 (39) | P7 (40) | P8 (40) |
| NS1 | c439a | S114Y | | 7 | 5 | 8 | 5 | 5 | 5 | |
| N | u2127c | A329 (silent) | | | | | | 4 | 28 | 72 |
| P | a2684g | E113G | | | | | | | 33 | 61 |
| Intergene M-SH | a4282g | / | | | | | | | 6 | 44 |
| SH gene end | a4625u | / | | | | | | | | 18 |
| G | a5170g | N161S | | | | | | | | 10 |
| G | c5310u | L208F | | | | | | | | 13 |
| G | u5541c | Y284H | | | | | | | 5 | 34 |
| F | g5800a | A47T | | | | | | | | 10 |
| F | u7298c | L546P | | | | 5 | 9 | 8 | 4 | |
| M2-1 | g7823u | A73S | 13 | 51 | 69 | 88 | 88 | 86 | 94 | 100 |
| M2-1 | u7866c | I87T | | 17 | 10 | 4 | | | | |
| M2-1 | u7866a | I87K | | | | | 5 | 10 | 5 | |
| M2-1 | u7875c | I90T | | 17 | 9 | | | | | |
| M2-1 | u7879c | T91 (silent) | | 15 | 9 | | | | | |
| M2-1 | u7927c | N107 (silent) | | 19 | 11 | 4 | | | | |
| M2-2 | u8279c | N40 (silent) | | 14 | 8 | | | | | |
| M2-2 | u8294c | N45 (silent) | | 16 | 9 | | | | | |
| M2-2 | u8419c | I87T | | 26 | 14 | 4 | | | | |
| M2-2 gene end | u8466c | / | | 24 | 14 | 4 | | | | |
| L | c9156u$^{b}$ | Q220Stop$^{b}$ | | | | | | | | 5 |
| L | a10434u | M646L | | | | | | | 8 | 43 |
| L | g10824u | G776C | | | | | | | | 10 |
| L | a11363g | I955M | | | | | | | 22 | 10 |
| L | g11535a$^{b}$ | V1013I$^{b}$ | | | | | | 6 | 5 | |
| L | a12033c | I1179L | | | | | | | 12 | 43 |
| L | g12933a | A1479T | | 10 | 40 | 76 | 82 | 85 | 94 | 97 |
| L | a13527g | N1677D | | | | | | 5 | 10 | |
| L | c13670u$^{b,c,d}$ | N1724$^{b,c,d}$ (silent) | | | | | | | | 7 |
| L | u13850c$^{b,c,d}$ | G1784$^{b,c,d}$ (silent) | | | | | | | | 5 |
| L | c14204g$^{b,c}$ | Y1902Stop$^{b,c}$ | | | | | | | | 7 |
| L | c14411u$^{b,c}$ | I1971$^{b,c}$ (silent) | | | 6 | 15 | 11 | 17 | 11 | |
| L | u14984c | F2162 (silent) | | | | | | | 44 | 94 |
| 5' UTR | u15100c | / | | 13 | 41 | 86 | 92 | 86 | 95 | 100 |

[a]Percentage of reads with the indicated mutation; only mutations detected in at least 2 consecutive passages with ≥5% of the reads in 1 passage are shown. The temperatures of the specific passages are shown in parentheses. Mutations detected in ≥50% of the reads at a given passage are highlighted in yellow and mutations detected in 25 to 49% of the reads are highlighted in green. Nucleotide numbering is based on RSV sequence M74568.

[b]Mutations involving a codon that had been changed as part of CPD of L.

[c]Mutations involving a nucleotide that had been changed as part of CPD of L.

[d]Mutations involving a nucleotide that had been changed as part of CPD of L and that restored wt sequence.

TABLE S3-A

Accumulation of mutations in passages 1 to 8 (from 37 to 40° C.) in lineage #8 during the temperature stress test[a].

| | | | Passage (P) number (temperature) and the percentage of reads with the indicated mutation | | | | | | | |
|---|---|---|---|---|---|---|---|---|---|---|
| Gene | Nt mutation | Aa mutation | P1 (37) | P2 (37) | P3 (38) | P4 (38) | P5 (39) | P6 (39) | P7 (40) | P8 (40) |
| N | u2127c | A329 (silent) | | | | | | 4 | 28 | 72 |
| P | a2684g | E113G | | | | | | | 33 | 61 |
| Intergene M-SH | a4282g | / | | | | | | | 6 | 44 |
| G | u5541c | Y284H | | | | | | | 5 | 34 |
| M2-1 | g7823u | A73S | 13 | 51 | 69 | 88 | 88 | 86 | 94 | 100 |
| M2-2 | u8419c | I87T | | 26 | 14 | 4 | | | | |
| L | a10434u | M646L | | | | | | | 8 | 43 |
| L | a12033c | I1179L | | | | | | | 12 | 43 |
| L | g12933a | A1479T | | 10 | 40 | 76 | 82 | 85 | 94 | 97 |
| L | u14984c | F2162 (silent) | | | | | | | 44 | 94 |
| 5' UTR | u15100c | / | | 13 | 41 | 86 | 92 | 86 | 95 | 100 |

[a]Percentage of reads with the indicated mutation; only mutations detected in at least 2 consecutive passages with ≥25% of the reads in 1 passage are shown. The temperatures of the specific passages are shown in parentheses. Nucleotide numbering is based on RSV sequence M74568.

TABLE S3-B

Accumulation of mutations in passages 1 to 8 (from 37 to 40° C.) in lineage #8 during the temperature stress test[a].

| | | | Passage (P) number (temperature) and the percentage of reads with the indicated mutation | | | | | | | |
|---|---|---|---|---|---|---|---|---|---|---|
| Gene | Nt mutation | Aa mutation | P1 (37) | P2 (37) | P3 (38) | P4 (38) | P5 (39) | P6 (39) | P7 (40) | P8 (40) |
| N | u2127c | A329 (silent) | | | | | | 4 | 28 | 72 |
| P | a2684g | E113G | | | | | | | 33 | 61 |
| M2-1 | g7823u | A73S | 13 | 51 | 69 | 88 | 88 | 86 | 94 | 100 |
| L | g12933a | A1479T | | 10 | 40 | 76 | 82 | 85 | 94 | 97 |
| L | u14984c | F2162 (silent) | | | | | | | 44 | 94 |
| 5' UTR | u15100c | / | | 13 | 41 | 86 | 92 | 86 | 95 | 100 |

[a]Percentage of reads with the indicated mutation; only mutations detected in at least 2 consecutive passages with ≥50% of the reads in 1 passage are shown. The temperatures of the specific passages are shown in parentheses. Nucleotide numbering is based on RSV sequence M74568.

REFERENCES

1. Abil Z, Xiong X, & Zhao H (2015) Synthetic biology for therapeutic applications. *Mol Pharm* 12(2):322-331.
2. Martinez M A, Jordan-Paiz A, Franco S, & Nevot M (2015) Synonymous Virus Genome Recoding as a Tool to Impact Viral Fitness. *Trends Microbiol.*
3. Gaunt E, et al. (2016) Elevation of CpG frequencies in influenza A genome attenuates pathogenicity but enhances host response to infection. *Elife* 5.
4. Nogales A, et al. (2014) Influenza A virus attenuation by codon deoptimization of the NS gene for vaccine development. *J Virol* 88(18):10525-10540.
5. Broadbent A J, et al. (2015) Evaluation of the attenuation, immunogenicity, and efficacy of a live virus vaccine generated by codon-pair bias de-optimization of the 2009 pandemic H1N1 influenza virus, in ferrets. *Vaccine.*
6. Cheng B Y, Ortiz-Riano E, Nogales A, de la Torre J C, & Martinez-Sobrido L (2015) Development of live-attenuated arenavirus vaccines based on codon deoptimization. *J Virol* 89(7):3523-3533.
7. Diaz-San Segundo F, et al. (2015) Synonymous deoptimization of the foot-and-mouth disease virus causes attenuation in vivo while inducing a strong neutralizing antibody response. *J Virol.*
8. Coleman J R, et al. (2008) Virus attenuation by genome-scale changes in codon pair bias. *Science* 320(5884):1784-1787.
9. Yang C, Skiena S, Futcher B, Mueller S, & Wimmer E (2013) Deliberate reduction of hemagglutinin and neuraminidase expression of influenza virus leads to an ultraprotective live vaccine in mice. *Proc Natl Acad Sci USA* 110(23):9481-9486.
10. Kunec D & Osterrieder N (2015) Codon Pair Bias Is a Direct Consequence of Dinucleotide Bias. *Cell reports.*
11. Tulloch F, Atkinson N J, Evans D J, Ryan M D, & Simmonds P (2014) RNA virus attenuation by codon pair deoptimisation is an artefact of increases in CpG/UpA dinucleotide frequencies. *Elife* 3:e04531.
12. Shen S H, et al. (2015) Large-scale recoding of an arbovirus genome to rebalance its insect versus mammalian preference. *Proc Natl Acad Sci USA* 112(15):4749-4754.
13. Lauring A S, Jones J O, & Andino R (2010) Rationalizing the development of live attenuated virus vaccines. *Nat Biotechnol* 28(6):573-579.
14. Hanley K A (2011) The double-edged sword: How evolution can make or break a live-attenuated virus vaccine. *Evolution (NY)* 4(4):635-643.

15. Bull J J (2015) Evolutionary reversion of live viral vaccines: Can genetic engineering subdue it? *Virus Evolution* 1(1):vev005.
16. Burns C C, et al. (2006) Modulation of poliovirus replicative fitness in HeLa cells by deoptimization of synonymous codon usage in the capsid region. *J Virol* 80(7):3259-3272.
17. Mueller S, Papamichail D, Coleman J R, Skiena S, & Wimmer E (2006) Reduction of the rate of poliovirus protein synthesis through large-scale codon deoptimization causes attenuation of viral virulence by lowering specific infectivity. *J Virol* 80(19):9687-9696.
18. Bull J J, Molineux I J, & Wilke C O (2012) Slow fitness recovery in a codon-modified viral genome. *Mol Biol Evol* 29(10):2997-3004.
19. Nougairede A, et al. (2013) Random codon re-encoding induces stable reduction of replicative fitness of Chikungunya virus in primate and mosquito cells. *PLoS Pathog* 9(2):e1003172.
20. Vabret N, et al. (2014) Large-scale nucleotide optimization of simian immunodeficiency virus reduces its capacity to stimulate type I interferon in vitro. *J Virol* 88(8):4161-4172.
21. Meng J, Lee S, Hotard A L, & Moore M L (2014) Refining the balance of attenuation and immunogenicity of respiratory syncytial virus by targeted codon deoptimization of virulence genes. *MBio* 5(5):e01704-01714.
22. Ni Y Y, et al. (2014) Computer-aided codon-pairs deoptimization of the major envelope GP5 gene attenuates porcine reproductive and respiratory syndrome virus. *Virology* 450-451:132-139.
23. Le Nouen C, et al. (2014) Attenuation of human respiratory syncytial virus by genome-scale codon-pair deoptimization. *Proc Natl Acad Sci USA* 111(36):13169-13174.
24. White M D, Bosio C M, Duplantis B N, & Nano F E (2011) Human body temperature and new approaches to constructing temperature-sensitive bacterial vaccines. *Cellular and molecular life sciences: CMLS* 68(18):3019-3031.
25. Nielsen R (2005) Molecular signatures of natural selection. *Annu Rev Genet* 39:197-218.
26. Fearns R & Collins P L (1999) Role of the M2-1 transcription antitermination protein of respiratory syncytial virus in sequential transcription. *J Virol* 73(7):5852-5864.
27. Tanner S J, et al. (2014) Crystal structure of the essential transcription antiterminator M2-1 protein of human respiratory syncytial virus and implications of its phosphorylation. *Proc Natl Acad Sci USA* 111(4):1580-1585.
28. Tran T L, et al. (2009) The respiratory syncytial virus M2-1 protein forms tetramers and interacts with RNA and P in a competitive manner. *J Virol* 83(13):6363-6374.
29. Blondot M L, et al. (2012) Structure and functional analysis of the RNA- and viral phosphoprotein-binding domain of respiratory syncytial virus M2-1 protein. *PLoS Pathog* 8(5):e1002734.
30. Mason S W, et al. (2003) Interaction between human respiratory syncytial virus (RSV) M2-1 and P proteins is required for reconstitution of M2-1-dependent RSV minigenome activity. *J Virol* 77(19):10670-10676.
31. Chapman M A, et al. (2011) Initial genome sequencing and analysis of multiple myeloma. *Nature* 471(7339):467-472.
32. Mueller S, et al. (2010) Live attenuated influenza virus vaccines by computer-aided rational design. *Nat Biotechnol* 28(7):723-726.
33. Bukreyev A, Belyakov I M, Berzofsky J A, Murphy B R, & Collins P L (2001) Granulocyte-macrophage colony-stimulating factor expressed by recombinant respiratory syncytial virus attenuates viral replication and increases the level of pulmonary antigen-presenting cells. *J Virol* 75(24):12128-12140.
34. Rothberg J M, et al. (2011) An integrated semiconductor device enabling non-optical genome sequencing. *Nature* 475(7356):348-352.
35. Buchholz U J, Finke S, & Conzelmann K K (1999) Generation of bovine respiratory syncytial virus (BRSV) from cDNA: BRSV NS2 is not essential for virus replication in tissue culture, and the human RSV leader region acts as a functional BRSV genome promoter. *J Virol* 73(1):251-259.
35. Collins P L, et al. (1995) Production of infectious human respiratory syncytial virus from cloned cDNA confirms an essential role for the transcription elongation factor from the 5' proximal open reading frame of the M2 mRNA in gene expression and provides a capability for vaccine development. *Proc Natl Acad Sci USA* 92(25):11563-11567.
37. Crowe J E, Jr., Collins P L, London W T, Chanock R M, & Murphy B R (1993) A comparison in chimpanzees of the immunogenicity and efficacy of live attenuated respiratory syncytial virus (RSV) temperature-sensitive mutant vaccines and vaccinia virus recombinants that express the surface glycoproteins of RSV. *Vaccine* 11(14):1395-1404.
38. Liang B, et al. (2015) Enhanced Neutralizing Antibody Response Induced by Respiratory Syncytial Virus Prefusion F Protein Expressed by a Vaccine Candidate *J Virol.*
39. Humphrey W, Dalke A, & Schulten K (1996) VMD: visual molecular dynamics *J Mol Graph* 14(1):33-38, 27-38.
40. Phillips J C, et al. (2005) Scalable molecular dynamics with NAMD. *J Comput Chem* 26(16):1781-1802.
41. Brooks B R, et al. (2009) CHARMM: the biomolecular simulation program. *J Comput Chem* 30(10):1545-1614.

The invention claimed is:

1. An isolated polynucleotide molecule encoding a recombinant respiratory syncytial virus (RSV) variant having an attenuated phenotype comprising a RSV genome or antigenome sequence, wherein the RSV genome or antigenome is modified by a mutation in the L ORF at a position corresponding to T1166 of the L protein in SEQ ID NO:11 and further modified by at least two mutations selected from the group consisting of:

i. a mutation in the M2-1 ORF at a position corresponding to N88 or A73 of the M2-1 protein in SEQ ID NO:9;

ii. a mutation in the N ORF at a position corresponding to K136 of the N protein in SEQ ID NO:3;

iii. a mutation in the P ORF at a position corresponding to E114 of the P protein in SEQ ID NO:4; and iv. combinations thereof.

2. The isolated polynucleotide molecule of claim 1, wherein the RSV genome or antigenome is further modified by the following mutations:

i. a mutation in the M2-1 ORF at a position corresponding to N88 of the M2-1 protein in SEQ ID NO:9;

ii. a mutation in the N ORF at a position corresponding to K136 of the N protein in SEQ ID NO:3; and iii. a mutation in the P ORF at a position corresponding to E114 of the P protein in SEQ ID NO:4.

3. The isolated polynucleotide molecule of claim 1, wherein the RSV genome or antigenome is further modified by the following mutations:

i. a mutation in the M2-1 ORF at a position corresponding to A73 of the M2-1 protein in SEQ ID NO:9;

ii. a mutation in the N ORF at a position corresponding to K136 of the N protein in SEQ ID NO:3; and iii. a mutation in the P ORF at a position corresponding to E114 of the P protein in SEQ ID NO:4.

4. The isolated polynucleotide molecule of claim 1, wherein the RSV genome or antigenome is modified by corresponding mutations selected from the group consisting of (1) T1166I in the L protein, N88K in the M2-1 protein, K136R in the N protein and E114V in the P protein; and (2) T1166I in the L protein, A73S in the M2-1 protein, K136R in the N protein and E114V in the P protein.

5. The isolated polynucleotide molecule of claim 4, wherein the RSV genome or antigenome comprises a deletion in at least one of the proteins selected from M2-2, NS1 and NS2.

6. The isolated polynucleotide molecule of claim 4, wherein the RSV genome or antigenome is codon-pair deoptimized.

7. The isolated polynucleotide molecule of claim 4, wherein the L ORF of the RSV genome or antigenome is codon-pair deoptimized.

8. A vector comprising the isolated polynucleotide molecule of claim 1.

9. A cell comprising the isolated polynucleotide of claim 1.

10. A pharmaceutical composition comprising an immunologically effective amount of the recombinant RSV variant encoded by the isolated polynucleotide molecule of claim 1.

11. A method of vaccinating a subject against RSV comprising administering the pharmaceutical composition of claim 10.

12. A method of inducing an immune response comprising administering the pharmaceutical composition of claim 10.

13. The method of claim 11, wherein the pharmaceutical composition is administered intranasally via injection, aerosol delivery, nasal spray or nasal droplets.

14. A live attenuated RSV vaccine comprising the recombinant RSV variant encoded by the isolated polynucleotide of claim 4.

15. A pharmaceutical composition comprising the RSV vaccine of claim 14.

16. A method of making a live attenuated RSV vaccine comprising expressing the isolated polynucleotide molecule of claim 4.

17. An isolated polynucleotide molecule that is at least about 95% identical to the nucleotide sequence of SEQ ID NO:14.

18. The isolated polynucleotide molecule of claim 17, comprising the nucleotide sequence of SEQ ID NO:14.

19. A vector comprising the isolated polynucleotide molecule of claim 18.

20. A cell comprising the isolated polynucleotide of claim 18.

21. A pharmaceutical composition comprising an immunologically effective amount of the recombinant RSV variant encoded by the isolated polynucleotide molecule of claim 18.

22. A method of vaccinating a subject against RSV comprising administering the pharmaceutical composition of claim 21.

23. A method of inducing an immune response comprising administering the pharmaceutical composition of claim 21.

24. The method of claim 22, wherein the pharmaceutical composition is administered intranasally.

25. The method of claim 24, wherein the pharmaceutical composition is administered via injection, aerosol delivery, nasal spray or nasal droplets.

26. A live attenuated RSV vaccine comprising the recombinant RSV variant encoded by the isolated polynucleotide of claim 18.

27. A pharmaceutical composition comprising the RSV vaccine of claim 26.

28. A method of making a live attenuated RSV vaccine comprising expressing the isolated polynucleotide molecule of claim 18.

* * * * *

SEQUENCE LISTING

```
<160> NUMBER OF SEQ ID NOS: 14

<210> SEQ ID NO 1
<211> LENGTH: 139
<212> TYPE: PRT
<213> ORGANISM: RESPIRATORY SYNCYTIAL VIRUS

<400> SEQUENCE: 1

Met Gly Ser Asn Ser Leu Ser Met Ile Lys Val Arg Leu Gln Asn Leu
1               5                   10                  15
```

Phe Asp Asn Asp Glu Val Ala Leu Leu Lys Ile Thr Cys Tyr Thr Asp
20 25 30

Lys Leu Ile His Leu Thr Asn Ala Leu Ala Lys Ala Val Ile His Thr
35 40 45

Ile Lys Leu Asn Gly Ile Val Phe Val His Val Ile Thr Ser Ser Asp
50 55 60

Ile Cys Pro Asn Asn Asn Ile Val Val Lys Ser Asn Phe Thr Thr Met
65 70 75 80

Pro Val Leu Gln Asn Gly Gly Tyr Ile Trp Glu Met Met Glu Leu Thr
85 90 95

His Cys Ser Gln Pro Asn Gly Leu Leu Asp Asp Asn Cys Glu Ile Lys
100 105 110

Phe Ser Lys Lys Leu Ser Asp Ser Thr Met Thr Asn Tyr Met Asn Gln
115 120 125

Leu Ser Glu Leu Leu Gly Phe Asp Leu Asn Pro
130 135

<210> SEQ ID NO 2
<211> LENGTH: 124
<212> TYPE: PRT
<213> ORGANISM: RESPIRATORY SYNCYTIAL VIRUS

<400> SEQUENCE: 2

Met Asp Thr Thr His Asn Asp Asn Thr Pro Gln Arg Leu Met Ile Thr
1 5 10 15

Asp Met Arg Pro Leu Ser Leu Glu Thr Ile Ile Thr Ser Leu Thr Arg
20 25 30

Asp Ile Ile Thr His Lys Phe Ile Tyr Leu Ile Asn His Glu Cys Ile
35 40 45

Val Arg Lys Leu Asp Glu Arg Gln Ala Thr Phe Thr Phe Leu Val Asn
50 55 60

Tyr Glu Met Lys Leu Leu His Lys Val Gly Ser Thr Lys Tyr Lys Lys
65 70 75 80

Tyr Thr Glu Tyr Asn Thr Lys Tyr Gly Thr Phe Pro Met Pro Ile Phe
85 90 95

Ile Asn His Asp Gly Phe Leu Glu Cys Ile Gly Ile Lys Pro Thr Lys
100 105 110

His Thr Pro Ile Ile Tyr Lys Tyr Asp Leu Asn Pro
115 120

<210> SEQ ID NO 3
<211> LENGTH: 391
<212> TYPE: PRT
<213> ORGANISM: RESPIRATORY SYNCYTIAL VIRUS

<400> SEQUENCE: 3

Met Ala Leu Ser Lys Val Lys Leu Asn Asp Thr Leu Asn Lys Asp Gln
1 5 10 15

Leu Leu Ser Ser Ser Lys Tyr Thr Ile Gln Arg Ser Thr Gly Asp Ser
20 25 30

Ile Asp Thr Pro Asn Tyr Asp Val Gln Lys His Ile Asn Lys Leu Cys
35 40 45

Gly Met Leu Leu Ile Thr Glu Asp Ala Asn His Lys Phe Thr Gly Leu
50 55 60

Ile Gly Met Leu Tyr Ala Met Ser Arg Leu Gly Arg Glu Asp Thr Ile
65 70 75 80

```
Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
        195                 200                 205

Phe Tyr Glu Val Phe Glu Lys His Pro His Phe Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu
385                 390


<210> SEQ ID NO 4
<211> LENGTH: 241
<212> TYPE: PRT
<213> ORGANISM: RESPIRATORY SYNCYTIAL VIRUS

<400> SEQUENCE: 4

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
```

```
    50                  55                  60

Pro Thr Asn Glu Thr Asp Asp Thr Ala Gly Asn Lys Pro Asn Tyr Gln
65                  70                  75                  80

Arg Lys Pro Leu Val Ser Phe Lys Glu Asp Pro Thr Pro Ser Asp Asn
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175

Met Ile Glu Lys Ile Arg Thr Glu Ala Leu Met Thr Asn Asp Arg Leu
            180                 185                 190

Glu Ala Met Ala Arg Leu Arg Asn Glu Glu Ser Glu Lys Met Ala Lys
        195                 200                 205

Asp Thr Ser Asp Glu Val Ser Leu Asn Pro Thr Ser Glu Lys Leu Asn
    210                 215                 220

Asn Leu Leu Glu Gly Asn Asp Ser Asp Asn Asp Leu Ser Leu Glu Asp
225                 230                 235                 240

Phe


<210> SEQ ID NO 5
<211> LENGTH: 256
<212> TYPE: PRT
<213> ORGANISM: RESPIRATORY SYNCYTIAL VIRUS

<400> SEQUENCE: 5

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
```

-continued

```
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 6
<211> LENGTH: 64
<212> TYPE: PRT
<213> ORGANISM: RESPIRATORY SYNCYTIAL VIRUS

<400> SEQUENCE: 6

Met Glu Asn Thr Ser Ile Thr Ile Glu Phe Ser Ser Lys Phe Trp Pro
1               5                   10                  15

Tyr Phe Thr Leu Ile His Met Ile Thr Thr Ile Ile Ser Leu Leu Ile
            20                  25                  30

Ile Ile Ser Ile Met Ile Ala Ile Leu Asn Lys Leu Cys Glu Tyr Asn
        35                  40                  45

Val Phe His Asn Lys Thr Phe Glu Leu Pro Arg Ala Arg Val Asn Thr
    50                  55                  60


<210> SEQ ID NO 7
<211> LENGTH: 298
<212> TYPE: PRT
<213> ORGANISM: RESPIRATORY SYNCYTIAL VIRUS

<400> SEQUENCE: 7

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
```

-continued

```
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295


<210> SEQ ID NO 8
<211> LENGTH: 574
<212> TYPE: PRT
<213> ORGANISM: RESPIRATORY SYNCYTIAL VIRUS

<400> SEQUENCE: 8

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

```
Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 9
<211> LENGTH: 194
<212> TYPE: PRT
<213> ORGANISM: RESPIRATORY SYNCYTIAL VIRUS

<400> SEQUENCE: 9

```
Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45

Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Val Val Gly Val Leu
65                  70                  75                  80
```

Glu Ser Tyr Ile Gly Ser Ile Asn Asn Ile Thr Lys Gln Ser Ala Cys
85 90 95

Val Ala Met Ser Lys Leu Leu Thr Glu Leu Asn Ser Asp Asp Ile Lys
100 105 110

Lys Leu Arg Asp Asn Glu Glu Leu Asn Ser Pro Lys Ile Arg Val Tyr
115 120 125

Asn Thr Val Ile Ser Tyr Ile Glu Ser Asn Arg Lys Asn Asn Lys Gln
130 135 140

Thr Ile His Leu Leu Lys Arg Leu Pro Ala Asp Val Leu Lys Lys Thr
145 150 155 160

Ile Lys Asn Thr Leu Asp Ile His Lys Ser Ile Thr Ile Asn Asn Pro
165 170 175

Lys Glu Ser Thr Val Ser Asp Thr Asn Asp His Ala Lys Asn Asn Asp
180 185 190

Thr Thr

<210> SEQ ID NO 10
<211> LENGTH: 90
<212> TYPE: PRT
<213> ORGANISM: RESPIRATORY SYNCYTIAL VIRUS

<400> SEQUENCE: 10

Met Thr Met Pro Lys Ile Met Ile Leu Pro Asp Lys Tyr Pro Cys Ser
1 5 10 15

Ile Thr Ser Ile Leu Ile Thr Ser Arg Cys Arg Val Thr Met Tyr Asn
20 25 30

Gln Lys Asn Thr Leu Tyr Phe Asn Gln Asn Asn Pro Asn Asn His Met
35 40 45

Tyr Ser Pro Asn Gln Thr Phe Asn Glu Ile His Trp Thr Ser Gln Glu
50 55 60

Leu Ile Asp Thr Ile Gln Asn Phe Leu Gln His Leu Gly Ile Ile Glu
65 70 75 80

Asp Ile Tyr Thr Ile Tyr Ile Leu Val Ser
85 90

<210> SEQ ID NO 11
<211> LENGTH: 2165
<212> TYPE: PRT
<213> ORGANISM: RESPIRATORY SYNCYTIAL VIRUS

<400> SEQUENCE: 11

Met Asp Pro Ile Ile Asn Gly Asn Ser Ala Asn Val Tyr Leu Thr Asp
1 5 10 15

Ser Tyr Leu Lys Gly Val Ile Ser Phe Ser Glu Cys Asn Ala Leu Gly
20 25 30

Ser Tyr Ile Phe Asn Gly Pro Tyr Leu Lys Asn Asp Tyr Thr Asn Leu
35 40 45

Ile Ser Arg Gln Asn Pro Leu Ile Glu His Met Asn Leu Lys Lys Leu
50 55 60

Asn Ile Thr Gln Ser Leu Ile Ser Lys Tyr His Lys Gly Glu Ile Lys
65 70 75 80

Leu Glu Glu Pro Thr Tyr Phe Gln Ser Leu Leu Met Thr Tyr Lys Ser
85 90 95

Met Thr Ser Ser Glu Gln Ile Ala Thr Thr Asn Leu Leu Lys Lys Ile
100 105 110

-continued

```
Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Ile Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
```

```
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
        595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
            740                 745                 750

Ile Gly Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Ile Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Val Trp Leu Tyr Asn Gln Ile Ala Leu Gln Leu Lys Asn His
    930                 935                 940

Ala Leu Cys Asn Asn Lys Leu Tyr Leu Asp Ile Leu Lys Val Leu Lys
945                 950                 955                 960
```

His Leu Lys Thr Phe Phe Asn Leu Asp Asn Ile Asp Thr Ala Leu Thr
965 970 975

Leu Tyr Met Asn Leu Pro Met Leu Phe Gly Gly Gly Asp Pro Asn Leu
980 985 990

Leu Tyr Arg Ser Phe Tyr Arg Arg Thr Pro Asp Phe Leu Thr Glu Ala
995 1000 1005

Ile Val His Ser Val Phe Ile Leu Ser Tyr Tyr Thr Asn His Asp
1010 1015 1020

Leu Lys Asp Lys Leu Gln Asp Leu Ser Asp Asp Arg Leu Asn Lys
1025 1030 1035

Phe Leu Thr Cys Ile Ile Thr Phe Asp Lys Asn Pro Asn Ala Glu
1040 1045 1050

Phe Val Thr Leu Met Arg Asp Pro Gln Ala Leu Gly Ser Glu Arg
1055 1060 1065

Gln Ala Lys Ile Thr Ser Glu Ile Asn Arg Leu Ala Val Thr Glu
1070 1075 1080

Val Leu Ser Thr Ala Pro Asn Lys Ile Phe Ser Lys Ser Ala Gln
1085 1090 1095

His Tyr Thr Thr Thr Glu Ile Asp Leu Asn Asp Ile Met Gln Asn
1100 1105 1110

Ile Glu Pro Thr Tyr Pro His Gly Leu Arg Val Val Tyr Glu Ser
1115 1120 1125

Leu Pro Phe Tyr Lys Ala Glu Lys Ile Val Asn Leu Ile Ser Gly
1130 1135 1140

Thr Lys Ser Ile Thr Asn Ile Leu Glu Lys Thr Ser Ala Ile Asp
1145 1150 1155

Leu Thr Asp Ile Asp Arg Ala Thr Glu Met Met Arg Lys Asn Ile
1160 1165 1170

Thr Leu Leu Ile Arg Ile Leu Pro Leu Asp Cys Asn Arg Asp Lys
1175 1180 1185

Arg Glu Ile Leu Ser Met Glu Asn Leu Ser Ile Thr Glu Leu Ser
1190 1195 1200

Lys Tyr Val Arg Glu Arg Ser Trp Ser Leu Ser Asn Ile Val Gly
1205 1210 1215

Val Thr Ser Pro Ser Ile Met Tyr Thr Met Asp Ile Lys Tyr Thr
1220 1225 1230

Thr Ser Thr Ile Ser Ser Gly Ile Ile Ile Glu Lys Tyr Asn Val
1235 1240 1245

Asn Ser Leu Thr Arg Gly Glu Arg Gly Pro Thr Lys Pro Trp Val
1250 1255 1260

Gly Ser Ser Thr Gln Glu Lys Lys Thr Met Pro Val Tyr Asn Arg
1265 1270 1275

Gln Val Leu Thr Lys Lys Gln Arg Asp Gln Ile Asp Leu Leu Ala
1280 1285 1290

Lys Leu Asp Trp Val Tyr Ala Ser Ile Asp Asn Lys Asp Glu Phe
1295 1300 1305

Met Glu Glu Leu Ser Ile Gly Thr Leu Gly Leu Thr Tyr Glu Lys
1310 1315 1320

Ala Lys Lys Leu Phe Pro Gln Tyr Leu Ser Val Asn Tyr Leu His
1325 1330 1335

Arg Leu Thr Val Ser Ser Arg Pro Cys Glu Phe Pro Ala Ser Ile
1340 1345 1350

-continued

```
Pro Ala  Tyr Arg Thr Thr Asn  Tyr His Phe Asp Thr  Ser Pro Ile
    1355                1360                 1365

Asn Arg  Ile Leu Thr Glu Lys  Tyr Gly Asp Glu Asp  Ile Asp Ile
    1370                1375                 1380

Val Phe  Gln Asn Cys Ile Ser  Phe Gly Leu Ser Leu  Met Ser Val
    1385                1390                 1395

Val Glu  Gln Phe Thr Asn Val  Cys Pro Asn Arg Ile  Ile Leu Ile
    1400                1405                 1410

Pro Lys  Leu Asn Glu Ile His  Leu Met Lys Pro Pro  Ile Phe Thr
    1415                1420                 1425

Gly Asp  Val Asp Ile His Lys  Leu Lys Gln Val Ile  Gln Lys Gln
    1430                1435                 1440

His Met  Phe Leu Pro Asp Lys  Ile Ser Leu Thr Gln  Tyr Val Glu
    1445                1450                 1455

Leu Phe  Leu Ser Asn Lys Thr  Leu Lys Ser Gly Ser  His Val Asn
    1460                1465                 1470

Ser Asn  Leu Ile Leu Ala His  Lys Ile Ser Asp Tyr  Phe His Asn
    1475                1480                 1485

Thr Tyr  Ile Leu Ser Thr Asn  Leu Ala Gly His Trp  Ile Leu Ile
    1490                1495                 1500

Ile Gln  Leu Met Lys Asp Ser  Lys Gly Ile Phe Glu  Lys Asp Trp
    1505                1510                 1515

Gly Glu  Gly Tyr Ile Thr Asp  His Met Phe Ile Asn  Leu Lys Val
    1520                1525                 1530

Phe Phe  Asn Ala Tyr Lys Thr  Tyr Leu Leu Cys Phe  His Lys Gly
    1535                1540                 1545

Tyr Gly  Lys Ala Lys Leu Glu  Cys Asp Met Asn Thr  Ser Asp Leu
    1550                1555                 1560

Leu Cys  Val Leu Glu Leu Ile  Asp Ser Ser Tyr Trp  Lys Ser Met
    1565                1570                 1575

Ser Lys  Val Phe Leu Glu Gln  Lys Val Ile Lys Tyr  Ile Leu Ser
    1580                1585                 1590

Gln Asp  Ala Ser Leu His Arg  Val Lys Gly Cys His  Ser Phe Lys
    1595                1600                 1605

Leu Trp  Phe Leu Lys Arg Leu  Asn Val Ala Glu Phe  Thr Val Cys
    1610                1615                 1620

Pro Trp  Val Val Asn Ile Asp  Tyr His Pro Thr His  Met Lys Ala
    1625                1630                 1635

Ile Leu  Thr Tyr Ile Asp Leu  Val Arg Met Gly Leu  Ile Asn Ile
    1640                1645                 1650

Asp Arg  Ile His Ile Lys Asn  Lys His Lys Phe Asn  Asp Glu Phe
    1655                1660                 1665

Tyr Thr  Ser Asn Leu Phe Tyr  Ile Asn Tyr Asn Phe  Ser Asp Asn
    1670                1675                 1680

Thr His  Leu Leu Thr Lys His  Ile Arg Ile Ala Asn  Ser Glu Leu
    1685                1690                 1695

Glu Asn  Asn Tyr Asn Lys Leu  Tyr His Pro Thr Pro  Glu Thr Leu
    1700                1705                 1710

Glu Asn  Ile Leu Ala Asn Pro  Ile Lys Ser Asn Asp  Lys Lys Thr
    1715                1720                 1725

Leu Asn  Asp Tyr Cys Ile Gly  Lys Asn Val Asp Ser  Ile Met Leu
    1730                1735                 1740

Pro Leu  Leu Ser Asn Lys Lys  Leu Ile Lys Ser Ser  Ala Met Ile
```

```
    1745                1750                1755

Arg Thr  Asn Tyr Ser Lys Gln  Asp Leu Tyr Asn Leu  Phe Pro Met
    1760                1765                1770

Val Val  Ile Asp Arg Ile Ile  Asp His Ser Gly Asn  Thr Ala Lys
    1775                1780                1785

Ser Asn  Gln Leu Tyr Thr Thr  Thr Ser His Gln Ile  Ser Leu Val
    1790                1795                1800

His Asn  Ser Thr Ser Leu Tyr  Cys Met Leu Pro Trp  His His Ile
    1805                1810                1815

Asn Arg  Phe Asn Phe Val Phe  Ser Ser Thr Gly Cys  Lys Ile Ser
    1820                1825                1830

Ile Glu  Tyr Ile Leu Lys Asp  Leu Lys Ile Lys Asp  Pro Asn Cys
    1835                1840                1845

Ile Ala  Phe Ile Gly Glu Gly  Ala Gly Asn Leu Leu  Leu Arg Thr
    1850                1855                1860

Val Val  Glu Leu His Pro Asp  Ile Arg Tyr Ile Tyr  Arg Ser Leu
    1865                1870                1875

Lys Asp  Cys Asn Asp His Ser  Leu Pro Ile Glu Phe  Leu Arg Leu
    1880                1885                1890

Tyr Asn  Gly His Ile Asn Ile  Asp Tyr Gly Glu Asn  Leu Thr Ile
    1895                1900                1905

Pro Ala  Thr Asp Ala Thr Asn  Asn Ile His Trp Ser  Tyr Leu His
    1910                1915                1920

Ile Lys  Phe Ala Glu Pro Ile  Ser Leu Phe Val Cys  Asp Ala Glu
    1925                1930                1935

Leu Ser  Val Thr Val Asn Trp  Ser Lys Ile Ile Ile  Glu Trp Ser
    1940                1945                1950

Lys His  Val Arg Lys Cys Lys  Tyr Cys Ser Ser Val  Asn Lys Cys
    1955                1960                1965

Met Leu  Ile Val Lys Tyr His  Ala Gln Asp Asp Ile  Asp Phe Lys
    1970                1975                1980

Leu Asp  Asn Ile Thr Ile Leu  Lys Thr Tyr Val Cys  Leu Gly Ser
    1985                1990                1995

Lys Leu  Lys Gly Ser Glu Val  Tyr Leu Val Leu Thr  Ile Gly Pro
    2000                2005                2010

Ala Asn  Ile Phe Pro Val Phe  Asn Val Val Gln Asn  Ala Lys Leu
    2015                2020                2025

Ile Leu  Ser Arg Thr Lys Asn  Phe Ile Met Pro Lys  Lys Ala Asp
    2030                2035                2040

Lys Glu  Ser Ile Asp Ala Asn  Ile Lys Ser Leu Ile  Pro Phe Leu
    2045                2050                2055

Cys Tyr  Pro Ile Thr Lys Lys  Gly Ile Asn Thr Ala  Leu Ser Lys
    2060                2065                2070

Leu Lys  Ser Val Val Ser Gly  Asp Ile Leu Ser Tyr  Ser Ile Ala
    2075                2080                2085

Gly Arg  Asn Glu Val Phe Ser  Asn Lys Leu Ile Asn  His Lys His
    2090                2095                2100

Met Asn  Ile Leu Lys Trp Phe  Asn His Val Leu Asn  Phe Arg Ser
    2105                2110                2115

Thr Glu  Leu Asn Tyr Asn His  Leu Tyr Met Val Glu  Ser Thr Tyr
    2120                2125                2130

Pro Tyr  Leu Ser Glu Leu Leu  Asn Ser Leu Thr Thr  Asn Glu Leu
    2135                2140                2145
```

```
Lys Lys  Leu Ile Lys Ile Thr  Gly Ser Leu Leu Tyr  Asn Phe His
    2150                 2155                 2160

Asn Glu
    2165


<210> SEQ ID NO 12
<211> LENGTH: 15111
<212> TYPE: DNA
<213> ORGANISM: respiratory syncytial virus Min_FLC

<400> SEQUENCE: 12

acgggaaaaa atgcgtacaa caaacttgca taaaccaaaa aaatggggca aataagaatt     60

tgataagtac cacttaaatt taactccctt ggttagagat gggcagcaat tcattgagta    120

tgataaaagt cagattgcaa aatctattcg ataatgacga agtggcacta ttaaaaatta    180

catgttatac cgataaattg atacatctaa ctaatgcatt agctaaagct gtaatacata    240

caattaaact taatggaata gtgtttgtac atgtaattac atctagtgat atatgcccta    300

ataataatat cgtagtcaag tctaatttta caacaatgcc agtgttacaa aatggcggat    360

atatttggga aatgatggaa ttgacacatt gctcacaacc taatggtcta ttagacgata    420

attgcgaaat taaatttagt aagaaattat ccgatagtac aatgactaat tatatgaatc    480

aattatccga attgttaggt ttcgatctta atccataaat tataattaat atcaactagc    540

aaatcaatgt cactaacacc attagttaat ataaaactta acagaagaca aaaatggggc    600

aaataaatca attcagccaa cccaaccatg gacacaaccc acaatgataa tacaccacaa    660

agactgatga ttaccgatat gagaccgttg tcacttgaga caattataac tagcctaact    720

agagatataa taacacataa atttatatat ctgattaatc acgaatgcat cgtgaggaaa    780

ttggacgaaa gacaggccac atttacattc ttagtcaatt acgaaatgaa actattgcat    840

aaggtaggct caactaagta taagaaatat accgaatata acactaaata cggaacattc    900

ccaatgccta tattcataaa tcacgacggg tttctcgaat gcataggcat aaaacctaca    960

aaacatacac ccataatcta taaatacgat cttaacccat aaatttcaac acaatattca   1020

cacaatctaa aacaacaact ctatgcataa ctatactcca tagtccagat ggagcctgaa   1080

aattatagta atttaaaact taaggagaga tataagatag aagatggggc aaatacaacc   1140

atggctctta gcaaagtcaa gttgaatgat acattgaata aagatcaatt actatctagc   1200

tcgaaatata ctatccaacg gtctacaggc gattcaatag atacacctaa ttacgatgtg   1260

caaaaacata ttaataaatt gtgtggtatg ttattgatta ccgaagacgc aaatcataaa   1320

tttacagggt taatcggtat gttatacgct atgtctagat taggtaggga agatacaatt   1380

aaaatactta gagacgcagg atatcacgtt aaagctaacg gagtagacgt aactacacat   1440

agacaggata ttaacggtaa ggaaatgaaa ttcgaagtgt taacactcgc tagcttaact   1500

accgaaatac aaattaatat cgaaatcgaa tcacgtaaat cttataagaa aatgcttaaa   1560

gaaatgggcg aagtcgcacc cgaatataga cacgatagtc ccgattgtgg tatgattata   1620

ctatgtatag ccgcattagt gataactaag ttggccgcag gcgatagatc cggattaacc   1680

gcagtgatac gtagagcgaa taacgtactt aaaaacgaaa tgaaacggta taagggtcta   1740

ttaccaaaag atatagcgaa tagtttttac gaagtattcg aaaaacatcc acattttata   1800

gacgtttttg tgcatttcgg aatcgcacaa tctagtacta gaggaggatc tagggttgag   1860

ggtatattcg caggattgtt tatgaacgca tacggagcag gtcaagtcat gcttagatgg   1920
```

```
ggagtactcg caaaatccgt taaaaatatt atgttaggac acgctagcgt acaagccgaa   1980

atggaacaag tcgttgaggt atacgaatac gcacaaaaat taggtggaga agcaggattt   2040

tatcatatac tgaataatcc taaagctagt ctattaagct taacacaatt tccacatttt   2100

tctagcgtag tgttaggtaa cgcagctggc ctaggcataa tgggcgaata taggggtaca   2160

cctagaaatc aggatctata tgacgcagct aaagcatacg ctgaacaatt gaaagagaat   2220

ggagtgataa attattccgt actcgatcta acagccgaag agttggaggc aattaaacat   2280

caattgaatc cgaaagataa tgacgttgag ttgtgagtta ataaaaaatg gggcaaataa   2340

atcatcatgg aaaagtttgc tcctgaattc catggagaag acgcaaataa tagggcaaca   2400

aaattcttag agtcaatcaa gggtaagttt acaagtccaa aagatccaaa gaagaaagat   2460

agtataataa gcgtaaactc aattgatatc gaggtgacaa aggaatcacc tataacatct   2520

aatagtacaa taataaatcc cactaacgaa acagacgata ccgcaggcaa taaacctaat   2580

tatcaacgga aacccttagt gtcattcaaa gaagatccaa cacctagtga taatcccttt   2640

agtaaattgt ataaggaaac aatcgaaaca ttcgataata acgaagaaga atcatcatac   2700

tcatacgaag agataaacga tcagactaac gataatataa ccgctagact agatagaata   2760

gacgaaaaac tatctgaaat actaggtatg ttacacacac tagtagtcgc atctgccgga   2820

cctacaagtg ctagagatgg gataagggat gcaatggtag ggttaaggga agaaatgata   2880

gagaaaatta gaaccgaagc attaatgact aacgatagac tcgaagcaat ggctagactt   2940

agaaacgaag aatccgaaaa gatggcaaaa gatacatctg acgaagtgtc acttaatcct   3000

actagcgaaa aattgaataa tctattagag ggaaacgata gtgataacga tctatcactc   3060

gaagatttct gattagttac caatcttcac atcaacacac aataccaaca gaagaccaac   3120

aaactaacca acccaatcat ccaaccaaac atccatccgc caatcagcca aacagccaac   3180

aaaacaacca gccaatccaa aactaaccac ccggaaaaaa tctataatat agttacaaaa   3240

aaaggaaagg gtggggcaaa tatggaaaca tacgtgaaca agcttcacga aggatcaaca   3300

tatacagctg cagtccaata taacgtactc gaaaaagacg acgatcccgc tagcctaaca   3360

atatgggtcc caatgtttca atctagtatg cccgctgatc tattaatcaa agaactagct   3420

aacgttaaca tactagtcaa acaaattagt acacctaagg gaccctcact tagagtgatg   3480

attaatagta gatccgcagt cctagcacaa atgcctagta agtttacaat atgtgctaac   3540

gtaagcttag acgaacgatc aaaactagca tacgatgtga caacaccatg cgaaatcaaa   3600

gcatgttcat tgacatgtct taaatcaaag aatatgctaa caacagtcaa agatctaaca   3660

atgaaaacac ttaatcccac acacgatata atcgcactat gcgaattcga aaatatagtg   3720

actagtaaga aagtgataat ccctacatac cttagatcaa tatccgttag aaataaggat   3780

ctgaatacac tcgaaaatat aacaacaacc gaattcaaaa acgctataac taacgctaag   3840

ataatccctt actccggact attgttagtg ataaccgtaa ccgataataa gggagcattc   3900

aaatacataa aaccccaatc ccaatttata gtcgatttag gcgcatactt agaaaaagaa   3960

tcaatctatt acgttacaac taattggaaa cataccgcta ctagattcgc aatcaaacct   4020

atggaagatt aaccttttc ctctacatca gtgtgttaat tcatacaaac tttctaccta   4080

cattcttcac ttcaccatca caatcacaaa cactctgtgg ttcaaccaat caaacaaaac   4140

ttatctgaag tcccagatca tcccaagtca ttgtttatca gatctagtac tcaaataagt   4200

taataaaaaa tatacacatg gggcaaataa tcattggagg aaatccaact aatcacaata   4260

tctgttaaca tagacaagtc cacacaccat acagaatcaa ccaatggaaa atacatccat   4320
```

aacaatagaa ttctctagca aattttggcc ttactttaca ctaatacaca tgataactac 4380
aatcatatcc ctattaatca taatctcaat tatgatcgca atccttaaca aactatgtga 4440
gtataacgta ttccataaca aaacattcga attgccaaga gctcgagtga atacctgata 4500
aagtagttaa ttaaaaatag tcataacaat gaactaggat atcaagacta acaataacat 4560
tggggcaaat gcaaacatgt ccaaaaacaa ggaccaacgc accgctaaaa cactcgaaag 4620
gacatgggat acccttaatc acctattatt cataagctca tgcttatata aattgaacct 4680
taaatccgtc gcacagataa ccctatcaat actcgcaatg ataatctcaa caagcttaat 4740
catagccgca ataatcttta tcgctagcgc taaccataag gtaaccccaa caaccgcaat 4800
tatacaggac gcaacatccc aaatcaaaaa cacaacccca acatacttaa cccaaaaccc 4860
acaactcgga atctcaccct ctaacccatc cgaaattacc tcacagatta caacgatact 4920
cgcaagtaca acccccggag tcaaatcgac actccaatcg acaaccgtaa agactaagaa 4980
tacaacaaca acccaaaccc aacctagtaa gcctacaact aagcaacgcc aaaacaaacc 5040
tccctctaaa ccgaataacg attttcactt cgaagtgttc aatttcgtac catgctcaat 5100
ttgctctaat aacccaacat gctgggccat atgcaaacgc atcccaaaca agaaacccgg 5160
aaagaaaaca accactaagc caacaaagaa accaaccctt aagacaacca agaaagatcc 5220
aaaaccccaa acaactaagt ctaaagaggt cccaacaact aagccaaccg aagagccaac 5280
aatcaataca actaagacta atataatcac aaccttactg acatctaaca caaccggaaa 5340
tcccgaactg acatcccaaa tggaaacctt tcactcaacc tctagcgaag gcaatccctc 5400
accatcccaa gtctcaacca ctagcgaata cccatcccaa cctagctcac ctcccaatac 5460
ccctagacag tagttactta aaaacatatt atcacaaaag gccttgacca acttaaacag 5520
aatcaaaata aactctgggg caaataacaa tggagttgct aatcctcaaa gcaaatgcaa 5580
tcacaacaat actaacagcc gttacatttt gtttcgctag cggacaaaac ataaccgaag 5640
agttttatca atctacatgt tccgccgtaa gtaaggggta tctatccgca cttagaaccg 5700
gatggtatac tagcgtaata acaatcgaac tatctaatat aaagaagaat aagtgtaacg 5760
gtacagacgc taaggttaaa ttgattaaac aggaactcga taagtataaa aacgccgtaa 5820
ccgaattgca attgttaatg caatctacac aagctactaa taatagggct agacgtgaat 5880
tgcctagatt tatgaattat acacttaata acgctaagaa aactaacgtt acactatcta 5940
agaaacgaaa acgtagattc ttagggtttt tactcggagt cggttccgca atcgctagcg 6000
gagtcgccgt aagtaaagtg ttacacctcg aaggcgaagt gaataagata aaatccgcac 6060
tattatcaac taataaggca gtcgttagcc tatctaacgg agtcagcgta ttgacatcta 6120
aagtgttaga cttaaagaat tatatagata agcaattgtt accaatcgtt aataaacaat 6180
catgttcaat atccaatatc gaaaccgtaa tcgaatttca acagaagaat aatagattac 6240
tcgaaattac tagagaattt agcgtaaacg ctggcgtaac aacacccgta agtacatata 6300
tgttaactaa ttccgaactg ttaagcttaa ttaacgatat gccaattact aacgatcaga 6360
agaaattgat gtctaataac gtacaaatcg ttagacagca atcatattca attatgtcaa 6420
ttataaaaga agaggtactc gcatacgtag tgcaattacc cctatatggc gtaatagata 6480
caccatgttg gaaattgcat acaagtccac tatgtacaac taatacaaaa gagggatcta 6540
atatatgctt aactagaacc gatagggggt ggtattgcga taacgcaggt agcgtaagtt 6600
tctttccaca agccgaaaca tgtaaagtgc aatctaatag agtgttttgc gatacaatga 6660

-continued

```
atagcttaac actacctagc gaagtcaatc tatgtaacgt cgatatattc aatcctaaat   6720
atgattgcaa aattatgact agtaagactg acgtaagtag tagcgtaatt actagtctcg   6780
gtgcaatagt gtcatgttat ggtaagacta agtgtaccgc tagcaataag aatagggga    6840
taataaaaac atttagtaac ggttgcgatt acgttagtaa taagggagtc gataccgtaa   6900
gcgtaggtaa tacactatat tatgttaata aacaggaagg taagtcatta tacgttaaag   6960
gcgaacctat aattaatttt tacgatccat tagtgtttcc atccgacgaa ttcgacgcta   7020
gtataagtca ggtaaacgaa aagattaacc aatcactcgc attcatacga aaatccgacg   7080
aactgttaca caacgttaac gcaggtaaga gtacaactaa cataatgata acaacaatta   7140
taatcgttat aatcgttata ctgttaagct taatcgcagt cggattactg ttatattgta   7200
aagctagatc aacacccgta acactatcta aagaccaatt atccggtata aataatatcg   7260
cattctcaaa ctaaataaaa atagcaccta atcatgttct tacaatggtt tactatctgc   7320
tcatagacaa cccatctgtc attggatttt cttaaaatct gaacttcatc gaaactctca   7380
tctataaacc atctcactta cactatttaa gtagattcct agtttatagt tatataaaac   7440
acaattgcat gccagattaa cttaccatct gtaaaaatga aaactggggc aaatatgtca   7500
cgaaggaatc cttgcaaatt tgaaattcga ggtcattgct taaatggtaa gaggtgtcat   7560
tttagtcata attattttga atggccaccc catgcactgc ttgtaagaca aaactttatg   7620
ttaaacagaa tacttaagtc tatggataaa agtatagata ccttatcaga aataagtgga   7680
gctgcagagt tggacagaac agaagagtat gctcttggtg tagttggagt gctagagagt   7740
tatataggat caataaacaa tataactaaa caatcagcat gtgttgccat gagcaaactc   7800
ctcactgaac tcaatagtga tgatatcaaa aagctgaggg acaatgaaga gctaaattca   7860
cccaagataa gagtgtacaa tactgtcata tcatatattg aaagcaacag gaaaaacaat   7920
aaacaaacta tccatctgtt aaaaagattg ccagcagacg tattgaagaa aaccatcaaa   7980
aacacattgg atatccataa gagcataacc atcaacaacc caaaagaatc aactgttagt   8040
gatacaaatg accatgccaa aaataatgat actacctgac aaatatcctt gtagtataac   8100
ttccatacta ataacaagta gatgtagagt tactatgtat aatcaaaaga acacactata   8160
tttcaatcaa aacaacccaa ataaccatat gtactcaccg aatcaaacat tcaatgaaat   8220
ccattggacc tctcaagaat tgattgacac aattcaaaat tttctacaac atctaggtat   8280
tattgaggat atatatacaa tatatatatt agtgtcataa cactcaattc taacactcac   8340
cacatcgtta cattattaat tcaaacaatt caagttgtgg gacaaaatgg atcccattat   8400
taatggaaat tctgctaacg tatacttaac cgatagttat ttaaaaggcg taatcagttt   8460
tagcgaatgt aacgcattag ggtcatatat ctttaacggt ccatatctta aaaacgatta   8520
tactaatcta atcagtagac agaatccgtt aatcgaacat atgaatctta agaaactgaa   8580
tatcacacaa tctttgatca gtaagtatca taaaggcgaa atcaaactcg aagaacctac   8640
atattttcaa tcactattaa tgacatataa gtctatgaca tctagcgaac agatcgctac   8700
tactaatctg ttgaagaaaa ttattagacg agctatagag atatctgacg ttaaggtata   8760
cgctatactg aataaattgg ggttaaaaga gaaagataag ataaaatcta ataacggtca   8820
agacgaagat aatagtgtaa ttactacaat tattaaagac gatatactat ccgcagtgaa   8880
ggataatcaa tcacatctta aagccgataa aaatcatagt actaaacaaa aagatacaat   8940
taaaactaca ttgttaaaga aattgatgtg ttctatgcaa catccaccta gttggttaat   9000
acattggttt aacttataca ctaagttgaa caatatactt acacaatatc gatcaaacga   9060
```

agtgaaaaat cacggtttta cattgataga taatcaaaca ttaagcggat ttcaattcat 9120
acttaaccaa tacggatgta tagtgtatca taaagaattg aaacgtataa ccgttacaac 9180
atataatcaa ttcttaacat ggaaagatat aagtctatct agattgaacg tatgcttaat 9240
tacatggatt tcgaattgtc ttaatacact taataaatca ttagggttaa gatgcggatt 9300
taataacgtt atacttacac aattgttctt atacggagat tgtatactta agttgttcca 9360
taacgaaggg ttttatataa taaaagaggt tgagggattt ataatgtcat tgatactgaa 9420
tattaccgaa gaggatcaat ttagaaaaag attctataat agtatgttaa acaatataac 9480
tgacgcagct aataaagcgc agaagaatct gttatctaga gtatgtcata cattgttaga 9540
caaaacagtg agcgataata ttataaacgg tagatggatt atactgttat ctaaattctt 9600
aaaattgatt aagttggcag gtgacaataa ccttaataac ttaagcgaat tgtatttctt 9660
attcagaata ttcggacatc ctatggttga cgaacgacaa gctatggacg cagtgaagat 9720
taattgtaac gaaactaaat tctatctatt atctagtcta tctatgctta gaggcgcatt 9780
catatataga attataaaag ggttcgttaa taattataat agatggccta cacttagaaa 9840
cgctatagtg ttaccactta gatggttaac atattataaa ttgaatacat atcctagttt 9900
actcgaatta accgaacgcg atctgatagt gttaagcgga cttagattct atagagagtt 9960
tagattgcct aagaaagtcg atctcgaaat gataattaac gataaggcaa ttagtccacc 10020
taaaaactta atatggacaa gcttccctag aaattatatg cctagtcata tacaaaatta 10080
tatcgaacac gaaaaattga aatttagcga atccgataag tctagaagag tgttagagta 10140
ttacttacgc gataataaat ttaacgaatg cgatctctat aattgcgtag tgaaccaatc 10200
atatcttaat aatcctaatc acgtagtgag tcttacaggt aaggaaagag agttgagcgt 10260
aggtagaatg ttcgctatgc aacccggtat gtttagacaa gtgcaaatac tcgcagaaaa 10320
gatgatagcc gaaaatatac tgcaattctt tcccgaatca ttgactagat acggagattt 10380
agaattgcaa aagatactcg aattgaaagc aggtatatct aataagtcta atagatataa 10440
cgataattat aataattata tatctaagtg tagtattatt accgatctat ctaaattcaa 10500
tcaggcattt agatacgaaa ctagttgtat atgctcagac gtattagacg aattacacgg 10560
agtgcaatct ttgtttagtt ggttacattt aactatacct cacgttacaa ttatatgtac 10620
atatagacac gcaccaccat atataggcga tcatatagtc gatctgaata acgtagacga 10680
acaatccgga ttgtatagat atcacatggg tggcatagag ggatggtgtc aaaaattgtg 10740
gactatagag gcaattagtc tgttagatct aattagtctt aagggtaagt tttcgattac 10800
cgcattgatt aacggtgata atcaatcaat tgatatatct aaaccgatac ggttaatgga 10860
gggacaaaca cacgctcaag ccgattactt actcgcactt aattcactta aactgttata 10920
caaagagtac gcaggtatag ggcataaact taagggtaca gagacatata taagtaggga 10980
tatgcaattt atgagtaaga ctatacaaca taacggagtg tattatcccg ctagtataaa 11040
gaaagtgctt agagtcggac cttggattaa tactatatta gacgatttta aggttagtct 11100
cgaatcaatc ggatcattga cacaagagtt ggagtataga ggcgaatctc tattatgctc 11160
attgatttt agaaacgtat ggttatacaa tcagattgca ttgcaattga aaaatcacgc 11220
actatgtaat aataagttgt acttagacat acttaaagtg ttaaaacatc ttaaaacatt 11280
ctttaatctc gataatatag ataccgcatt aacattgtat atgaatctac ctatgttatt 11340
cggaggggga gatcctaatc tattgtatag atcattctat agacgtacac ctgatttctt 11400

-continued

```
aaccgaagct atagtgcata gcgtattcat actatcatat tatactaatc acgatcttaa  11460
agataagttg caggatctat ctgacgatag attgaataaa ttcttaacat gtattataac  11520
attcgataaa aatcctaacg ctgaattcgt tacacttatg agagatccac aagcattagg  11580
ttcagagaga caggctaaaa ttactagcga aattaataga ttagccgtta ccgaagtgtt  11640
aagtaccgca cctaataaga tattctctaa atccgctcaa cattatacaa caaccgaaat  11700
agatcttaac gatattatgc aaaatatcga acctacatat cctcacggat tacgcgtagt  11760
ttacgaatca ttaccattct ataaagccga aaagatcgtt aacttaatta gcggtacaaa  11820
atcaattact aatatactcg aaaagactag cgcaattgat ttaaccgata tagatagagc  11880
taccgaaatg atgcgtaaaa atataacatt actgatacgt atactaccat tagattgtaa  11940
tagggataaa agagagatac tatctatgga gaatctatca attacagaat tgtcaaaata  12000
cgttagggaa cgatcatggt cactatctaa tatcgtaggc gtaactagtc ctagtattat  12060
gtatactatg gatattaagt atacaactag tacaattagt agcggtataa taatcgaaaa  12120
atataacgtt aatagtctaa cacgtggtga aaggggacct acaaaacctt gggtcggatc  12180
tagtacacaa gagaagaaaa ctatgcccgt atataataga caggtattga ctaagaaaca  12240
acgagatcaa atagatctat tagctaaact cgattgggta tacgctagta tagataataa  12300
agacgaattt atggaagagt tgtcaatcgg tacattaggg ttaacatacg aaaaagctaa  12360
gaaattgttc ccacaatatc tatcagtgaa ttatctacat agattgacag tgagtagtag  12420
accatgcgaa tttcccgcta gtatacccgc atatagaact actaattatc atttcgatac  12480
tagtccaatt aatagaatat taaccgaaaa atacggagac gaagatatag atatcgtatt  12540
ccaaaattgt attagtttcg gattgagtct tatgtccgta gtcgaacaat ttactaacgt  12600
atgtcctaat aggattatac tgatacctaa attgaacgaa atacatctta tgaaacctcc  12660
tatttttaca ggcgatgtcg atatacacaa attgaaacag gttatacaaa aacaacatat  12720
gttcttaccc gataagatat cgttaacgca atacgttgag ttgttcttat caaataaaac  12780
acttaaatca ggtagtcacg ttaatagtaa tctgatactc gcacataaaa ttagcgatta  12840
ctttcataat acatatatat tgagtactaa cttagccgga cattggatac tgattataca  12900
attgatgaaa gatagtaagg gtatattcga aaaagattgg ggtgagggat atataaccga  12960
tcatatgttt ataaacctta aggtcttctt taacgcatat aaaacttatc tattatgttt  13020
tcataaggga tacggtaagg ctaaactcga atgcgatatg aatacatccg atctattatg  13080
cgtactcgaa ttaattgata gtagctattg gaaatctatg agtaaggtat tcttagagca  13140
aaaggtgatc aagtatatac tatctcaaga cgctagtttg catagggtta agggatgtca  13200
tagttttaaa ttatggtttc ttaaaagatt gaacgtagcc gaatttacag tatgtccttg  13260
ggtcgttaac atagattatc atcctacaca tatgaaagct atacttacat atatagatct  13320
agtgagaatg ggattgatta acatagatag aatacatata aagaataaac ataaatttaa  13380
cgacgaattc tatactagta atctattcta tataaattat aatttttccg ataatacaca  13440
tctattaact aaacatatac gtatagctaa tagcgaactc gaaaataatt ataataaatt  13500
gtatcatcct acacccgaaa cattagagaa tatactcgct aatccgatta aatctaacga  13560
taagaaaaca cttaacgatt attgtatagg taaaaacgtt gattcaatta tgttaccatt  13620
actatcaaat aagaaattga ttaaatctag cgctatgatt agaactaatt atagtaaaca  13680
ggatctatat aacttattcc ctatggtcgt aattgataga attatagatc attccggtaa  13740
taccgctaaa tctaatcaat tgtatacaac tactagtcat caaatatcat tagtgcataa  13800
```

tagtactagt ctatattgta tgttaccatg gcatcatatt aatagattca atttcgtttt 13860
tagtagtaca gggtgtaaaa ttagtataga gtatatactt aaagatctta aaattaaaga 13920
tcctaattgt attgcattca taggcgaagg cgcaggtaat ctgttactta gaacagtagt 13980
cgaattgcat cccgatatta gatatatata tagatcactt aaagattgta acgatcatag 14040
tctaccaatc gaattcctta gattgtataa cggtcatata aacatagatt acggcgaaaa 14100
cttaacgata cccgctactg acgctactaa taatatacat tggtcatact tacatattaa 14160
attcgcagaa cctataagtc tattcgtatg cgacgcagaa ttatccgtta cagtgaattg 14220
gtctaaaatt attatcgaat ggtctaaaca cgttagaaaa tgcaaatatt gttctagcgt 14280
taataagtgt atgttaatcg ttaagtatca cgctcaagac gatatagatt ttaaattaga 14340
taatataact atacttaaaa catacgtatg cttaggtagt aagcttaagg gtagcgaagt 14400
atacttagtg ttaacgatag gtccagctaa tatttttccc gtttttaacg tagtgcaaaa 14460
cgctaaattg attctatcta gaactaaaaa ttttataatg cctaagaaag ctgataaaga 14520
gtcaattgac gctaatataa aatcattgat accattctta tgttatccta taactaagaa 14580
agggattaat accgcactat ctaaacttaa atccgtagtg agcggagata tactatctta 14640
tagtatagcc ggtagaaacg aagtttttag taataaattg attaatcata aacatatgaa 14700
tatacttaaa tggtttaatc acgtacttaa ttttagatca accgaattga attataatca 14760
tctatatatg gtcgaatcta catatccata cttatccgaa ctgttaaact cattgactac 14820
taacgaattg aagaaattga ttaaaattac aggtagtctg ttatacaatt ttcataacga 14880
ataatgaata aagatcttat aataaaaatt cccatagcta tacactaaca ctgtattcaa 14940
ttatagttat taaaaattaa aaatcatata attttttaaa taacttttag tgaactaatc 15000
ctaaagttat cattttaatc ttggaggaat aaatttaaac cctaatctaa ttggtttata 15060
tgtgtattaa ctaaattacg agatattagt ttttgacact ttttttctcg t 15111

<210> SEQ ID NO 13
<211> LENGTH: 15111
<212> TYPE: DNA
<213> ORGANISM: respiratory syncytial virus Min_L

<400> SEQUENCE: 13
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780

```
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggattttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
```

```
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aacctttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
aataatctct ttgctaatca taatctccat catgattgca atactaaaca aactttgtga   4440
atataacgta ttccataaca aaacctttga gttaccaaga gctcgagtta atacttgata   4500
aagtagttaa ttaaaaatag tcataacaat gaactaggat atcaagacta acaataacat   4560
tggggcaaat gcaaacatgt ccaaaaacaa ggaccaacgc accgctaaga cattagaaag   4620
gacctgggac actctcaatc atttattatt catatcatcg tgcttatata agttaaatct   4680
taaatctgta gcacaaatca cattatccat tctggcaatg ataatctcaa cttcacttat   4740
aattgcagcc atcatattca tagcctcggc aaaccacaaa gtcacaccaa caactgcaat   4800
catacaagat gcaacaagcc agatcaagaa cacaacccca acatacctca cccagaatcc   4860
tcagcttgga atcagtccct ctaatccgtc tgaaattaca tcacaaatca ccaccatact   4920
agcttcaaca acaccaggag tcaagtcaac cctgcaatcc acaacagtca agaccaaaaa   4980
cacaacaaca actcaaacac aacccagcaa gcccaccaca aaacaacgcc aaaacaaacc   5040
accaagcaaa cccaataatg attttcactt tgaagtgttc aactttgtac cctgcagcat   5100
atgcagcaac aatccaacct gctgggctat ctgcaaaaga ataccaaaca aaaaaccagg   5160
aaagaaaacc actaccaagc ccacaaaaaa accaaccctc aagacaacca aaaaagatcc   5220
caaacctcaa accactaaat caaaggaagt acccaccacc aagcccacag aagagccaac   5280
catcaacacc accaaaacaa acatcataac tacactactc acctccaaca ccacaggaaa   5340
tccagaactc acaagtcaaa tggaaacctt ccactcaact tcctccgaag gcaatccaag   5400
cccttctcaa gtctctacaa catccgagta cccatcacaa ccttcatctc cacccaacac   5460
accacgccag tagttactta aaaacatatt atcacaaaag gccttgacca acttaaacag   5520
```

aatcaaaata aactctgggg caaataacaa tggagttgct aatcctcaaa gcaaatgcaa 5580
ttaccacaat cctcactgca gtcacatttt gttttgcttc tggtcaaaac atcactgaag 5640
aattttatca atcaacatgc agtgcagtta gcaaaggcta tcttagtgct ctgagaactg 5700
gttggtatac cagtgttata actatagaat taagtaatat caagaaaaat aagtgtaatg 5760
gaacagatgc taaggtaaaa ttgataaaac aagaattaga taaatataaa aatgctgtaa 5820
cagaattgca gttgctcatg caaagcacac aagcaacaaa caatcgagcc agaagagaac 5880
taccaaggtt tatgaattat acactcaaca atgccaaaaa aaccaatgta acattaagca 5940
agaaaaggaa aagaagattt cttggttttt tgttaggtgt tggatctgca atcgccagtg 6000
gcgttgctgt atctaaggtc ctgcacctag aaggggaagt gaacaagatc aaaagtgctc 6060
tactatccac aaacaaggct gtagtcagct tatcaaatgg agttagtgtt ttaaccagca 6120
aagtgttaga cctcaaaaac tatatagata aacaattgtt acctattgtg aacaagcaaa 6180
gctgcagcat atcaaatata gaaactgtga tagagttcca acaaaagaac aacagactac 6240
tagagattac cagggaattt agtgttaatg caggcgtaac tacacctgta agcacttaca 6300
tgttaactaa tagtgaatta ttgtcattaa tcaatgatat gcctataaca aatgatcaga 6360
aaaagttaat gtccaacaat gttcaaatag ttagacagca aagttactct atcatgtcca 6420
taataaaaga ggaagtctta gcatatgtag tacaattacc actatatggt gttatagata 6480
caccctgttg gaaactacac acatcccctc tatgtacaac caacacaaaa gaagggtcca 6540
acatctgttt aacaagaact gacagaggat ggtactgtga caatgcagga tcagtatctt 6600
tcttcccaca agctgaaaca tgtaaagttc aatcaaatcg agtattttgt gacacaatga 6660
acagtttaac attaccaagt gaagtaaatc tctgcaatgt tgacatattc aaccccaaat 6720
atgattgtaa aattatgact tcaaaaacag atgtaagcag ctccgttatc acatctctag 6780
gagccattgt gtcatgctat ggcaaaacta aatgtacagc atccaataaa aatcgtggaa 6840
tcataaagac attttctaac gggtgcgatt atgtatcaaa taaaggggtg gacactgtgt 6900
ctgtaggtaa cacattatat tatgtaaata agcaagaagg taaaagtctc tatgtaaaag 6960
gtgaaccaat aataaatttc tatgacccat tagtattccc ctctgatgaa tttgatgcat 7020
caatatctca agtcaacgag aagattaacc agagcctagc atttattcgt aaatccgatg 7080
aattattaca taatgtaaat gctggtaaat ccaccacaaa tatcatgata actactataa 7140
ttatagtgat tatagtaata ttgttatcat taattgctgt tggactgctc ttatactgta 7200
aggccagaag cacaccagtc acactaagca aagatcaact gagtggtata aataatattg 7260
catttagtaa ctaaataaaa atagcaccta atcatgttct tacaatggtt tactatctgc 7320
tcatagacaa cccatctgtc attggatttt cttaaaatct gaacttcatc gaaactctca 7380
tctataaacc atctcactta cactatttaa gtagattcct agtttatagt tatataaaac 7440
acaattgcat gccagattaa cttaccatct gtaaaaatga aaactggggc aaatatgtca 7500
cgaaggaatc cttgcaaatt tgaaattcga ggtcattgct taaatggtaa gaggtgtcat 7560
tttagtcata attattttga atggccaccc catgcactgc ttgtaagaca aaactttatg 7620
ttaaacagaa tacttaagtc tatggataaa agtatagata ccttatcaga aataagtgga 7680
gctgcagagt tggacagaac agaagagtat gctcttggtg tagttggagt gctagagagt 7740
tatataggat caataaacaa tataactaaa caatcagcat gtgttgccat gagcaaactc 7800
ctcactgaac tcaatagtga tgatatcaaa aagctgaggg acaatgaaga gctaaattca 7860
cccaagataa gagtgtacaa tactgtcata tcatatattg aaagcaacag gaaaaacaat 7920

```
aaacaaacta tccatctgtt aaaaagattg ccagcagacg tattgaagaa aaccatcaaa   7980
aacacattgg atatccataa gagcataacc atcaacaacc caaaagaatc aactgttagt   8040
gatacaaatg accatgccaa aaataatgat actacctgac aaatatcctt gtagtataac   8100
ttccatacta ataacaagta gatgtagagt tactatgtat aatcaaaaga acacactata   8160
tttcaatcaa aacaacccaa ataaccatat gtactcaccg aatcaaacat tcaatgaaat   8220
ccattggacc tctcaagaat tgattgacac aattcaaaat tttctacaac atctaggtat   8280
tattgaggat atatatacaa tatatatatt agtgtcataa cactcaattc taacactcac   8340
cacatcgtta cattattaat tcaaacaatt caagttgtgg gacaaaatgg atcccattat   8400
taatggaaat tctgctaacg tatacttaac cgatagttat ttaaaaggcg taatcagttt   8460
tagcgaatgt aacgcattag ggtcatatat ctttaacggt ccatatctta aaaacgatta   8520
tactaatcta atcagtagac agaatccgtt aatcgaacat atgaatctta agaaactgaa   8580
tatcacacaa tctttgatca gtaagtatca taaaggcgaa atcaaactcg aagaacctac   8640
atattttcaa tcactattaa tgacatataa gtctatgaca tctagcgaac agatcgctac   8700
tactaatctg ttgaagaaaa ttattagacg agctatagag atatctgacg ttaaggtata   8760
cgctatactg aataaattgg ggttaaaaga gaaagataag ataaaatcta ataacggtca   8820
agacgaagat aatagtgtaa ttactacaat tattaaagac gatatactat ccgcagtgaa   8880
ggataatcaa tcacatctta aagccgataa aaatcatagt actaaacaaa aagatacaat   8940
taaaactaca ttgttaaaga aattgatgtg ttctatgcaa catccaccta gttggttaat   9000
acattggttt aacttataca ctaagttgaa caatatactt acacaatatc gatcaaacga   9060
agtgaaaaat cacggtttta cattgataga taatcaaaca ttaagcggat ttcaattcat   9120
acttaaccaa tacggatgta tagtgtatca taaagaattg aaacgtataa ccgttacaac   9180
atataatcaa ttcttaacat ggaaagatat aagtctatct agattgaacg tatgcttaat   9240
tacatggatt tcgaattgtc ttaatacact taataaatca ttagggttaa gatgcggatt   9300
taataacgtt atacttacac aattgttctt atacggagat tgtatactta agttgttcca   9360
taacgaaggg ttttatataa taaaagaggt tgagggattt ataatgtcat tgatactgaa   9420
tattaccgaa gaggatcaat ttagaaaaag attctataat agtatgttaa acaatataac   9480
tgacgcagct aataaagcgc agaagaatct gttatctaga gtatgtcata cattgttaga   9540
caaaacagtg agcgataata ttataaacgg tagatggatt atactgttat ctaaattctt   9600
aaaattgatt aagttggcag gtgacaataa ccttaataac ttaagcgaat tgtatttctt   9660
attcagaata ttcggacatc ctatggttga cgaacgacaa gctatggacg cagtgaagat   9720
taattgtaac gaaactaaat tctatctatt atctagtcta tctatgctta gaggcgcatt   9780
catatataga attataaaag ggttcgttaa taattataat agatggccta cacttagaaa   9840
cgctatagtg ttaccactta gatggttaac atattataaa ttgaatacat atcctagttt   9900
actcgaatta accgaacgcg atctgatagt gttaagcgga cttagattct atagagagtt   9960
tagattgcct aagaaagtcg atctcgaaat gataattaac gataaggcaa ttagtccacc  10020
taaaaactta atatggacaa gcttccctag aaattatatg cctagtcata tacaaaatta  10080
tatcgaacac gaaaaattga aatttagcga atccgataag tctagaagag tgttagagta  10140
ttacttacgc gataataaat ttaacgaatg cgatctatat aattgcgtag tgaaccaatc  10200
atatcttaat aatcctaatc acgtagtgag tcttacaggt aaggaaagag agttgagcgt  10260
```

-continued

```
aggtagaatg ttcgctatgc aacccggtat gtttagacaa gtgcaaatac tcgcagaaaa  10320
gatgatagcc gaaaatatac tgcaattctt tcccgaatca ttgactagat acggagattt  10380
agaattgcaa aagatactcg aattgaaagc aggtatatct aataagtcta atagatataa  10440
cgataattat aataattata tatctaagtg tagtattatt accgatctat ctaaattcaa  10500
tcaggcattt agatacgaaa ctagttgtat atgctcagac gtattagacg aattacacgg  10560
agtgcaatct ttgtttagtt ggttacattt aactatacct cacgttacaa ttatatgtac  10620
atatagacac gcaccaccat atataggcga tcatatagtc gatctgaata acgtagacga  10680
acaatccgga ttgtatagat atcacatggg tggcatagag ggatggtgtc aaaaattgtg  10740
gactatagag gcaattagtc tgttagatct aattagtctt aagggtaagt tttcgattac  10800
cgcattgatt aacggtgata atcaatcaat tgatatatct aaaccgatac ggttaatgga  10860
gggacaaaca cacgctcaag ccgattactt actcgcactt aattcactta aactgttata  10920
caaagagtac gcaggtatag ggcataaact taagggtaca gagacatata taagtaggga  10980
tatgcaattt atgagtaaga ctatacaaca taacggagtg tattatcccg ctagtataaa  11040
gaaagtgctt agagtcggac cttggattaa tactatatta gacgatttta aggttagtct  11100
cgaatcaatc ggatcattga cacaagagtt ggagtataga ggcgaatctc tattatgctc  11160
attgattttt agaaacgtat ggttatacaa tcagattgca ttgcaattga aaaatcacgc  11220
actatgtaat aataagttgt acttagacat acttaaagtg ttaaaacatc ttaaaacatt  11280
ctttaatctc gataatatag ataccgcatt aacattgtat atgaatctac ctatgttatt  11340
cggaggggga gatcctaatc tattgtatag atcattctat agacgtacac ctgatttctt  11400
aaccgaagct atagtgcata gcgtattcat actatcatat tatactaatc acgatcttaa  11460
agataagttg caggatctat ctgacgatag attgaataaa ttcttaacat gtattataac  11520
attcgataaa aatcctaacg ctgaattcgt tacacttatg agagatccac aagcattagg  11580
ttcagagaga caggctaaaa ttactagcga aattaataga ttagccgtta ccgaagtgtt  11640
aagtaccgca cctaataaga tattctctaa atccgctcaa cattatacaa caaccgaaat  11700
agatcttaac gatattatgc aaaatatcga acctacatat cctcacggat tacgcgtagt  11760
ttacgaatca ttaccattct ataaagccga aaagatcgtt aacttaatta gcggtacaaa  11820
atcaattact aatatactcg aaaagactag cgcaattgat ttaaccgata tagatagagc  11880
taccgaaatg atgcgtaaaa atataacatt actgatacgt atactaccat tagattgtaa  11940
tagggataaa agagagatac tatctatgga gaatctatca attacagaat tgtcaaaata  12000
cgttagggaa cgatcatggt cactatctaa tatcgtaggc gtaactagtc ctagtattat  12060
gtatactatg gatattaagt atacaactag tacaattagt agcggtataa taatcgaaaa  12120
atataacgtt aatagtctaa cacgtggtga aaggggacct acaaaacctt gggtcggatc  12180
tagtacacaa gagaagaaaa ctatgcccgt atataataga caggtattga ctaagaaaca  12240
acgagatcaa atagatctat tagctaaact cgattgggta tacgctagta tagataataa  12300
agacgaattt atggaagagt tgtcaatcgg tacattaggg ttaacatacg aaaaagctaa  12360
gaaattgttc ccacaatatc tatcagtgaa ttatctacat agattgacag tgagtagtag  12420
accatgcgaa tttcccgcta gtatacccgc atatagaact actaattatc atttcgatac  12480
tagtccaatt aatagaatat taaccgaaaa atacggagac gaagatatag atatcgtatt  12540
ccaaaattgt attagtttcg gattgagtct tatgtccgta gtcgaacaat ttactaacgt  12600
atgtcctaat aggattatac tgatacctaa attgaacgaa atacatctta tgaaacctcc  12660
```

tatttttaca ggcgatgtcg atatacacaa attgaaacag gttatacaaa aacaacatat 12720
gttcttaccc gataagatat cgttaacgca atacgttgag ttgttcttat caaataaaac 12780
acttaaatca ggtagtcacg ttaatagtaa tctgatactc gcacataaaa ttagcgatta 12840
ctttcataat acatatatat tgagtactaa cttagccgga cattggatac tgattataca 12900
attgatgaaa gatagtaagg gtatattcga aaaagattgg ggtgagggat atataaccga 12960
tcatatgttt ataaacctta aggtcttctt taacgcatat aaaacttatc tattatgttt 13020
tcataaggga tacggtaagg ctaaactcga atgcgatatg aatacatccg atctattatg 13080
cgtactcgaa ttaattgata gtagctattg gaaatctatg agtaaggtat tcttagagca 13140
aaaggtgatc aagtatatac tatctcaaga cgctagtttg catagggtta agggatgtca 13200
tagttttaaa ttatggtttc ttaaaagatt gaacgtagcc gaatttacag tatgtccttg 13260
ggtcgttaac atagattatc atcctacaca tatgaaagct atacttacat atatagatct 13320
agtgagaatg ggattgatta acatagatag aatacatata aagaataaac ataaatttaa 13380
cgacgaattc tatactagta atctattcta tataaattat aatttttccg ataatacaca 13440
tctattaact aaacatatac gtatagctaa tagcgaactc gaaaataatt ataataaatt 13500
gtatcatcct acacccgaaa cattagagaa tatactcgct aatccgatta aatctaacga 13560
taagaaaaca cttaacgatt attgtatagg taaaaacgtt gattcaatta tgttaccatt 13620
actatcaaat aagaaattga ttaaatctag cgctatgatt agaactaatt atagtaaaca 13680
ggatctatat aacttattcc ctatggtcgt aattgataga attatagatc attccggtaa 13740
taccgctaaa tctaatcaat tgtatacaac tactagtcat caaatatcat tagtgcataa 13800
tagtactagt ctatattgta tgttaccatg gcatcatatt aatagattca atttcgtttt 13860
tagtagtaca gggtgtaaaa ttagtataga gtatatactt aaagatctta aaattaaaga 13920
tcctaattgt attgcattca taggcgaagg cgcaggtaat ctgttactta gaacagtagt 13980
cgaattgcat cccgatatta gatatatata tagatcactt aaagattgta acgatcatag 14040
tctaccaatc gaattcctta gattgtataa cggtcatata aacatagatt acggcgaaaa 14100
cttaacgata cccgctactg acgctactaa taatatacat tggtcatact tacatattaa 14160
attcgcagaa cctataagtc tattcgtatg cgacgcagaa ttatccgtta cagtgaattg 14220
gtctaaaatt attatcgaat ggtctaaaca cgttagaaaa tgcaaatatt gttctagcgt 14280
taataagtgt atgttaatcg ttaagtatca cgctcaagac gatatagatt ttaaattaga 14340
taatataact atacttaaaa catacgtatg cttaggtagt aagcttaagg gtagcgaagt 14400
atacttagtg ttaacgatag gtccagctaa tatttttccc gtttttaacg tagtgcaaaa 14460
cgctaaattg attctatcta gaactaaaaa ttttataatg cctaagaaag ctgataaaga 14520
gtcaattgac gctaatataa aatcattgat accattctta tgttatccta taactaagaa 14580
agggattaat accgcactat ctaaacttaa atccgtagtg agcggagata tactatctta 14640
tagtatagcc ggtagaaacg aagtttttag taataaattg attaatcata aacatatgaa 14700
tatacttaaa tggtttaatc acgtacttaa ttttagatca accgaattga attataatca 14760
tctatatatg gtcgaatcta catatccata cttatccgaa ctgttaaact cattgactac 14820
taacgaattg aagaaattga ttaaaattac aggtagtctg ttatacaatt ttcataacga 14880
ataatgaata aagatcttat aataaaaatt cccatagcta tacactaaca ctgtattcaa 14940
ttatagttat taaaaattaa aaatcatata atttttaaa taacttttag tgaactaatc 15000

-continued ctaaagttat cattttaatc ttggaggaat aaatttaaac cctaatctaa ttggtttata 15060
tgtgtattaa ctaaattacg agatattagt tttgacact tttttctcg t 15111

<210> SEQ ID NO 14
<211> LENGTH: 15111
<212> TYPE: DNA
<213> ORGANISM: respiratory syncytial virus Min_L-NPM2-1(N88K)L

<400> SEQUENCE: 14
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780
cttgatgaaa gacaggccac atttacattc ctggtcaact atgaaatgaa actattacac 840
aaagtaggaa gcactaaata taaaaaatat actgaataca acacaaaata tggcactttc 900
cctatgccaa tattcatcaa tcatgatggg ttcttagaat gcattggcat taagcctaca 960
aagcatactc ccataatata caagtatgat ctcaatccat aaatttcaac acaatattca 1020
cacaatctaa aacaacaact ctatgcataa ctatactcca tagtccagat ggagcctgaa 1080
aattatagta atttaaaact taaggagaga tataagatag aagatggggc aaatacaacc 1140
atggctctta gcaaagtcaa gttgaatgat acactcaaca aagatcaact tctgtcatcc 1200
agcaaataca ccatccaacg gagcacagga gatagtattg atactcctaa ttatgatgtg 1260
cagaaacaca tcaataagtt atgtggcatg ttattaatca cagaagatgc taatcataaa 1320
ttcactgggt taataggtat gttatatgcg atgtctaggt taggaagaga agacaccata 1380
aaaatactca gagatgcggg atatcatgta aaagcaaatg gagtagatgt aacaacacat 1440
cgtcaagaca ttaatggaaa agaaatgaaa tttgaagtgt taacattggc aagcttaaca 1500
actgaaattc aaatcaacat tgagatagaa tctagaaaat cctacagaaa aatgctaaaa 1560
gaaatgggag aggtagctcc agaatacagg catgactctc ctgattgtgg gatgataata 1620
ttatgtatag cagcattagt aataactaaa ttagcagcag gggacagatc tggtcttaca 1680
gccgtgatta ggagagctaa taatgtccta aaaaatgaaa tgaaacgtta caaaggctta 1740
ctacccaagg acatagccaa cagcttctat gaagtgtttg aaaaacatcc ccactttata 1800
gatgtttttg ttcattttgg tatagcacaa tcttctacca gaggtggcag tagagttgaa 1860
gggatttttg caggattgtt tatgaatgcc tatggtgcag ggcaagtgat gttacggtgg 1920
ggagtcttag caaaatcggt taaaaatatt atgttaggac atgctagtgt gcaagcagaa 1980
atggaacaag ttgttgaggt ttatgaatat gcccaaaaat tgggtggtga agcaggattc 2040

```
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg ggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagtaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aacctttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg ggcaaataa tcattggagg aaatccaact aatcacaata   4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
```

```
aataatctct ttgctaatca taatctccat catgattgca atactaaaca aactttgtga   4440
atataacgta ttccataaca aaacctttga gttaccaaga gctcgagtta atacttgata   4500
aagtagttaa ttaaaaatag tcataacaat gaactaggat atcaagacta acaataacat   4560
tggggcaaat gcaaacatgt ccaaaaacaa ggaccaacgc accgctaaga cattagaaag   4620
gacctgggac actctcaatc atttattatt catatcatcg tgcttatata agttaaatct   4680
taaatctgta gcacaaatca cattatccat tctggcaatg ataatctcaa cttcacttat   4740
aattgcagcc atcatattca tagcctcggc aaaccacaaa gtcacaccaa caactgcaat   4800
catacaagat gcaacaagcc agatcaagaa cacaacccca acatacctca cccagaatcc   4860
tcagcttgga atcagtccct ctaatccgtc tgaaattaca tcacaaatca ccaccatact   4920
agcttcaaca acaccaggag tcaagtcaac cctgcaatcc acaacagtca agaccaaaaa   4980
cacaacaaca actcaaacac aacccagcaa gcccaccaca aaacaacgcc aaaacaaacc   5040
accaagcaaa cccaataatg attttcactt tgaagtgttc aactttgtac cctgcagcat   5100
atgcagcaac aatccaacct gctgggctat ctgcaaaaga ataccaaaca aaaaaccagg   5160
aaagaaaacc actaccaagc ccacaaaaaa accaaccctc aagacaacca aaaaagatcc   5220
caaacctcaa accactaaat caaaggaagt acccaccacc aagcccacag aagagccaac   5280
catcaacacc accaaaacaa acatcataac tacactactc acctccaaca ccacaggaaa   5340
tccagaactc acaagtcaaa tggaaacctt ccactcaact tcctccgaag gcaatccaag   5400
cccttctcaa gtctctacaa catccgagta cccatcacaa ccttcatctc cacccaacac   5460
accacgccag tagttactta aaaacatatt atcacaaaag gccttgacca acttaaacag   5520
aatcaaaata aactctgggg caaataacaa tggagttgct aatcctcaaa gcaaatgcaa   5580
ttaccacaat cctcactgca gtcacatttt gttttgcttc tggtcaaaac atcactgaag   5640
aattttatca atcaacatgc agtgcagtta gcaaaggcta tcttagtgct ctgagaactg   5700
gttggtatac cagtgttata actatagaat taagtaatat caagaaaaat aagtgtaatg   5760
gaacagatgc taaggtaaaa ttgataaaac aagaattaga taaatataaa aatgctgtaa   5820
cagaattgca gttgctcatg caaagcacac aagcaacaaa caatcgagcc agaagagaac   5880
taccaaggtt tatgaattat acactcaaca atgccaaaaa aaccaatgta acattaagca   5940
agaaaaggaa aagaagattt cttggttttt tgttaggtgt tggatctgca atcgccagtg   6000
gcgttgctgt atctaaggtc ctgcacctag aaggggaagt gaacaagatc aaaagtgctc   6060
tactatccac aaacaaggct gtagtcagct tatcaaatgg agttagtgtt ttaaccagca   6120
aagtgttaga cctcaaaaac tatatagata aacaattgtt acctattgtg aacaagcaaa   6180
gctgcagcat atcaaatata gaaactgtga tagagttcca acaaaagaac aacagactac   6240
tagagattac cagggaattt agtgttaatg caggcgtaac tacacctgta agcacttaca   6300
tgttaactaa tagtgaatta ttgtcattaa tcaatgatat gcctataaca aatgatcaga   6360
aaaagttaat gtccaacaat gttcaaatag ttagacagca aagttactct atcatgtcca   6420
taataaaaga ggaagtctta gcatatgtag tacaattacc actatatggt gttatagata   6480
caccctgttg gaaactacac acatcccctc tatgtacaac caacacaaaa gaagggtcca   6540
acatctgttt aacaagaact gacagaggat ggtactgtga caatgcagga tcagtatctt   6600
tcttcccaca agctgaaaca tgtaaagttc aatcaaatcg agtattttgt gacacaatga   6660
acagtttaac attaccaagt gaagtaaatc tctgcaatgt tgacatattc aaccccaaat   6720
atgattgtaa aattatgact tcaaaaacag atgtaagcag ctccgttatc acatctctag   6780
```

```
gagccattgt gtcatgctat ggcaaaacta aatgtacagc atccaataaa aatcgtggaa   6840
tcataaagac attttctaac gggtgcgatt atgtatcaaa taaaggggtg gacactgtgt   6900
ctgtaggtaa cacattatat tatgtaaata agcaagaagg taaaagtctc tatgtaaaag   6960
gtgaaccaat aataaatttc tatgacccat tagtattccc ctctgatgaa tttgatgcat   7020
caatatctca agtcaacgag aagattaacc agagcctagc atttattcgt aaatccgatg   7080
aattattaca taatgtaaat gctggtaaat ccaccacaaa tatcatgata actactataa   7140
ttatagtgat tatagtaata ttgttatcat taattgctgt tggactgctc ttatactgta   7200
aggccagaag cacaccagtc acactaagca aagatcaact gagtggtata aataatattg   7260
catttagtaa ctaaataaaa atagcaccta atcatgttct tacaatggtt tactatctgc   7320
tcatagacaa cccatctgtc attggatttt cttaaaatct gaacttcatc gaaactctca   7380
tctataaacc atctcactta cactatttaa gtagattcct agtttatagt tatataaaac   7440
acaattgcat gccagattaa cttaccatct gtaaaaatga aaactggggc aaatatgtca   7500
cgaaggaatc cttgcaaatt tgaaattcga ggtcattgct taaatggtaa gaggtgtcat   7560
tttagtcata attattttga atggccaccc catgcactgc ttgtaagaca aaactttatg   7620
ttaaacagaa tacttaagtc tatggataaa agtatagata ccttatcaga aataagtgga   7680
gctgcagagt tggacagaac agaagagtat gctcttggtg tagttggagt gctagagagt   7740
tatataggat caataaaaaa tataactaaa caatcagcat gtgttgccat gagcaaactc   7800
ctcactgaac tcaatagtga tgatatcaaa aagctgaggg acaatgaaga gctaaattca   7860
cccaagataa gagtgtacaa tactgtcata tcatatattg aaagcaacag gaaaaacaat   7920
aaacaaacta tccatctgtt aaaaagattg ccagcagacg tattgaagaa aaccatcaaa   7980
aacacattgg atatccataa gagcataacc atcaacaacc caaaagaatc aactgttagt   8040
gatacaaatg accatgccaa aaataatgat actacctgac aaatatcctt gtagtataac   8100
ttccatacta ataacaagta gatgtagagt tactatgtat aatcaaaaga acacactata   8160
tttcaatcaa aacaacccaa ataaccatat gtactcaccg aatcaaacat tcaatgaaat   8220
ccattggacc tctcaagaat tgattgacac aattcaaaat tttctacaac atctaggtat   8280
tattgaggat atatatacaa tatatatatt agtgtcataa cactcaattc taacactcac   8340
cacatcgtta cattattaat tcaaacaatt caagttgtgg gacaaaatgg atcccattat   8400
taatggaaat tctgctaacg tatacttaac cgatagttat ttaaaaggcg taatcagttt   8460
tagcgaatgt aacgcattag ggtcatatat ctttaacggt ccatatctta aaaacgatta   8520
tactaatcta atcagtagac agaatccgtt aatcgaacat atgaatctta agaaactgaa   8580
tatcacacaa tctttgatca gtaagtatca taaaggcgaa atcaaactcg aagaacctac   8640
atattttcaa tcactattaa tgacatataa gtctatgaca tctagcgaac agatcgctac   8700
tactaatctg ttgaagaaaa ttattagacg agctatagag atatctgacg ttaaggtata   8760
cgctatactg aataaattgg ggttaaaaga gaaagataag ataaaatcta ataacggtca   8820
agacgaagat aatagtgtaa ttactacaat tattaaagac gatatactat ccgcagtgaa   8880
ggataatcaa tcacatctta aagccgataa aaatcatagt actaaacaaa aagatacaat   8940
taaaactaca ttgttaaaga aattgatgtg ttctatgcaa catccaccta gttggttaat   9000
acattggttt aacttataca ctaagttgaa caatatactt acacaatatc gatcaaacga   9060
agtgaaaaat cacggtttta cattgataga taatcaaaca ttaagcggat ttcaattcat   9120
```

-continued

```
acttaaccaa tacggatgta tagtgtatca taaagaattg aaacgtataa ccgttacaac   9180
atataatcaa ttcttaacat ggaaagatat aagtctatct agattgaacg tatgcttaat   9240
tacatggatt tcgaattgtc ttaatacact taataaatca ttagggttaa gatgcggatt   9300
taataacgtt atacttacac aattgttctt atacggagat tgtatactta agttgttcca   9360
taacgaaggg ttttatataa taaaagaggt tgagggattt ataatgtcat tgatactgaa   9420
tattaccgaa gaggatcaat ttagaaaaag attctataat agtatgttaa acaatataac   9480
tgacgcagct aataaagcgc agaagaatct gttatctaga gtatgtcata cattgttaga   9540
caaaacagtg agcgataata ttataaacgg tagatggatt atactgttat ctaaattctt   9600
aaaattgatt aagttggcag gtgacaataa ccttaataac ttaagcgaat tgtatttctt   9660
attcagaata ttcggacatc ctatggttga cgaacgacaa gctatggacg cagtgaagat   9720
taattgtaac gaaactaaat tctatctatt atctagtcta tctatgctta gaggcgcatt   9780
catatataga attataaaag ggttcgttaa taattataat agatggccta cacttagaaa   9840
cgctatagtg ttaccactta gatggttaac atattataaa ttgaatacat atcctagttt   9900
actcgaatta accgaacgcg atctgatagt gttaagcgga cttagattct atagagagtt   9960
tagattgcct aagaaagtcg atctcgaaat gataattaac gataaggcaa ttagtccacc  10020
taaaaactta atatggacaa gcttccctag aaattatatg cctagtcata tacaaaatta  10080
tatcgaacac gaaaaattga aatttagcga atccgataag tctagaagag tgttagagta  10140
ttacttacgc gataataaat ttaacgaatg cgatctatat aattgcgtag tgaaccaatc  10200
atatcttaat aatcctaatc acgtagtgag tcttacaggt aaggaaagag agttgagcgt  10260
aggtagaatg ttcgctatgc aacccggtat gtttagacaa gtgcaaatac tcgcagaaaa  10320
gatgatagcc gaaaatatac tgcaattctt tcccgaatca ttgactagat acggagattt  10380
agaattgcaa aagatactcg aattgaaagc aggtatatct aataagtcta atagatataa  10440
cgataattat aataattata tatctaagtg tagtattatt accgatctat ctaaattcaa  10500
tcaggcattt agatacgaaa ctagttgtat atgctcagac gtattagacg aattacacgg  10560
agtgcaatct ttgtttagtt ggttacattt aactatacct cacgttacaa ttatatgtac  10620
atatagacac gcaccaccat atataggcga tcatatagtc gatctgaata acgtagacga  10680
acaatccgga ttgtatagat atcacatggg tggcatagag ggatggtgtc aaaaattgtg  10740
gactatagag gcaattagtc tgttagatct aattagtctt aagggtaagt tttcgattac  10800
cgcattgatt aacggtgata atcaatcaat tgatatatct aaaccgatac ggttaatgga  10860
gggacaaaca cacgctcaag ccgattactt actcgcactt aattcactta aactgttata  10920
caaagagtac gcaggtatag ggcataaact taagggtaca gagacatata taagtaggga  10980
tatgcaattt atgagtaaga ctatacaaca taacggagtg tattatcccg ctagtataaa  11040
gaaagtgctt agagtcggac cttggattaa tactatatta gacgatttta aggttagtct  11100
cgaatcaatc ggatcattga cacaagagtt ggagtataga ggcgaatctc tattatgctc  11160
attgattttt agaaacgtat ggttatacaa tcagattgca ttgcaattga aaaatcacgc  11220
actatgtaat aataagttgt acttagacat acttaaagtg ttaaaacatc ttaaaacatt  11280
ctttaatctc gataatatag ataccgcatt aacattgtat atgaatctac ctatgttatt  11340
cggaggggga gatcctaatc tattgtatag atcattctat agacgtacac ctgatttctt  11400
aaccgaagct atagtgcata gcgtattcat actatcatat tatactaatc acgatcttaa  11460
agataagttg caggatctat ctgacgatag attgaataaa ttcttaacat gtattataac  11520
```

attcgataaa aatcctaacg ctgaattcgt tacacttatg agagatccac aagcattagg 11580
ttcagagaga caggctaaaa ttactagcga aattaataga ttagccgtta ccgaagtgtt 11640
aagtaccgca cctaataaga tattctctaa atccgctcaa cattatacaa caaccgaaat 11700
agatcttaac gatattatgc aaaatatcga acctacatat cctcacggat tacgcgtagt 11760
ttacgaatca ttaccattct ataaagccga aaagatcgtt aacttaatta gcggtacaaa 11820
atcaattact aatatactcg aaaagactag cgcaattgat ttaaccgata tagatagagc 11880
tatcgaaatg atgcgtaaaa atataacatt actgatacgt atactaccat tagattgtaa 11940
tagggataaa agagagatac tatctatgga gaatctatca attacagaat tgtcaaaata 12000
cgttagggaa cgatcatggt cactatctaa tatcgtaggc gtaactagtc ctagtattat 12060
gtatactatg gatattaagt atacaactag tacaattagt agcggtataa taatcgaaaa 12120
atataacgtt aatagtctaa cacgtggtga aaggggacct acaaaacctt gggtcggatc 12180
tagtacacaa gagaagaaaa ctatgcccgt atataataga caggtattga ctaagaaaca 12240
acgagatcaa atagatctat tagctaaact cgattgggta tacgctagta tagataataa 12300
agacgaattt atggaagagt tgtcaatcgg tacattaggg ttaacatacg aaaaagctaa 12360
gaaattgttc ccacaatatc tatcagtgaa ttatctacat agattgacag tgagtagtag 12420
accatgcgaa tttcccgcta gtatacccgc atatagaact actaattatc atttcgatac 12480
tagtccaatt aatagaatat taaccgaaaa atacggagac gaagatatag atatcgtatt 12540
ccaaaattgt attagtttcg gattgagtct tatgtccgta gtcgaacaat ttactaacgt 12600
atgtcctaat aggattatac tgatacctaa attgaacgaa atacatctta tgaaacctcc 12660
tatttttaca ggcgatgtcg atatacacaa attgaaacag gttatacaaa aacaacatat 12720
gttcttaccc gataagatat cgttaacgca atacgttgag ttgttcttat caaataaaac 12780
acttaaatca ggtagtcacg ttaatagtaa tctgatactc gcacataaaa ttagcgatta 12840
ctttcataat acatatatat tgagtactaa cttagccgga cattggatac tgattataca 12900
attgatgaaa gatagtaagg gtatattcga aaaagattgg ggtgagggat atataaccga 12960
tcatatgttt ataaacctta aggtcttctt taacgcatat aaaacttatc tattatgttt 13020
tcataaggga tacggtaagg ctaaactcga atgcgatatg aatacatccg atctattatg 13080
cgtactcgaa ttaattgata gtagctattg gaaatctatg agtaaggtat tcttagagca 13140
aaaggtgatc aagtatatac tatctcaaga cgctagtttg catagggtta agggatgtca 13200
tagttttaaa ttatggtttc ttaaaagatt gaacgtagcc gaatttacag tatgtccttg 13260
ggtcgttaac atagattatc atcctacaca tatgaaagct atacttacat atatagatct 13320
agtgagaatg ggattgatta acatagatag aatacatata aagaataaac ataaatttaa 13380
cgacgaattc tatactagta atctattcta tataaattat aatttttccg ataatacaca 13440
tctattaact aaacatatac gtatagctaa tagcgaactc gaaaataatt ataataaatt 13500
gtatcatcct acacccgaaa cattagagaa tatactcgct aatccgatta aatctaacga 13560
taagaaaaca cttaacgatt attgtatagg taaaaacgtt gattcaatta tgttaccatt 13620
actatcaaat aagaaattga ttaaatctag cgctatgatt agaactaatt atagtaaaca 13680
ggatctatat aacttattcc ctatggtcgt aattgataga attatagatc attccggtaa 13740
taccgctaaa tctaatcaat tgtatacaac tactagtcat caaatatcat tagtgcataa 13800
tagtactagt ctatattgta tgttaccatg gcatcatatt aatagattca atttcgtttt 13860

-continued

```
tagtagtaca gggtgtaaaa ttagtataga gtatatactt aaagatctta aaattaaaga  13920
tcctaattgt attgcattca taggcgaagg cgcaggtaat ctgttactta gaacagtagt  13980
cgaattgcat cccgatatta gatatatata tagatcactt aaagattgta acgatcatag  14040
tctaccaatc gaattcctta gattgtataa cggtcatata aacatagatt acggcgaaaa  14100
cttaacgata cccgctactg acgctactaa taatatacat tggtcatact tacatattaa  14160
attcgcagaa cctataagtc tattcgtatg cgacgcagaa ttatccgtta cagtgaattg  14220
gtctaaaatt attatcgaat ggtctaaaca cgttagaaaa tgcaaatatt gttctagcgt  14280
taataagtgt atgttaatcg ttaagtatca cgctcaagac gatatagatt ttaaattaga  14340
taatataact atacttaaaa catacgtatg cttaggtagt aagcttaagg gtagcgaagt  14400
atacttagtg ttaacgatag gtccagctaa tatttttccc gtttttaacg tagtgcaaaa  14460
cgctaaattg attctatcta gaactaaaaa ttttataatg cctaagaaag ctgataaaga  14520
gtcaattgac gctaatataa aatcattgat accattctta tgttatccta taactaagaa  14580
agggattaat accgcactat ctaaacttaa atccgtagtg agcggagata tactatctta  14640
tagtatagcc ggtagaaacg aagtttttag taataaattg attaatcata aacatatgaa  14700
tatacttaaa tggtttaatc acgtacttaa ttttagatca accgaattga attataatca  14760
tctatatatg gtcgaatcta catatccata cttatccgaa ctgttaaact cattgactac  14820
taacgaattg aagaaattga ttaaaattac aggtagtctg ttatacaatt ttcataacga  14880
ataatgaata aagatcttat aataaaaatt cccatagcta tacactaaca ctgtattcaa  14940
ttatagttat taaaaattaa aaatcatata atttttaaa taacttttag tgaactaatc  15000
ctaaagttat catttaatc ttggaggaat aaatttaaac cctaatctaa ttggtttata  15060
tgtgtattaa ctaaattacg agatattagt ttttgacact ttttttctcg t           15111
```